(12) United States Patent
Kong et al.

(10) Patent No.: US 12,037,646 B2
(45) Date of Patent: Jul. 16, 2024

(54) COMPANION DIAGNOSTIC BIOMARKER FOR ANTI-HER2 THERAPY AND USE THEREOF

(71) Applicant: INDUSTRY-UNIVERSITY COOPERATION FOUNDATION HANYANG UNIVERSITY, Seoul (KR)

(72) Inventors: Gu Kong, Seoul (KR); Jeong Yeon Lee, Jeonju-si (KR); Hee-Joo Choi, Anyang-si (KR); Ha Ni Jo, Seoul (KR)

(73) Assignee: INDUSTRY-UNIVERSITY COOPERATION FOUNDATION HANYANG UNIVERSITY, Seoul (KR)

(*) Notice: Subject to any disclaimer, the term of this patent is extended or adjusted under 35 U.S.C. 154(b) by 474 days.

(21) Appl. No.: 16/778,237

(22) Filed: Jan. 31, 2020

(65) Prior Publication Data
US 2020/0248271 A1    Aug. 6, 2020

(30) Foreign Application Priority Data
Feb. 1, 2019  (KR) .......................... 10-2019-0013863

(51) Int. Cl.
*C12Q 1/6886* (2018.01)
(52) U.S. Cl.
CPC ..... *C12Q 1/6886* (2013.01); *C12Q 2600/106* (2013.01); *C12Q 2600/156* (2013.01); *C12Q 2600/158* (2013.01)
(58) Field of Classification Search
CPC .................................................. C12Q 1/6886
USPC ..................................................... 424/133.1
See application file for complete search history.

(56) References Cited

FOREIGN PATENT DOCUMENTS

WO   WO 2017/163076 A1 * 9/2017

OTHER PUBLICATIONS

Naidoo et al (Mol Cancer Ther, 2017, 18(1): 306-315).*
Johnson et al (Cell Reports, 2016, 17: 2367-2381).*
Paculová et al (Cell Div, 2017, 12(7): 1-10).*
Kalnisha Naidoo et al., "Evaluation of CDK12 Protein Expression as a Potential Novel Biomarker for DNA Damage Response Targeted Therapies in Breast Cancer", Mol Cancer Ther., Jan. 2018, vol. 17, No. 1, pp. 306-315 (20 pages total).

* cited by examiner

*Primary Examiner* — Sean E Aeder
(74) *Attorney, Agent, or Firm* — Sughrue Mion, PLLC

(57) ABSTRACT

A function of cyclin-dependent kinase 12 (CDK12) as a biomarker for a human epidermal growth factor receptor 2 (HER2)-positive cancer and anti-HER2 therapy, and a use of the CDK12 are provided. The CDK12 may be used for companion diagnostics of a HER2-targeted therapeutic agent for a subject having HER2+ cancer as a prognostic factor and a predictive factor for response of the subject to the anti-HER2-targeted therapeutic agent in HER2+ cancer, or used to check the probability of expressing resistance to the HER2-targeted therapeutic agent. When the CDK12 is amplified or expressed at a level higher than a reference value, the CDK12 may be suppressed to overcome the resistance to the HER2 therapeutic agent and improve a therapeutic effect, thereby improving the therapeutic efficiency of HER2-positive cancer.

11 Claims, 57 Drawing Sheets
Specification includes a Sequence Listing.

COMPANION DIAGNOSTIC BIOMARKER FOR ANTI-HER2 THERAPY AND USE THEREOF

CROSS-REFERENCE TO RELATED APPLICATION

This application claims priority to and the benefit of Korean Patent Application No. 2019-0013863, filed Feb. 1, 2019, the disclosure of which is incorporated herein by reference in its entirety.

BACKGROUND

1. Field of the Invention

The present invention relates to a biomarker for a human epidermal growth factor receptor 2 (HER2)-positive cancer and anti-HER2 therapy, and a use of the same.

2. Discussion of Related Art

Human epidermal growth factor receptor 2-positive (HER2+) breast cancer, which is defined by HER2 amplification or overexpression, accounts for 15% to 20% of all breast cancers[1,2]. HER2+ breast cancer is considered to be the most aggressive subtype of breast cancer, but development of HER2-targeted drugs gives significant clinical benefits to patients suffering from HER2+ breast cancer.

Trastuzumab, which is the first approved anti-HER2 monoclonal antibody, is the most commonly used drug in the world as the standard therapy for HER2+ breast cancer patients[3,4]. However, the accumulated clinical evidence reveals that the response of HER2+ breast cancers to trastuzumab therapy varies, with 50% or more of patients having no response to or acquiring resistance to trastuzumab[5-7]. Therefore, there is a need for development of a better therapeutic strategy capable of defining a biological mechanism associated with the HER2+ breast cancer and more widely applying the biological mechanism to all subgroups of HER2+ breast cancers.

HER2+ breast cancers are clearly defined as belonging to one of the subgroups of breast cancers which are clinically affected by the anti-HER2 therapy, but the biological and molecular heterogeneity of the subgroups according to the genome analysis of HER2+ tumors suggest the need for additional description and classification of the HER2+ breast cancers. Recent whole-genome sequencing and transcriptome analysis of HER2+ breast cancer revealed that it includes various subgroups of breast cancers showing different gene expression and distinct genomic features, including amplification of genes on chromosome (Chr) 17 and other chromosomal regions and somatic mutations of multigenes[8]. Also, such genomic heterogeneity causes various responses to the HER2-targeted therapy[4,9,10]. The abnormality of Chr17, which causes HER2 amplification, is one of the most representative features of the HER2+ breast cancers[1,2,11]. However, little is known about a molecular alteration of a HER2 amplicon by the Chr17 abnormality, and its clinical effects.

Cyclin-dependent kinase 12 (CDK12) is positioned at Chr17q12, and shows high co-amplification with HER2 which accounts for approximately 90% of HER2+ breast cancers[12-14]. CDK12 kinase activity phosphorylates a C-terminal domain (CTD) of RNA polymerase II at serine 2 (PolII CTD-ser2) to regulate PolII-mediated transcription initiation. Also, CDK12 plays an important role in various biological processes such as cell cycle initiation, DNA damage repair, and the like[15-18]. Genome analysis confirmed frequent alterations of CDK12 through mutation, relocation, or amplification in human cancers, suggesting that CDK12 is a potential cancer target gene[12,19-22]. In addition, the CDK12 deficiency in an ovarian cancer having a functionally inactive CDK12 mutation improves sensitivity to olaparib which is a poly(ADP-ribose) polymerase (PARP) ½ inhibitor. Similarly, the resistance to the PARP1/2 inhibitor was reversed by administration of dinaciclib, which is a CDK12 inhibitor in a triple-negative breast cancer (TNBC)[24]. However, a functional role of CDK12 is not generally known in the types of cancers including amplification of CDK12 even when the frequency of CDK12 amplification in human cancer is high.

Therefore, there is still a need for a new therapeutic strategy for improving the effectiveness of anti-HER2 therapy in HER2-positive breast cancer and overcoming drug resistance to HER2 targeted therapeutic agents.

SUMMARY OF THE INVENTION

To solve the above problems, the present inventors have conducted continuous research and newly found that responsiveness to a HER2-targeted therapeutic agent in a HER2+ cancer is associated with CDK12, and suggested a new strategy for HER2+ cancer therapy.

Specifically, the present inventors have newly found that CDK12 can be a biomarker capable of replacing HER2 in HER2+ breast cancer because CDK12 amplification in HER2+ breast cancer includes many HER2-specific functions including regulation of cancer stem cells, tumor growth, and a response to trastuzumab. In particular, the present inventors have also confirmed that CDK12 kinase inhibition may become an effective method for widely treating various types of HER2+ breast cancers, and may overcome the resistance to trastuzumab in anti-HER2 therapy, and improve an effect of the anti-HER2 therapeutic agent. Therefore, the present invention has been completed based on the facts.

To suggest a new strategy for HER2 positive cancer therapy, a present invention provides a companion diagnostic composition for HER2 targeted therapy in a human epidermal growth factor receptor 2 (HER2)-positive cancer, comprising an agent for measuring a CDK12 level.

The companion diagnostic composition may be intended to provide information on the need for administration of a HER2 targeted therapeutic agent; the need for administration of a CDK12 inhibitor; the probability of expressing drug resistance to the HER2 targeted therapeutic agent; sensitivity to the HER2 targeted therapeutic agent; prediction of a treatment outcome with the HER2 targeted therapeutic agent; or the need for co-administration of the HER2 targeted therapeutic agent and the CDK12 inhibitor.

The cancer may be a HER2-positive breast cancer.

The agent for measuring the CDK12 level is selected from the group consisting of a sense primer, an antisense primer, an antibody, an aptamer, and a probe, which complementarily or specifically bind to CDK12.

The HER2 targeted therapeutic agent is selected from the group consisting of trastuzumab, pertuzumab, and trastuzumab emtansine (T-DM1).

The present invention also provide a method of providing companion diagnostic information on HER2 targeted therapy in a human epidermal growth factor receptor 2 (HER2)-positive cancer, comprising: measuring a CDK12 level in a sample obtained from a subject suffering from a human epidermal growth factor receptor 2 (HER2)-positive cancer.

The method may be intended to provide information on the need for administration of a HER2 targeted therapeutic agent; the need for administration of a CDK12 inhibitor; the probability of expressing drug resistance to the HER2 targeted therapeutic agent; sensitivity to the HER2 targeted therapeutic agent; prediction of a treatment outcome with the HER2 targeted therapeutic agent; or the need for co-administration of the HER2 targeted therapeutic agent and the CDK12 inhibitor.

The method further comprises providing information on the probability of one or more of the following applying to the subject who provided the sample when the copy number or the expression level of CDK12 in the sample is greater than a reference value:
the need for administration of the CDK12 inhibitor; a high probability of expressing drug resistance to the HER2 targeted therapeutic agent; low sensitivity to the HER2 targeted therapeutic agent; poor treatment outcome with the HER2 targeted therapeutic agent; or the need for co-administration of the HER2 targeted therapeutic agent and the CDK12 inhibitor.

The HER2 targeted therapeutic agent may be selected from the group consisting of trastuzumab, pertuzumab, and trastuzumab emtansine (T-DM1).

The CDK12 level may be determined by conducting a method selected from the group consisting of fluorescence in situ hybridization (FISH), a comparative genomic hybridization (CGH)-based array, a single nucleotide polymorphism array (a SNP array), sequence assembly comparison, paired-end sequencing, a multiplex ligation dependent probe amplification (MLPA) method, a multiplex amplifiable probe hybridization (MAPH) method, quantitative multiplex PCR of short fluorescent fragments (QMPSF), a microsatellite genotyping method, Southern blotting, immunohistochemistry (IHC), a polymerase chain reaction (PCR), a quantitative polymerase chain reaction (qPCR), a quantitative real-time polymerase chain reaction (qRT-PCR), a real-time polymerase chain reaction (real-time PCR), microarray-based comparative genomic hybridization, and a ligase chain reaction (LCR).

The present invention also provides a companion diagnostic kit for HER2 targeted therapy in a HER2-positive cancer, comprising an agent for measuring a CDK12 level.

The companion diagnostic kit may further comprise an agent for measuring a human epidermal growth factor receptor 2 (HER2) level.

The agent may be selected from the group consisting of a sense primer, an antisense primer, an antibody, an aptamer, and a probe, which are complementary or specific to CDK12.

The companion diagnostic kit may be intended to provide information on the need for administration of a HER2 targeted therapeutic agent; the need for administration of a CDK12 inhibitor; the probability of expressing drug resistance to the HER2 targeted therapeutic agent; sensitivity to the HER2 targeted therapeutic agent; prediction of a treatment outcome with the HER2 targeted therapeutic agent; or the need for co-administration of the HER2 targeted therapeutic agent and the CDK12 inhibitor.

The present invention also provides an anti-cancer pharmaceutical composition for treating a subject who has or is expected to have drug resistance to a HER2 targeted therapeutic agent, comprising a CDK12 inhibitor as an active ingredient, wherein a copy number or an expression level of CDK12 in the subject having a human epidermal growth factor receptor 2 (HER2)-positive cancer is higher than a reference value.

The CDK12 inhibitor may comprise one or more selected from the group consisting of an antisense nucleotide, small interfering RNA (siRNA), short hairpin RNA (shRNA), a peptide, a peptide mimetic, an aptamer, and an antibody, which complementarily or specifically bind to CDK12

The CDK12 inhibitor may comprise one or more selected from the group consisting of dinaciclib and THZ-531.

The anti-cancer pharmaceutical composition may be administered together with the HER2 targeted therapeutic agent, or co-administered simultaneously or sequentially with the HER2 targeted therapeutic agent.

The HER2 targeted therapeutic agent may be selected from the group consisting of trastuzumab, pertuzumab, and trastuzumab emtansine (T-DM1).

The anti-cancer pharmaceutical composition may further comprise the HER2 targeted therapeutic agent.

The present invention also provides a pharmaceutical composition for suppressing or improving resistance to a human epidermal growth factor receptor 2 (HER2) targeted therapeutic agent in a subject who has or is expected to have drug resistance to a HER2 targeted therapeutic agent, comprising a CDK12 inhibitor as an active ingredient, wherein a copy number or an expression level of CDK12 in the subject having a human epidermal growth factor receptor 2 (HER2)-positive cancer is higher than a reference value; and wherein the CDK12 inhibitor comprises one or more selected from the group consisting of an antisense nucleotide, small interfering RNA (siRNA), short hairpin RNA (shRNA), a peptide, a peptide mimetic, an aptamer, and an antibody, which complementarily or specifically bind to CDK12, or comprises one or more selected from the group consisting of dinaciclib and THZ-531.

The pharmaceutical composition may further comprise the HER2 targeted therapeutic agent.

The present invention also provides a therapy adjuvant composition for HER2 targeted therapy in a subject having a human epidermal growth factor receptor 2 (HER2)-positive cancer, comprising a CDK12 inhibitor as an active ingredient, wherein the CDK12 inhibitor comprises one or more selected from the group consisting of an antisense nucleotide, small interfering RNA (siRNA), short hairpin RNA (shRNA), a peptide, a peptide mimetic, an aptamer, and an antibody, which complementarily or specifically bind to CDK12, or comprises one or more selected from the group consisting of dinaciclib and THZ-531.

The therapy adjuvant composition may be intended to treat a subject whose copy number or expression level of CDK12 is higher than a reference value and who has or is expected to have drug resistance to the HER2 targeted therapeutic agent.

The present invention also provides a composition for screening a drug for improving resistance to a HER2 targeted therapeutic agent or for co-administration with the HER2 targeted therapeutic agent, comprising CDK12.

The present invention also provides a method of screening a material for improving resistance to a HER2 targeted therapeutic agent or for co-administration with the HER2 targeted therapeutic agent, comprising:
allowing CDK12 to come into contact with a candidate material; and selecting a candidate material for reducing a copy number of a CDK12 gene; an expression level of CDK12 mRNA; or an expression level of a CDK12 protein, or inhibiting expression of the CDK12 protein.

The present invention also provides a method comprising: (a) obtaining a test sample comprising circulating tumor cells from a subject, and (b) determining CDK12 level in the test sample, wherein the subject suffers from HER2-positive cancer.

The (b) determination is conducted using a method selected from the group consisting of fluorescence in situ hybridization (FISH), a comparative genomic hybridization (CGH)-based array, a single nucleotide polymorphism array (a SNP array), sequence assembly comparison, paired-end sequencing, a multiplex ligation dependent probe amplification (MLPA) method, a multiplex amplifiable probe hybridization (MAPH) method, quantitative multiplex PCR of short fluorescent fragments (QMPSF), a microsatellite genotyping method, Southern blotting, immunohistochemistry (IHC), a polymerase chain reaction (PCR), a quantitative polymerase chain reaction (qPCR), a quantitative real-time polymerase chain reaction (qRT-PCR), a real-time polymerase chain reaction (real-time PCR), microarray-based comparative genomic hybridization, and a ligase chain reaction (LCR).

The (b) determining CDK12 level comprises one or more of the following (i)-(iii):
(i) determining a copy number of CDK12 genes in the test sample; (ii) determining an expression level of CDK12 proteins in the test sample; and (iii) determining an expression level of CDK12 mRNAs in the test sample.

The test sample comprises a tissue sample or blood sample.

The test sample may be a breast tissue sample or peripheral blood sample.

The present invention also provides a method of selecting a treatment for a subject suffering from a HER2 positive cancer, the method comprising the steps of:
(a) providing a test sample from the subject; (b) determining a CDK12 level in the test sample; (c) comparing the CDK12 level in the test sample against a control sample free of Her2 positive cancer, thereby determining the presence or absence of an increase in the CDK12 level in the test sample, and (d) if an increase of the CDK12 level of the test sample is present, administering a CDK12 inhibitor to the subject.

The (b) determining CDK12 level comprises one or more of the following (i)-(iii):
(i) determining a copy number of CDK12 genes in the test sample; (ii) determining an expression level of CDK12 proteins in the test sample; and (iii) determining an expression level of CDK12 mRNAs in the test sample.

The test sample comprises a tissue sample or blood sample.

The test sample may be a breast tissue sample or peripheral blood sample.

The (b) determining CDK12 level is conducted using a method selected from the group consisting of fluorescence in situ hybridization (FISH), a comparative genomic hybridization (CGH)-based array, a single nucleotide polymorphism array (a SNP array), sequence assembly comparison, paired-end sequencing, a multiplex ligation dependent probe amplification (MLPA) method, a multiplex amplifiable probe hybridization (MAPH) method, quantitative multiplex PCR of short fluorescent fragments (QMPSF), a microsatellite genotyping method, Southern blotting, immunohistochemistry (IHC), a polymerase chain reaction (PCR), a quantitative polymerase chain reaction (qPCR), a quantitative real-time polymerase chain reaction (qRT-PCR), a real-time polymerase chain reaction (real-time PCR), microarray-based comparative genomic hybridization, and a ligase chain reaction (LCR).

The CDK12 inhibitor of step (d) comprises one or more selected from the group consisting of an antisense nucleotide, small interfering RNA (siRNA), short hairpin RNA (shRNA), a peptide, a peptide mimetic, an aptamer, and an antibody, which complementarily or specifically bind to CDK12, or comprises one or more selected from the group consisting of dinaciclib and THZ-531.

The cancer is HER2-positive breast cancer.

The subject is being treated with a HER2 targeted therapeutic agent; is expected to have drug resistance to the HER2 targeted therapeutic agent; or has drug resistance to the HER2 targeted therapeutic agent.

The HER2 targeted therapeutic agent is selected from the group consisting of trastuzumab, pertuzumab, and trastuzumab emtansine (T-DM1).

The (i) determining a copy number of CDK12 genes in the tissue sample is performed by fluorescent in situ hybridization (FISH).

The determining CDK12 level in the tissue sample or blood sample is performed with a sense primer, an antisense primer, an antibody, an aptamer, or a probe which is complementary or specifically binds CDK12.

The FISH is performed with a nucleic acid probe that is fluorescently labeled.

The CDK12 gene has the sequence of SEQ ID NO: 3.

The present invention also provides a method of providing information for selecting a treatment for a subject suffering from a HER2 positive cancer, the method comprising the steps of:
a) providing a test sample from the subject; b) determining a CDK12 level in the test sample; c) comparing the CDK12 level in the test sample against a control sample free of HER2 positive cancer, thereby determining the presence or absence of an increase in the CDK12 level in the test sample, wherein the presence of the CDK12 level increase is associated with one or more of the following (i)-(v):
need for a CDK12 inhibitor treatment; tolerance against a HER2 targeted therapeutic agent; low sensitivity to a HER2 targeted therapeutic agent; poor treatment outcome with a HER2 targeted therapeutic agent; and need for co-administration of a HER2 targeted therapeutic agent and a CDK12 inhibitor.

The cancer is a breast cancer.

The present invention also provides a treatment method for a HER2 positive cancer, the method comprising the steps of:
(a) providing a test sample from the subject suffering from a HER2 positive cancer; (b) determining a CDK12 level in the test sample; (c) comparing the CDK12 level in the test sample against a control sample free of HER2 positive cancer, thereby determining the presence or absence of an increase in the CDK12 level in the test sample, (d) if an increase of the CDK12 level of the test sample is present, administering a CDK12 inhibitor to the subject, wherein the subject suffering from the HER2 positive cancer is being treated with a HER2 targeted therapeutic agent; is expected to have drug resistance to the HER2 targeted therapeutic agent; or has drug resistance to the HER2 targeted therapeutic agent, and wherein the (b) determining CDK12 level comprises one or more of the following (i)-(iii):
(i) determining a copy number of CDK12 genes in the test sample (ii) determining an expression level of CDK12 proteins in the test sample; and (iii) determining an expression level of CDK12 mRNAs in the test sample.

The test sample comprises a tissue sample or blood sample.

The test sample may be a breast tissue sample or peripheral blood sample.

The subject suffering from a HER2 positive cancer may be sensitive to the HER2 targeted therapeutic agent; or resistant to the HER2 targeted therapeutic agent.

In the step of (d), if an increase of the CDK12 level of the test sample is present, administering a CDK12 inhibitor along with HER2 targeted therapeutic agents to the subject, The (b) determining CDK12 level is conducted using a method selected from the group consisting of fluorescence in situ hybridization (FISH), a comparative genomic hybridization (CGH)-based array, a single nucleotide polymorphism array (a SNP array), sequence assembly comparison, paired-end sequencing, a multiplex ligation dependent probe amplification (MLPA) method, a multiplex amplifiable probe hybridization (MAPH) method, quantitative multiplex PCR of short fluorescent fragments (QMPSF), a microsatellite genotyping method, Southern blotting, immunohistochemistry (IHC), a polymerase chain reaction (PCR), a quantitative polymerase chain reaction (qPCR), a quantitative real-time polymerase chain reaction (qRT-PCR), a real-time polymerase chain reaction (real-time PCR), microarray-based comparative genomic hybridization, and a ligase chain reaction (LCR).

The CDK12 inhibitor of step (d) comprises one or more selected from the group consisting of an antisense nucleotide, small interfering RNA (siRNA), short hairpin RNA (shRNA), a peptide, a peptide mimetic, an aptamer, and an antibody, which complementarily or specifically bind to CDK12, or comprises one or more selected from the group consisting of dinaciclib and THZ-531.

The HER2 targeted therapeutic agent is selected from the group consisting of trastuzumab, pertuzumab, and trastuzumab emtansine (T-DM1).

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIG. 1 is a forest plot showing a hazard ratio of genes in 17q12 amplicons according to disease-free survival rates (DFSs: the right upper panel) and overall survival rates (OSs: the right lower panel) of breast cancer patients. The genes positioned for HER2 amplification are described according to a hazard ratio level thereof (all P values<0.01). The left bar graph represents HER2 co-amplification percentages of given genes.

FIG. 2 is a scatter plot showing the correlation between CDK12 expression and a copy number alteration (CNA) in METABRIC (Left). An r value was calculated using a Pearson's correlation coefficient. A box plot shows levels of CDK12 mRNA in given subtypes of METABRIC (Right). The P-value was calculated by one-way ANOVA using a post-hoc LSD test.

FIGS. 3A and 3B show the results of survival analysis of breast cancer patients according to CDK12 expression in METABRIC (3A) and a KM plotter (3B) using a Kaplan-Meier method together with a log-rank test.

FIGS. 4A and 4B show the results of measuring cell viability of trastuzumab-sensitive BT474 cells and trastuzumab-resistant HCC-1954 cells, which are treated with 1 μg/mL or 100 μg/mL trastuzumab (Trz); and/or 5 nM or 10 nM dinaciclib (Dina), using SRB analysis. Data is expressed as the mean±standard deviation (S.D.) (n=3). The P-value was calculated by RM ANOVA using a post-hoc LSD test.

FIGS. 5A and 5B show the results of analyzing an effect of CDK12 deficiency on trastuzumab responsiveness in in vivo HER2+ breast cancer. Given HER2+ breast cancer cells were orthotopically transplanted into mice, and the mice were treated with 20 mg/kg trastuzumab and/or 20 mg/kg dinaciclib. A growth curve of each group was analyzed twice for 5 to 6 weeks (n=8 per group; mean±SEM; RM ANOVA using a post-hoc LSD test). The panel is an image of a tumor obtained from the BT474 or HCC-1954 cells treated with trastuzumab and/or dinaciclib after orthotopic transplantation;

FIG. 6 is a heat map showing changes (≥1.5-fold) in gene expression between the control (CON) and CDK12-overexpressing ZR-75-30 cells (CDK12) obtained from RNA-seq analysis.

FIG. 7 shows the results of GSEA analysis showing the correlation of gene expression profiles between the control and CDK12-overexpressing cells based on the RNA-seq results.

FIG. 8 shows CDK12-target genes identified by the RNA-seq verified using qRT-PCR analysis in the CDK12-overexpressing ZR-75-30 cells. Data is expressed as the mean±S.D. of values measured in triplicate. The P-value was calculated using a double Student's t test.

FIG. 9 is a Venn diagram for comparing the number of dinaciclib-target genes (GSE88822[24]) and the number of general genes obtained from PolII ChIP-seq results (GSE72023[30]) and RNA-seq results.

FIGS. 10A and 10B show the results of determining an effect of inhibition of CDK12 kinases on the expression of WNT1, WNT3, and IRS1. Cells were treated with various doses of dinaciclib for 12 hours, and the expression of candidate targets of CDK12 was analyzed by immunoblotting and qRT-PCR (n=3, mean±S.D., ANOVA using a post-hoc LSD test).

FIGS. 11A and 11B show the results of ChIP-qPCR analysis showing the fold enrichment of given proteins and histone H3 acetylation in the TSS of IRS1, WNT1, and WNT3. Data is expressed as the mean±S.D. of values measured in triplicate. The P-value was calculated using a double Student's t test;

FIGS. 12A and 12B show the results of FACS analysis of percentages of CD44+/CD24−/ESA+ breast CSC-like populations in CDK12-overexpressing ZR-75-30 cells and CDK12-siRNA-injected BT474 cells. Data is expressed as the mean±S.D. of samples measured in triplicate. The P-value is based on a one-way ANOVA using double Student's t test (ZR-75-30 cells; left) and a post-hoc LSD test (BT474 cells; right).

FIGS. 13A and 13B are graphs of analyzing the self-renewal of CSCs in each of the given stable cell lines. Primary (P1) and secondary (P2) tumorsphere cells (diameter: ≥100 μm) were counted after 3 days, 5 days, and 7 days. The results are expressed as the mean±S.D. (n=3). The P-value was calculated based on ANOVA using a double Student's t test (Left panel) or a post-hoc LSD test (Right panel).

FIG. 14 shows Western blot and qRT-PCR results (n=3, mean±S.D.; double Student's t test) showing a phosphorylation level of GSK-31β and WNT1 and WNT3 expression in each of the given cell lines.

FIGS. 15A, 15B, 16A and 16B show the results of analyzing the intracellular localization of β-catenin in the given stable cell lines using cell fractionation (FIGS. 15A and 15B) and immunofluorescence staining (FIGS. 16A and 16B). Nuclear translocation of β-catenin in the control, a CDK12-overexpressing cell line and a CDK12-knockdown stable cell line was quantified by counting cells having β-catenin nuclei from an immunofluorescence image. Data is expressed as the mean±S.D. of values measured in triplicate. The P-value was calculated by a double Student's t assay. M+C: Membrane and cytoplasmic β-catenin; N: Nuclear β-catenin.

FIGS. 17A and 17B show the results of luciferase-reporter analysis of measuring the TCF/lymphoid enhancer-binding factor-promoter activities in the given cell lines. TOP: pTOP-flash (a wild-type TCF-binding site), FOP: pFOP-flash (a variant TCF-binding site). Data is expressed as the mean±S.D. of values measured in triplicate. The P-value was calculated by a double Student's t assay.

FIG. 18 shows the results of qRT-PCR analysis showing mRNA levels of WNT/β-catenin/TCF-target genes in the CDK12-overexpressing ZR-75-30 cells. Mean+S.D. (n=3). The P-value was calculated by a double Student's t assay;

FIG. 19 shows the results of a human phospho-RTK array showing that phosphokinase-associated proteins are activated in CDK12-knockdown BT474 cells. A bar graph shows a fold change in intensity of spots.

FIG. 20 shows immunoblotting results showing levels of given proteins in a HER2+ breast cancer in which CDK12 is stably expressed or CDK12 is knocked down.

FIG. 21 shows the results of Western blot and qRT-PCR analyses showing a phosphorylation level and expression of IRS1 in each of the given cell lines. Mean+S.D. (n=3). The P-value was calculated by a double Student's t assay.

FIGS. 22 and 23 show immunoprecipitation and immunoblotting results using an antibody against a cell lysate from the CDK12-overexpressing ZR-75-30 cells.

FIG. 24 shows a proposed model for a regulatory mechanism of CDK12 regulating cancer sternness, cell growth and trastuzumab responsiveness in HER2+ breast cancer;

FIG. 25 is an OncoPrint view showing the percentages of HER2 and CDK12 which are associated with genetic alterations of HER2 and CDK12 in METABRIC and TCGA.

FIG. 26 shows a box plot showing CDK12 mRNA levels in each subtype of breast cancers from TCGA (Left) (the P-value was calculated by one-way ANOVA using a post-hoc LSD test), and shows a degree of dispersion showing the correlation between CDK12 mRNA levels and copy number in TCGA (Right). The r value was calculated using a Pearson's correlation coefficient.

FIG. 27 shows the correlation between CDK12 and HER2 expression in METABRIC and TCGA. The r value was calculated using a Pearson's correlation coefficient.

FIG. 28 is a forest plot (Upper panel) showing the relationship between the CDK12 expression and metastatic relapse (MR) risk in various types of breast cancer data sets produced using bc-GenExMiner 4.0 (bcgenex.centregaudu-cheau.fr), and shows NPI and AOL prognostic index-adjusted analysis results (Lower panel).

FIG. 29 is an OncoPrint view (Upper panel) showing an amplification status and an mRNA level of CDK12 in HER2+ and HER2-breast cancer cells obtained from the Cancer Cell Line Encyclopedia (CCLE). In each of the cell lines, a level of a CDK12 protein was confirmed by Western blot (Lower panel);

FIGS. 30A, 30B, 30C and 30D are a growth curve of each of the cell lines measured using SRB analysis. Mean+S.D. (n=3). The P-value was calculated by RM ANOVA using a post-hoc LSD test.

FIGS. 31A and 31B show the results of analyzing an effect of CDK12 on in vivo tumor growth in an orthotopic tumor xenograft model. Each of the cells lines was injected into NOD/SCID mice after transplantation using a 17-13 estradiol pellet. Tumor size was measured twice a week, and then analyzed from a tumor growth curve (n=7/group; mean±S.E.M). The P-value was calculated by RM ANOVA using a post-hoc LSD test;

FIGS. 32A, 32B, 32C and 32D show the cell viability measured by SRB analysis after the cells are treated with a varying volume (g/mL) of trastuzumab (Trz) or a vehicle for 5 days. Data is expressed as the mean±S.D. (n=3). The P-value was calculated by RM ANOVA using a post-hoc LSD test.

FIGS. 33A, 33B, 33C and 33D show the results of determining the cell growth of each of the stable cell lines measured by SRB analysis after the cells are treated with trastuzumab (Trz) or a vehicle for 5 days. Each of trastuzumab-sensitive HER2+ breast cancer cell lines (e.g., ZR-75-30 cells and BT474 cells); and trastuzumab-resistant HER2+ breast cancer cell lines (e.g., HCC-1419 cells and HCC-1954 cells) was treated with 1 μg/mL or 100 μg/mL trastuzumab. Data is expressed as the mean±S.D. (n=3). The P-value was calculated by RM ANOVA using a post-hoc LSD test.

FIGS. 35A and 35B show the percentages of breast CSCs (CD44+/CD24−/ESA+) in each of the given stable cell lines, as measured by flow cytometry. Data is expressed as the mean±S.D. (n=3). The P-value was calculated by ANOVA using a double Student's t assay (Left panel) or a post-hoc LSD test (Right panel).

FIGS. 36A and 36B show the results of tumorsphere-formation analysis of each of the cell lines. Primary (P1) and secondary (P2) tumorsphere cells (diameter: ≥100 μm) were counted after 3 days, 5 days, and 7 days. Data is expressed as the mean±S.D. (n=3). The P-value was calculated by ANOVA using a double Student's t test (Left panel) or a post-hoc LSD test (Right panel).

DETAILED DESCRIPTION OF EXEMPLARY EMBODIMENTS

Hereinafter, exemplary embodiments of the present invention will be described in detail. However, the present invention is not limited to the embodiments disclosed below and can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

The present invention relates to a companion diagnostic composition for human epidermal growth factor receptor 2 (HER2)-targeted therapy in HER2-positive cancer. Specifically, the present invention provides a companion diagnostic composition for HER2-targeted therapy in HER2-positive cancer, which includes an agent for measuring a CDK12 level.

Figure 24:
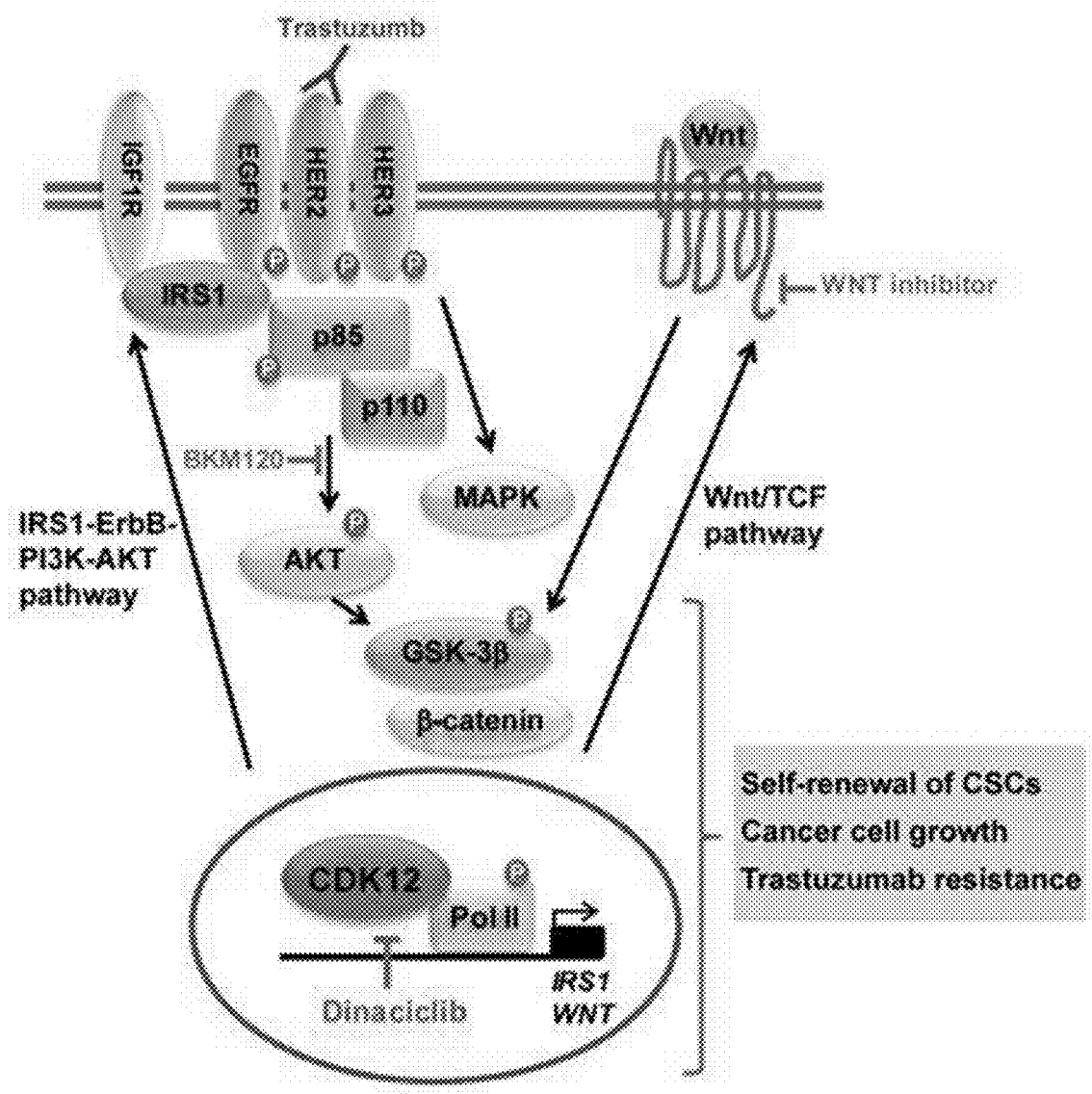

Information on a gene, mRNA and a protein of CDK12 is available from the National Center for Biotechnology Information (NCBI). For example, NM_016507.3, NM_015083.2, NP_057591.2, NP_055898.1, or the like has been registered as a NCBI Reference Sequence, which includes all types of sequence information known as CDK12 in addition to the genomic information. According to one embodiment of the present invention, CDK12 activates a WNT-ligand-mediated WNT/β-catenin/TCF-signaling pathway and promotes an ErbB-signaling network in a manner dependent on the activity of a CDK12 kinase targeting PolII CTD, thereby maintaining CSC-like traits (FIG. 24).

According to another embodiment, an essential role of co-amplification of HER2 and CDK12 was confirmed in Chr17q1 causing HER2+ breast cancer. HER2 is a well-known carcinogenic factor in HER2+ breast cancer, but various genes co-amplified with HER2 may have an influence on the response to anti-HER2 therapy by co-suppressing these genes that enhance a growth inhibitory effect and promote induction of apoptosis in HER2+ breast cancer. Consistent with these results, HER2 amplicons include various genes closely associated with HER2 treatment outcomes, and thus serve to further enhance the aggressiveness of HER2+ breast cancer. As a result, it was confirmed that CDK12 is a carcinogenic factor because it is co-amplified with HER2. Also, because it was confirmed that CDK12 is a promising target in HER2+ breast cancer, it was found that patients may be selected for HER2-targeted therapy, based on CDK12 amplification or expression statuses.

According to one embodiment of the present invention, it was confirmed that, when CDK12 gene amplification occurs or a CDK12 mRNA and CDK12 protein is overexpressed in a subject having HER2-positive breast cancer, CDK12 has resistance to a HER2-targeted therapeutic agent (i.e., trastuzumab). Also, it was confirmed that, when amplification or overexpression of CDK12 is inhibited or a cell line is treated with a CDK12 kinase inhibitor, the resistance of CDK12 to trastuzumab is improved and a therapeutic effect of trastuzumab is improved.

According to another embodiment, it was confirmed that the clinical significance of CDK12 expression is similar to that of HER2 in the survival analysis of breast cancer patients. It was found that CDK12 may be a promising therapeutic target as one subtype in the HER2-positive breast cancer because this inhibition of CDK12 by dinaciclib is confirmed to have a remarkable anti-tumor effect in trastuzumab-sensitive and -resistant HER2+ breast cancers.

Therefore, the companion diagnostic composition of the present invention has a use as a marker intended to provide information on the need for administration of a HER2-targeted therapeutic agent; the need for administration of a CDK12 inhibitor; the probability of expressing drug resistance to the HER2-targeted therapeutic agent; sensitivity to the HER2-targeted therapeutic agent; prediction of a treatment outcome with the HER2-targeted therapeutic agent; or the need for co-administration of the HER2-targeted therapeutic agent and the CDK12 inhibitor.

In this respect, the present invention relates to a method comprising: (a) obtaining a test sample from a subject suffering from HER2-positive cancer, and (b) determining CDK12 level in the breast tissue sample or peripheral blood sample, Further, the present invention relates to a method of selecting a treatment for a subject suffering from a HER2 positive cancer, the method comprising the steps of: (a) providing a test sample from the subject; (b) determining a CDK12 level in the test sample; (c) comparing the CDK12 level in the test sample against a control sample free of Her2 positive cancer, thereby determining the presence or absence of an increase in the CDK12 level in the test sample, and (d)

if an increase of the CDK12 level of the test sample is present, administering a CDK12 inhibitor to the subject.

In the present invention, when reference is made to the term "CDK12," it is interpreted to refer to all a CDK12 gene, mRNA of the CDK12 gene, or a CDK12 protein. Also, the CDK12 gene, the CDK12 mRNA, or the CDK12 protein is interpreted to encompass their fragments or recombinant proteins, codon-optimized cDNAs, and the like, which have substantially the same activities as the CDK12 gene, the CDK12 mRNA, or the CDK12 protein. Therefore, in the present invention, an expression level of CDK12 is meant to include an expression level of a CDK12 gene or mRNA thereof, or a CDK12 protein expressed therefrom. Also, each of the names of genes mentioned in the present invention is also interpreted to encompass all types of a gene, mRNA, or a protein thereof.

In the present invention, the term "companion diagnostics" refers to one of the diagnostic tests for checking the possibility of applying a certain therapeutic drug to certain patients. In the present invention, a copy number of a CDK12 gene, an expression level of CDK12 mRNA, or an expression level of a protein expressed from the CDK12 mRNA in a subject suffering from a human epidermal growth factor receptor 2 (HER2)-positive cancer may be measured as a companion diagnostic marker to check the possibility of applying a HER2-targeted therapeutic agent; and/or a CDK12 inhibitor to the subject suffering from the HER2-positive cancer.

Therefore, according to this aspect, the companion diagnostics in the present invention may be intended to provide information on the need for administration of a HER2-targeted therapeutic agent; the need for administration of a CDK12 inhibitor; the probability of expressing drug resistance to the HER2-targeted therapeutic agent; sensitivity to the HER2-targeted therapeutic agent; prediction of a treatment outcome with the HER2-targeted therapeutic agent; or the need for co-administration of the HER2-targeted therapeutic agent and the CDK12 inhibitor.

In the present invention, the term "discrimination" means that an object is distinguished according to certain criteria. In the present invention, the term may be used for the purpose of distinguishing whether or not a subject, who has been diagnosed with or is at risk for a human epidermal growth factor receptor 2 (HER2)-positive cancer, has drug resistance to the HER2-targeted therapeutic agent, or distinguishing whether or not the subject has sensitivity to the HER2-targeted therapeutic agent.

Also, in the present invention, the expression "need for administration" is intended to determine whether or not to administer the therapeutic agent to a subject who may have or be expected to have a therapeutic effect of a therapeutic agent (a drug). In this case, the determination may be performed using a method of measuring a copy number or an expression level of the companion diagnostic marker according to the present invention and comparing the copy number or the expression level of the companion diagnostic marker with a reference value.

In the present invention, the copy number of the CDK12 gene, an expression level of CDK12 mRNA, or an expression level of the CDK12 protein may be measured as the companion diagnostic marker to check whether the HER2-targeted therapeutic agent; or the CDK12 inhibitor is administered or the HER2-targeted therapeutic agent and the CDK12 inhibitor are co-administered.

In the present invention, the term "human epidermal growth factor receptor 2-positive cancer" or "HER2-positive cancer" refer to a cancer showing amplification or overexpression of the HER2 gene. The HER2-positive cancer may be selected from the group consisting of breast cancer, gastric cancer, lung cancer, esophageal carcinoma, bladder cancer, and colon cancer, all of which are HER2-positive, but the present invention is not limited thereto. Most preferably, the HER2-positive cancer may be HER2-positive breast cancer. The HER2-positivity (gene amplification or overexpression) may be determined according to the criteria typically used in the technical field of the present invention, and thus may vary depending on the clinical criteria used to diagnose the HER2-positivity in each country. HER2-targeted therapies are used as the most representative therapies for HER2-positive cancer. Among these, trastuzumab, which is an anti-HER2 monoclonal antibody, is a drug that has been most widely used as a standard regimen for HER2+ breast cancer patients. However, the accumulated clinical evidence reveals that the response of HER2+ breast cancers to trastuzumab therapy varies, with 50% or more of patients having no response to or acquiring resistance to trastuzumab. Therefore, there is a need for development of a companion diagnostic marker capable of more precisely distinguishing between patient groups for use the HER2-targeted therapeutic agent and development of a therapy capable of overcoming the resistance shown in anti-HER2 therapy and improving a therapeutic effect.

In the present invention, the HER2-targeted therapeutic agent may be any therapeutic agent targeting HER2 as a therapeutic target. In this case, the HER2-targeted therapeutic agent may be selected from the group consisting of trastuzumab, pertuzumab, and trastuzumab emtansine (T-DM1), but the present invention is not limited thereto.

The companion diagnostic composition of the present invention is characterized in that it includes an agent for measuring a CDK12 level. In the present invention, the copy number of CDK12 refers to a copy number of a CDK12 gene, and the expression level of CDK12 refers to an expression level of CDK12 mRNA; or an expression level of a CDK12 protein.

In the present invention, the term "copy number of a gene" refers to the number of a certain gene in a certain genotype of each subject, that is, the number of a certain gene or gene fragments formed by multiple duplications. In the present invention, measurement of the copy number of the gene may be interpreted to be the same as measurement of a copy number variation (or a copy number variant; CNV) and a gene copy number (GCN) commonly used in the related art. Also, the copy number of the gene may represent that there is "amplification of the gene" when the copy number is not less than or greater than a predetermined reference value, and may represent that there is no "amplification of the gene" when the copy number is less than predetermined reference value. In the present invention, the "amplification of the gene" may be used interchangeably with the "duplication of the gene," and means that the gene copy number is not less than or greater than the reference value.

According to one embodiment of the present invention, when it is assumed that the gene copy number of CDK12, which has a ratio of 2.2 with respect to CEP17 (chromosome 17) in the subject suffering from HER2-positive breast cancer, as determined by FISH analysis, is set as a reference value, amplification of a gene is set when the gene copy number is greater than the reference value, and then, analyzed. However, because this is a value set to determine the relationship between the amplification or overexpression of CDDK12 and the resistance to the HER2-targeted therapeutic agent in the ER-positive breast cancer according to the present invention, the amplification reference value may be differently set depending on the development process such as validation of a kit, a composition, a detection method, or the like using CDK12 as a biomarker.

In the present invention, the term "mRNA expression level" or "protein expression level" refers to a level of expression of messenger RNA that delivers genetic information of a certain gene to the ribosomes, or a level of a protein expressed from the messenger RNA. The expression level of the mRNA or protein may be represented by "overexpression" when the expression level is not less than or greater than a certain reference value.

According to one embodiment of the present invention, the quantile normalization log 2 intensity obtained through a microarray, which is greater than or equal to 8, is set as an overexpression reference value, and then analyzed. However, because this is a value set to determine the relationship between the amplification or overexpression of CDDK12 and the resistance to the HER2-targeted therapeutic agent in the ER-positive breast cancer according to the present invention, the overexpression reference value may be differently set depending on the development process such as validation of a kit, a composition, a detection method, or the like using CDK12 as a biomarker.

In the present invention, the term "agent for measuring a copy number of a gene" or "agent for measuring an mRNA expression level" may be one selected from the group consisting of a sense primer, an antisense primer, and a probe, all of which bind complementarily to the gene or mRNA thereof, but the present invention is not limited thereto.

In the present invention, the term "primer" refers to a nucleic acid sequence that has a short free 3'-terminal hydroxyl group, that is, a short nucleic acid sequence that may form a base pair with a complementary template and serves as an initiation point for replication of a template strand. The primer may initiate DNA synthesis in the presence of a reagent (a DNA polymerase or a reverse transcriptase) for a polymerization reaction at a proper temperature in a proper buffer solution, and four different deoxynuleoside triphosphates (dNTPs). In the present invention, the primer may be a primer that may specifically bind to a CDK12 gene, and may preferably consist of sense (forward) and antisense (reverse) nucleic acid sequences having 7 to 50 nucleotides. The primer may incorporate additional features which do not change basic properties of a primer serving as an initiation site for DNA synthesis. Also, the nucleic acid sequence of the primer of the present invention may include a label that is directly or indirectly detectable by spectroscopic, photochemical, biochemical, immunochemical, or chemical means, when necessary.

According to one embodiment, the primer may be a sense and/or antisense primer complementary to the CDK12 gene or mRNA thereof. The sense or antisense primer may be included alone, or may be included together with another sense and antisense primer. Also, the sense or antisense primer may be a probe that may specifically bind to CDK12.

In the present invention, the term "probe" refers to a nucleic acid fragment (e.g., RNA or DNA) that corresponds to a few bases to several hundreds of bases, which may specifically bind to a certain nucleotide sequence. Because the nucleic acid fragment is labeled, it includes the form of an oligonucleotide probe, a single-stranded DNA probe, a double-stranded DNA probe, a RNA probe, or the like, which may check the presence of a certain gene or mRNA. The primer or probe of the present invention may be chemically synthesized using methods known in the art.

In the present invention, all conventional methods used in the technical field of the present invention may be used as the "method of measuring a gene copy number." More specifically, a whole-genome analysis method and a target-specific method may be all used. Specifically, a method selected from the group consisting of fluorescence in situ hybridization (FISH), a comparative genomic hybridization (CGH)-based array, a single nucleotide polymorphism (SNP) array, sequence assembly comparison, paired-end sequencing, a multiplex ligation dependent probe amplification (MLPA) method, a multiplex amplifiable probe hybridization (MAPH) method, quantitative multiplex PCR of short fluorescent fragments (QMPSF), a microsatellite genotyping method, Southern Blotting, immunohistochemistry (IHC), a polymerase chain reaction (PCR), a quantitative polymerase chain reaction (qPCR), a quantitative real-time polymerase chain reaction (qRT-PCR), a real-time polymerase chain reaction (real-time PCR), microarray-based comparative genomic hybridization, and a ligase chain reaction (LCR), but the present invention is not limited thereto.

In the present invention, all conventional methods used in the technical field of the present invention may be used as the "method of measuring an mRNA expression level." More specifically, a polymerase chain reaction (PCR), a reverse transcription polymerase chain reaction (RT-PCR), a competitive reverse transcription polymerase chain reaction (competitive RT-PCR), a real-time reverse transcription polymerase chain reaction (real-time RT-PCR), an RNase protection assay (RPA), Northern blotting, RNA-sequencing (RNA-seq), nanostrings, DNA chips, or the like may be used, but the present invention is not limited thereto. The detection methods may be used to check whether mRNA is overexpressed or underexpressed by comparing an mRNA expression level in a biological sample obtained from a subject requiring companion diagnostics with an mRNA expression level in a control sample, check whether mRNA is overexpressed or underexpressed by measuring an mRNA expression value of the sample and comparing the mRNA expression value of the sample with the reference value, or check whether mRNA expression increases or decreases by comparing an mRNA expression level of CDK12 after treatment with a HER2-targeted therapeutic agent and an mRNA expression level of CDK12 before treatment with the HER2 therapeutic agent to see if the mRNA expression level of CDK12 after treatment with a HER2-targeted therapeutic agent is lower than that of CDK12 before treatment with the HER2 therapeutic agent.

In the present invention, the "agent for measuring a protein level" may be selected from the group consisting of an antibody, an aptamer, and a probe, all of which bind complementarily to the protein, but the present invention is not limited thereto. In the present invention, the agent may be selected from the group consisting of an antibody, an aptamer, and a probe, all of which bind complementarily to the CDK12 protein.

Also, in the present invention, all conventional methods used in the technical field of the present invention may be used as the "method of measuring a protein expression level." More specifically, a protein chip assay, immunoassay, a ligand-binding assay, a matrix-assisted laser desorption/ionization time of flight mass spectrometry (MALDI-TOF) assay, a surface-enhanced laser desorption/ionization time of flight mass spectrometry (SELDI-TOF) assay, a radioimmunoassay, a radioimmunodiffusion assay, an Ouchterlony immunodiffusion assay, rocket immunoelectrophoresis, immunohistochemical staining (IHC), a complement fixation assay, a 2D electrophoresis assay, liquid chromatography-mass spectrometry (LC-MS), liquid chromatography-mass spectrometry/mass spectrometry (LC-MS/MS), Western blot, or an enzyme-linked immunosorbent assay (ELISA) may be used, but the present invention is not limited thereto.

In the present invention, the term "resistance" refers to tolerance, and means that cells do not significantly show a cellular or biological response to certain drugs. Specifically, the term means that cell death does not occur and the apoptosis of cancer cells is reduced when the cancer cells are treated with a drug.

In the present invention, the term "HER2-targeted therapeutic agent" refers to a "HER2 gene, mRNA, or protein inhibitor," and is intended to encompass all types of anti-HER2 therapeutic agents, as an agent, that specifically act on a human epidermal growth factor receptor 2 (HER2) gene or protein to suppress or inhibit the expression or activity of the HER2 gene or protein inhibitor. Specifically, the HER2-targeted therapeutic agent may serve to suppress dimerization of HER2 or suppress signals generated when HER2 interacts with other receptors.

The HER2 expression inhibitor may include one or more selected from the group consisting of an antisense nucleotide, small interfering RNA (siRNA), and short hairpin RNA (shRNA), all of which bind complementarily to mRNA of the gene.

The HER2 protein activity inhibitor may include one or more selected from the group consisting of a natural or synthetic compound, a peptide, a peptide mimetic, an aptamer, and an antibody, all of which specifically bind to the protein.

The HER2-targeted therapeutic agent refers to a therapeutic agent targeting the HER-2 receptor, and may, for example, be an antibody-based therapeutic agent. In addition to the commercially available drugs, any therapeutic agents may belong to the category of HER2-targeted therapeutic agents as long as the therapeutic agent targets a HER-2 receptor, which is a target already known in articles or patents, as a therapeutic target.

Specifically, the therapeutic agent targeting the HER-2 receptor may be selected from the group consisting of trastuzumab, pertuzumab, and trastuzumab emtansine (T-DM1), but the present invention is not limited thereto.

The trastuzumab is also referred to as Herceptin. The trastuzumab is a therapeutic agent for metastatic cancer, which develops when the human epidermal growth factor receptor HER-2 gene or gene products thereof are overexpressed, that is, an antibody-based therapeutic agent recognizing an extracellular portion of HER2 as an antigen determinant (i.e., an epitope).

The pertuzumab is an anti-HER2 therapeutic agent against metastatic diseases, and is commercially available under the brand name of Perjeta, and the like. The pertuzumab serves to hinder signal transduction of HER-2 to suppress HER2 dimerization. The pertuzumab may be co-administered with trastuzumab or docetaxel.

The T-DM1 (trastuzumab emtansine) is also referred to as ado-trastuzumab emtansine, and is a therapeutic agent in the form of an antibody-drug conjugate commercially available under the brand name of Kadcyla. The T-DM1 has a structure in which trastuzumab is bound to emtansine (DM1) which is a cytotoxic agent.

In the present invention, the term "subject" or "patient" may refer to a vertebrate, and specifically to a mammal. In this case, the mammal may include all types of a dog, a horse, a cat, cattle, a primate, a mouse, and a rat. According to preferred embodiments, the mammal may be a human.

Also, the present invention provides a method of providing companion diagnostic information on a HER2-targeted therapeutic agent in human epidermal growth factor receptor 2 (HER2)-positive cancer, which includes measuring a copy number or an expression level of CDK12 in a sample obtained from a subject suffering from the human epidermal growth factor receptor 2 (HER2)-positive cancer.

The method of providing companion diagnostic information on a HER2-targeted therapeutic agent in human epidermal growth factor receptor 2 (HER2)-positive cancer may be a method of providing information for selecting a treatment for a subject suffering from a HER2 positive cancer.

The method may comprise the steps of:
(a) providing a test sample from the patient subject; (b) determining a CDK12 level in the test sample; (c) comparing the CDK12 level in the test sample against a control sample free of breast HER2 positive cancer, thereby determining the presence or absence of an increase in the CDK12 level in the test sample.

The presence of the CDK12 level increase is associated with one or more of the following (i)-(v):
(i) need for a CDK12 inhibitor treatment;
(ii) tolerance against a HER2 targeted therapeutic agent;
(iii) low sensitivity to a HER2 targeted therapeutic agent;
(iv) poor treatment outcome with a HER2 targeted therapeutic agent; and
(v) need for co-administration of a HER2 targeted therapeutic agent and a CDK12 inhibitor.

The contents described above for the companion diagnostic composition may be applied mutatis mutandis to or used as they are for the method for providing companion diagnostic information according to the present invention.

The method for providing companion diagnostic information is intended to provide information on the need for administration of a HER2-targeted therapeutic agent; the need for administration of a CDK12 inhibitor; the probability of expressing drug resistance to the HER2-targeted therapeutic agent; sensitivity to the HER2-targeted therapeutic agent; prediction of a treatment outcome with the HER2-targeted therapeutic agent; or the need for co-administration of the HER2-targeted therapeutic agent and the CDK12 inhibitor.

The companion diagnostic method may further include providing information on the probability of one or more of the following applying to the subject who provided the sample when the results of measurement show that the copy number or the expression level of CDK12 in the sample is greater than a reference value:
the need for administration of the CDK12 inhibitor;
a high probability of expressing drug resistance to the HER2-targeted therapeutic agent;
low sensitivity to the HER2-targeted therapeutic agent;
a poor treatment outcome with the HER2-targeted therapeutic agent; or
the need for co-administration of the HER2-targeted therapeutic agent and the CDK12 inhibitor.

Based on the results of measurement, a subject showing CDK12 amplification, that is, a subject having a copy number of a CDK12 gene; an mRNA expression level of the CDK12 gene; or an expression level of a CDK12 protein higher than the reference value, may be classified as having low sensitivity to the HER2-targeted therapeutic agent or resistance to the therapeutic agent. Also, when the subject is a subject who receives the HER2-targeted therapeutic agent, the treatment outcome with the HER2-targeted therapeutic agent may be predicted to be poor, and the subject may be judged to have drug resistance to the administered HER2-targeted therapeutic agent. Therefore, the administration (or prescription) of the CDK12 inhibitor may be judged to be needed to increase the sensitivity to the HER2-targeted therapeutic agent or decrease the resistance to the HER2-targeted therapeutic agent in the subject, or the co-administration of the HER2-targeted therapeutic agent and the CDK12 inhibitor may be judged to have an anti-cancer therapeutic effect.

In the present invention, the term "reference value" refers to a value that serves as the standard for distinguishing between amplification and non-amplification of a gene; or overexpression and underexpression of an mRNA or protein. One example of the reference value may be an average gene copy number or an average mRNA/protein expression level in a subject before treatment with a certain drug, or an average gene copy number or an average mRNA/protein expression level in a normal subject, but the present invention is not limited thereto. Also, the reference value may be determined depending on the distribution of the average gene copy number or the distribution of the mRNA/protein expression level in a certain group of patients, but the present invention is not limited thereto.

Specifically, the gene copy number, the mRNA expression level, or the protein expression level may be obtained by measuring an average gene copy number, an mRNA expression level, or a protein expression level from a sample of each subject using a method of measuring a gene, mRNA, or protein level commonly used in the technical field of the present invention, and setting the measured values, which correspond to the top 1%, 2%, 3%, 4%, 5%, 6%, 7%, 8%, 9% 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% in a distribution of the measured values, as the reference value.

As one example, in the case of the gene copy number of CDK12, the reference value may be greater than or equal to 1, 2, 3, 4, 5, 6, 7, 8, 9, or 10 copies As previously described above, the reference value of the present invention may be set according to typical methods used in the technical field of the present invention, and may be set using software for obtaining various statistic methods and calculating statistics, and the like. In the present invention, the reference value may vary depending on the total number (n) of samples (or subjects), or may differ depending on a setup purpose. In this case, when a kit is manufactured using the CDK12 marker of the present invention, the reference value may vary depending on an optimization level of products, and the like. However, because the reference value may be set with reference to the present invention, all the reference values falls within the scope of the present invention. Also, the reference value of the present invention may be a predetermined value set according to conventional methods.

Also, the method may further include prescribing one or more selected from the group consisting of a CDK12 inhibitor and a HER2-targeted therapeutic agent for a subject classified into the CDK12 gene amplification or providing information to the subject.

In the present invention, the term "sample" may be urine, a body fluid (including blood, a lymphatic fluid, tissue fluid, or the like), or a tissue. Preferably, the blood sample may be a peripheral blood sample, or the peripheral blood sample comprising circulating tumor cells from a subject. The tissue sample may be a biopsy tissue sample, and the tissue sample may be a breast, bladder, pancreatic, ovarian, or stomach tissue sample. The sample may be obtained from a subject having cancer, and more preferably obtained from a subject who is suspected, judged or diagnosed to suffer from HER2-positive cancer.

In addition, the present invention provides a companion diagnostic kit or a companion diagnostic system for HER2-targeted therapy, which includes an agent for measuring a CDK12 level.

Description of the companion diagnostic composition or the method of proving companion diagnostic information is applicable mutatis mutandis to the companion diagnostic kit or the companion diagnostic system according to the present invention.

The kit or the system may further include an agent for measuring a copy number of a human epidermal growth factor receptor 2 (HER2) gene; an mRNA expression level of the HER2 gene; or an expression level of a HER2 protein. In this case, the companion diagnostic kit of the present invention may judge whether or not a sample from a subject is HER2-positive and whether the sample has resistance (or sensitivity) to the HER2-targeted therapeutic agent at the same time. The HER2-positivity of the sample may be judged according to a method known in the technical field of the present invention. For example, when the HER2-positivity is judged according to criteria disclosed for HER2-positive breast cancer [J Clin Oncol. 2007 Jan. 1; 25(1): 118-45. Epub 2006 Dec. 11; PMID: 17159189], the HER2 may be judged to be positive when the HER2 gene copy number is greater than 6. However, the HER2-positivity may vary depending on the type of HER2-positive cancer, and may be determined, if any, according to the methods and/or criteria separately determined in each country according to clinical criteria, but the present invention is not limited thereto.

The agent for measuring a gene copy number; an mRNA expression level; or a protein level is applicable mutatis mutandis to what is as described for CDK12 above in order to avoid redundant description.

The kit or the system may be intended to provide information on the need for administration of a HER2-targeted therapeutic agent; the need for administration of a CDK12 inhibitor; the probability of expressing drug resistance to the HER2-targeted therapeutic agent; sensitivity to the HER2-targeted therapeutic agent; prediction of a treatment outcome with the HER2-targeted therapeutic agent; or the need for co-administration of the HER2-targeted therapeutic agent and the CDK12 inhibitor.

The kit includes a diagnostic kit based on conventional quantitative analysis of a gene copy number, mRNA expression and protein expression, without limitation. For example, the kit may be an RT-PCR kit, a DNA chip kit, a protein kit, or an array kit. In addition to a pair of primers specific to the CDK12 gene and/or the HER2 gene, the RT-PCR kit may include a test tube or another proper container, a reaction buffer solution, deoxynucleotides (dNTPs), enzymes such as a Taq-polymerase and a reverse transcriptase, a DNase, an RNase inhibitor, sterilized water, and the like, which may be commonly included in a configuration of a kit. Also, conventional technology for companion diagnostic kits or systems is applicable mutatis mutandis to the present invention.

According to one embodiment, the prescription of the anti-HER2 therapeutic agent may be decided by determining whether or not HER2 is positive in a sample obtained from a cancer subject, and measuring a copy number of a CDK12 gene, an mRNA expression level of CDK12, or an expression/activity level of a CDK12 protein. Specifically, when the subject has a copy number and/or an expression level of the CDK12 gene higher than the reference value, the subject may be classified as having low sensitivity to the HER2-targeted therapeutic agent or resistance to the HER2-targeted therapeutic agent. Also, when the subject is a subject who receives the HER2-targeted therapeutic agent, the treatment outcome with the HER2-targeted therapeutic agent may be predicted to be poor, and the subject may be judged to have drug resistance to the administered HER2-targeted therapeutic agent. Therefore, the administration of the CDK12 inhibitor may be judged to be needed to increase the sensitivity to the HER2-targeted therapeutic agent or decrease the resistance to the HER2-targeted therapeutic agent in the subject, or the co-administration of the HER2-targeted therapeutic agent and the CDK12 inhibitor may be judged to have an anti-cancer therapeutic effect, or may be judged to be needed.

Also, the present invention provides an anti-cancer pharmaceutical composition for treating a subject having a human epidermal growth factor receptor 2 (HER2)-positive cancer, that is, a subject who has a copy number or an expression level of CDK12 higher than the reference value; or a subject who has or is expected to have drug resistance to the HER2-targeted therapeutic agent, wherein the anti-cancer pharmaceutical composition includes a CDK12 inhibitor as an active ingredient.

In addition, the present invention provides a pharmaceutical composition for suppressing or enhancing resistance to the HER2-targeted therapeutic agent in a subject having a human epidermal growth factor receptor 2 (HER2)-positive cancer, wherein the pharmaceutical composition includes a CDK12 inhibitor as an active ingredient.

Furthermore, the present invention provides a therapy adjuvant composition for HER2-targeted therapy in a subject having a human epidermal growth factor receptor 2 (HER2)-positive cancer, wherein the therapy adjuvant composition includes a CDK12 inhibitor as an active ingredient.

Description of the companion diagnostic composition, the method of providing companion diagnostic information, and the companion diagnostic kit as described above is applicable mutatis mutandis to the pharmaceutical composition; or the therapy adjuvant composition according to the present invention.

The pharmaceutical composition or the therapy adjuvant composition according to the present invention includes the CDK12 inhibitor as the active ingredient, and thus may suppress resistance to the HER2-targeted therapeutic agent in the subject, enhance drug sensitivity and an effect of the therapeutic agent, and improve a prognosis when the CDK12 inhibitor is administered to a subject having HER2-positive cancer and showing CDK12 amplification or overexpression, that is, a subject who has a copy number or an expression level of a CDK12 gene higher than the reference value; and/or a subject who has or is expected to have drug resistance to the HER2-targeted therapeutic agent, or the CDK12 inhibitor and the HER2-targeted therapeutic agent co-administered to the subject.

The anti-HER2 therapy is a therapy most commonly applied to HER2+ breast cancer patients, but has a persistent drawback in that more than half the HER2+ breast cancer patients do not respond to a representative drug such as trastuzumab or have resistance to trastuzumab. Also, the trastuzumab is an antibody-based therapeutic agent, and thus has problems in that it is very expensive compared to other anti-cancer drugs, and should be administered to patients for a long period of time. Therefore, there is still a need for a new therapeutic method capable of replacing the trastuzumab or improving a therapeutic effect of the trastuzumab.

The mechanism of action of trastuzumab and the mechanism of resistance to trastuzumab are still controversial, but the bypass of HER2 through ErbB receptor cross-talk, and the constitutive activation of downstream signaling cascades as main mechanisms associated with the resistance to trastuzumab should be dealt with. To overcome these problems, various combination therapy strategies, such as a combination of an anti-HER2 agent that may be used with other kinase inhibitors or PI3K-AKT signal transduction inhibitors of ErbB-family receptors, have been performed in clinical trials. CDK12 may regulate multiple tumor signaling cascades targeted by combined therapeutic strategies including current anti-HER2 therapy.

The in vitro and in vivo data according to one embodiment of the present invention show that dinaciclib, which is a potent small-molecule inhibitor of CDK12, has an effect as a new therapeutic agent for trastuzumab-sensitive and -resistant HER2+ breast cancer. In particular, it was confirmed that the treatment for HER2+ breast cancer, which includes co-amplification of HER2 and CDK12, is more remarkably effective in inhibiting CDK12 kinase activity, compared to anti-HER2 therapy.

In this regard, the subject suffering from the HER2-positive cancer may be a subject who shows the co-amplification of HER2 and CDK12.

In the present invention, the term "suppression" or "inhibition" is intended to encompass a process of allowing a certain substance to regulate transcription of a target gene to interfere with transcription, a process of hindering translation of mRNA of a gene into a protein to interfere with expression of a protein, or a process of decomposing the protein and/or mRNA itself to interfere with the role of a gene. Therefore, in the present invention, the gene suppressor or inhibitor is intended to encompass all mRNA expression inhibitors of genes, and inhibitors of expression of a protein encoded by the gene.

The inhibitor may include one or more selected from the group consisting of an antisense nucleotide, microRNA (miRNA), small interfering RNA (siRNA), short hairpin RNA (shRNA), a compound, and a protein, all of which bind complementarily to the CDK12 gene.

The protein inhibitor may include one or more selected from the group consisting of a compound, a peptide, a peptide mimetic, an aptamer, and an antibody, all of which specifically bind to the CDK12 protein.

According to one embodiment, it was particularly found that CDK12 has drug resistance to the HER2-targeted therapeutic agent when the co-amplification of HER2 and CDK12 occurs, and it was also confirmed that the drug resistance to the HER2 therapeutic agent may be suppressed or improved by suppressing CDK12 amplification or overexpression. Therefore, because the present invention newly finds that the resistance to the HER2-targeted therapeutic agent may be improved or suppressed by suppressing CDK12, and suggests a new therapeutic approach capable of co-administration with the HER2-targeted therapeutic agent, the CDK12 inhibitor or activator is not limited to specific types of agents such as compounds, antibodies, and the like, and may be widely included in the scope of the present invention.

Specifically, the CDK12 inhibitor may include one or more selected from the group consisting of dinaciclib and THZ-531, but the present invention is not limited thereto.

The composition of the present invention may be co-administered simultaneously or sequentially with the HER2-targeted therapeutic agent.

In the present invention, the term "co-administration" means that two or more drugs are administered together, and may express that two or more drugs are administered together. The co-administration may include both administering two or more drugs together and sequentially administering two or more drugs. When the pharmaceutical composition of the present invention is administered in combination with the HER2-targeted therapeutic agent, the pharmaceutical composition has advantages in that it may improve the resistance induced by the inhibitor, may suppress development of resistance by the inhibitor, and improve an effect of conventional therapeutic agents as well.

The HER2-targeted therapeutic agent may be selected from the group consisting of trastuzumab, pertuzumab, and trastuzumab emtansine (T-DM1).

Also, the present invention provides a composition for screening a drug for improving resistance to a HER2-targeted therapeutic agent or for co-administration with the HER2-targeted therapeutic agent, wherein the composition includes CDK12.

In addition, the present invention provides a method of screening a drug for improving resistance to a HER2-targeted therapeutic agent or for co-administration with the HER2-targeted therapeutic agent, wherein the method includes allowing CDK12 to come into contact with a candidate material; and selecting a candidate material which reduces a copy number of a CDK12 gene; an expression level of CDK12 mRNA; or an expression level of a CDK12 protein, or inhibits the expression of the CDK12 protein.

The method of screening a drug may further include judging the candidate material which reduces a copy number of the CDK12 gene or inhibits the expression of the CDK12 protein to be a drug for suppressing or improving resistance to the HER2-targeted therapeutic agent.

A reaction between the protein or mRNA and the candidate material may be checked using conventional methods used to check whether or not there is a protein-protein, protein-compound, DNA-DNA, DNA-RNA, DNA-protein, DNA-compound, RNA-protein, and/or RNA-compound reaction. For example, a hybridization test for checking in vitro binding between the CDK12 gene and the candidate material, a method of measuring an expression rate of the gene by means of Northern analysis, quantitative PCR, quantitative real-time PCR, and the like after reaction of a test substance with mammalian cells, a method of linking a reporter gene to the gene to introduce the reporter gene into cells, allowing the reporter gene to react with a test substance and measuring an expression rate of a reporter protein, a method of allowing a candidate material to react with a CDK12 protein and measuring the activity of the CDK12 protein, a yeast two-hybridization method, a search for phage-displayed peptide clones binding to the CDK12 protein, high-throughput screening (HTS) using natural products and chemical libraries, and the like, drug hit HTS, cell-based screening, a screening method using a DNA array, and the like may be used.

In addition to the active ingredient, the composition for screening a drug may include distilled water or a buffer solution that stably maintains a nucleic acid or protein structure. Also, the composition for screening a drug may include cells expressing CDK12, cells containing a plasmid expressing CDK12 under the control of a promoter capable of regulating a transcription rate, or the like for the purpose of in vivo experiments.

In the screening method of the present invention, the test substance may include individual nucleic acids, proteins, other extracts or natural products, compounds, and the like, which are estimated to have a potential as medicine for suppressing or improving resistance to the HER2-targeted therapeutic agent according to conventional selection modes or randomly selected.

Also, the present invention provides a treatment method for a human epidermal growth factor receptor 2 (HER2) positive cancer or a subject having a human epidermal growth factor receptor 2 (HER2)-positive cancer.

The treatment method may comprise administering a pharmaceutical composition, which includes one or more selected from the group consisting of a CDK12 gene inhibitor and a CDK12 protein activity inhibitor, to the subject having a human epidermal growth factor receptor 2 (HER2)-positive cancer, that is, a subject who has a copy number of a CDK12 gene, an mRNA expression level of the CDK12 gene, or an expression level of a CDK12 protein higher than the reference value; and/or a subject who has or is expected to have drug resistance to the HER2-targeted therapeutic agent.

The treatment method may comprise (a) providing a test sample from the subject suffering from a HER2 positive cancer; (b) determining a CDK12 level in the test sample; (c) comparing the CDK12 level in the test sample against a control sample free of HER2 positive cancer, thereby determining the presence or absence of an increase in the CDK12 level in the test sample, (d) if an increase of the CDK12 level of the test sample is present, administering a CDK12 inhibitor to the subject.

The subject suffering from the HER2 positive cancer may be being treated with a HER2 targeted therapeutic agent; be expected to have drug resistance to the HER2 targeted therapeutic agent; or have drug resistance to the HER2 targeted therapeutic agent.

The (b) determining CDK12 level comprises one or more of the following (i)-(iii):
(i) determining a copy number of CDK12 genes in the test sample (ii) determining an expression level of CDK12 proteins in the test sample; and (iii) determining an expression level of CDK12 mRNAs in the test sample.

The test sample comprises a tissue sample or blood sample.

The test sample may be a breast tissue sample or peripheral blood sample.

The (b) determining CDK12 level is conducted using a method selected from the group consisting of fluorescence in situ hybridization (FISH), a comparative genomic hybridization (CGH)-based array, a single nucleotide polymorphism array (a SNP array), sequence assembly comparison, paired-end sequencing, a multiplex ligation dependent probe amplification (MLPA) method, a multiplex amplifiable probe hybridization (MAPH) method, quantitative multiplex PCR of short fluorescent fragments (QMPSF), a microsatellite genotyping method, Southern blotting, immunohistochemistry (IHC), a polymerase chain reaction (PCR), a quantitative polymerase chain reaction (qPCR), a quantitative real-time polymerase chain reaction (qRT-PCR), a real-time polymerase chain reaction (real-time PCR), microarray-based comparative genomic hybridization, and a ligase chain reaction (LCR).

The CDK12 inhibitor of step (d) comprises one or more selected from the group consisting of an antisense nucleotide, small interfering RNA (siRNA), short hairpin RNA (shRNA), a peptide, a peptide mimetic, an aptamer, and an antibody, which complementarily or specifically bind to CDK12, or comprises one or more selected from the group consisting of dinaciclib and THZ-531.

The HER2 targeted therapeutic agent is selected from the group consisting of trastuzumab, pertuzumab, and trastuzumab emtansine (T-DM1).

The determining CDK12 level in the sample is performed with a sense primer, an antisense primer, an antibody, an aptamer, or a probe which is complementary or specifically binds CDK12.

The (i) determining a copy number of CDK12 genes in the tissue sample is performed by fluorescent in situ hybridization (FISH). The FISH is performed with a nucleic acid probe that is fluorescently labeled.

The CDK12 gene may have the sequence of SEQ ID NO: 3.

All the contents described above in the present invention are applicable mutatis mutandis to the therapeutic method of the present invention.

The method of the present invention may further include co-administering the HER2-targeted therapeutic agent to the subject to which the pharmaceutical composition has been administered.

The method of the present invention may further include measuring a copy number of a CDK12 gene, an mRNA expression level of the CDK12 gene, or an expression level of a CDK12 protein from the sample obtained from the subject having a human epidermal growth factor receptor 2 (HER2)-positive cancer before the administration of the pharmaceutical composition. This step includes measuring a level of CDK12 as a companion diagnostic marker for the HER2-targeted therapeutic agent to predict an effect or outcome of the HER2-targeted therapeutic agent, that is, performing companion diagnostics.

The administration may include all methods for oral administration or parenteral administration. In this case, the composition may be administered using methods commonly used in the technical field of the present invention. In the case of co-administration, two drugs may also be administered via different routes of administration, that is, a first drug may be administered by parenteral administration, and a second drug may be administered by oral administration.

In the present invention, it was confirmed from specific Examples that, when the CDK12 inhibitor is administered with trastuzumab to the subject who suffers from HER2-positive breast cancer and has resistance to the HER2-targeted therapeutic agent, the resistance to the trastuzumab is improved, and a therapeutic effect of trastuzumab is further improved.

In addition, the present invention provides a use of the agent for measuring a copy number or an expression level of CDK12 in the sample, which is obtained from the subject suffering from a human epidermal growth factor receptor 2 (HER2)-positive cancer, for companion diagnostics of the HER2-targeted therapeutic agent.

Further, the present invention provides a use (i.e., an application) of an agent for measuring a CDK12 level in the sample, which is obtained from the subject suffering from a human epidermal growth factor receptor 2 (HER2)-positive cancer, or a use (i.e., an application) of a kit including the agent, for preparing a companion diagnostic kit for the HER2-targeted therapeutic agents.

Furthermore, the present invention provides an application of the CDK12 inhibitor for preparing a drug for treating a subject having a human epidermal growth factor receptor 2 (HER2)-positive cancer, that is, a subject who has a copy number or an expression level of CDK12 higher than the reference value; a subject who has drug resistance to the HER2-targeted therapeutic agent; or a subject who is expected to have drug resistance to the HER2-targeted therapeutic agent.

All the contents described above in the present invention are applicable mutatis mutandis to the use of the present invention.

Hereinafter, the present invention will be described in detail with reference to embodiments thereof.

However, it should be understood that the following examples are given for the purpose of illustration of the present invention only, and are not intended to limit the scope of the present invention.

EXAMPLES

[Experimental Preparation and Method]

1. Cell Culture and Reagent

HER2+ human breast cancer cell lines including BT474, ZR-75-30, HCC-1419, HCC-1954, and SKBR3 were obtained from the American Type Culture Collection (ATCC; Manassas, VA, USA), and cultured in RPMI-1640 media containing 10% fetal bovine serum (FBS, Welgene, Korea). All the cells were cultured at 37° C. in a humidified 5% $CO_2$ incubator. Trastuzumab and dinaciclib were purchased from Roche (Roche, Basel, Switzerland) and Selleckchem (SCH727965, Selleckchem, Houston, TX, USA), respectively.

2. Lentiviral Infection and Stable Cell Production

Human CDK12 cDNA (SEQ ID NO: 3) was cloned into a lentiviral pLVX-puro vector (Clontech, Mountain View, CA, USA), and each of shRNAs for CDK12 (Cat #: RHS4531-EG51755; CloneID: V3LHS_349483 (SEQ ID NO: 7) and V3LHS_645396 (SEQ ID NO: 8)) was inserted into a pGIPZ vector (GE Dharmacon, Lafayette, CO, USA). A lentivirus encoding CDK12 cDNA or shRNA was prepared in the same manner as described above[43]. To establish each of stable CDK12-overexpressing and -knockdown cell lines, each of the cell lines was infected with the lentivirus containing the CDK12 cDNA or shRNA together with 6 μg/mL of polybrene (Sigma-Aldrich, St. Louis, MO, USA). The infected cells were selected with 2 μg/mL puromycin (Sigma-Aldrich).

3. Immunoblotting and Immunoprecipitation

The cells were lysed in a radioimmunoprecipitation buffer solution containing a protease-inhibitor cocktail or a phosphatase-inhibitor cocktail, Immunoblotting was performed as previously known in the art[44]. For immunoprecipitation, a cell lysate was incubated with a proper antibody overnight at 4° C., and precipitated with protein A- or G-agarose beads at 4° C. for 2 hours. An immune complex including the agarose beads was washed with chilled phosphate-buffered saline (PBS) three times, and heated at 95° C. for 5 minutes in a 3× sample-loading buffer solution containing β-mercaptoethanol. The sample was subjected to sodium dodecyl sulfate polyacrylamide gel electrophoresis, and immunoblotting was performed as previously known.

The following antibodies were used for immunoblot and co-immunoprecipitation analyses: CDK12 (ab57311) was obtained from Abcam (Cambridge, MA, USA); phosphorylated (p)-EGFR (2236S), p-HER3 (4791S), p-IRS1 (3203S), IRS1 (3407S), p-CTD (13499S), CTD (2629S), p-AKT (4060S), AKT (9272S), p-ERK (9101S), ERK (9102), p-GSK-3 (9336), and GSK-3 (9315S) were obtained from Cell Signaling Technology (Beverly, MA, USA); p-HER2 (06-229), β-actin (MAB1501R), p 85 (06-195), and histone H3 acetylation (06-599) were obtained from Santa Cruz Biotechnology (Dallas, TX, USA); HER3 was obtained from Invitrogen (Carlsbad, CA, USA); and β-catenin was obtained from BD Biosciences (Franklin Lakes, NJ, USA).

4. qRT-PCR

Total RNA extraction and RT-PCR were performed according to previously known methods[45]. A 7300 real-time PCR system and a SYBR Green master mix (Applied Biosystems, Foster City, CA, USA) were used to quantify a level of target-gene mRNA, which was then normalized using a glyceraldehyde 3-phosphate dehydrogenase (GAPDH) mRNA level.

The following specific primers were used for qRT-PCR analysis:

CDK12:
5'-CCTGGAGATGATGACATGGATAG-3'; (SEQ ID NO: 9)

WNT1:
5'-CCGATGGTGGGGTATTGTGA-3' (SEQ ID NO: 10)
and
5'-CCCGGATTTTGGCGTATCAG-3'; (SEQ ID NO: 11)

WNT3:
5'-CGTGTTAGTGTCCAGGGAGT-3' (SEQ ID NO: 12)
and
5'-GCATTTGAGGTGCATGTGGT-3'; (SEQ ID NO: 13)

IRS1:
5'-GGTGGATGACTCTGTGGTGG-3' (SEQ ID NO: 14)
and
5'-GGACGCTGATGGGGTTAGAG-3'; (SEQ ID NO: 15)

AQP3:
5'-TGCTACCTACCCCTCTGGAC-3' (SEQ ID NO: 16)
and
5'-GTCAACAATGGCCAGCACAC-3'; (SEQ ID NO: 17)

CD74:
5'-ACGGCAACTATCTGCCACTC-3' (SEQ ID NO: 18)
and
5'-CTCTCACATGGGGACTGGGC-3'; (SEQ ID NO: 19)

TSPAN8:
5'-CCCAGGAGCTATGACAAGCA-3' (SEQ ID NO: 20)
and
5'-GCACTCACACCTGCCATTTC-3'; (SEQ ID NO: 21)

FGF8:
5'-GGGTGTCTCCCAACAGGTAAC-3' (SEQ ID NO: 22)
and
5'-TCTGCTTCCAAAGGTGTCCG-3'; (SEQ ID NO: 23)

FGF19:
5'-GCTTTCGAGGAGGAGATCCG-3' (SEQ ID NO: 24)
and
5'-GGGGCGAAGAGAACATGTCA-3'; (SEQ ID NO: 25)

WNT5B:
5'-CAGGAGCACATGGCCTACAT-3' (SEQ ID NO: 26)
and
5'-GGCTGCCTATCTGCATGACT-3'; (SEQ ID NO: 27)

TCF7:
5'-ACATGCAGCTATACCCAGGC-3' (SEQ ID NO: 28)
and
5'-ACTGTCATCGGAAGGAACGG-3'; (SEQ ID NO: 29)

DKK1:
5'-GTGCAAATCTGTCTCGCCTG-3' (SEQ ID NO: 30)
and
5'-GCACAACACAATCCTGAGGC-3'; (SEQ ID NO: 31)

TLE1:
5'-CCGCTGTGACTACTCTGGAC-3' (SEQ ID NO: 32)
and
5'-AGGGACGACATCCACGAGAT-3'; (SEQ ID NO: 33)

MMP9:
5'-CAGTCCACCCTTGTGCTCTT-3' (SEQ ID NO: 34)
and
5'-CGACTCTCCACGCATCTCTG-3'; (SEQ ID NO: 35)

MYCBP:
5'-AGAGCTGCTTCGCCTAGAAC-3' (SEQ ID NO: 36)
and
5'-TTCTCCTCCTGAGGTGGTTCA-3'; (SEQ ID NO: 37)

TWIST:
5'-CGGACAAGCTGAGCAAGATT-3' (SEQ ID NO: 38)
and
5'-CCTTCTCTGGAAACAATGAC-3'; (SEQ ID NO: 39)

SNAI1:
5'-AGCCTGGGTGCCCTCAAGATG-3' (SEQ ID NO: 40)
and
5'-CTTGGTGCTTGTGGAGCAGGGAC-3'; (SEQ ID NO: 41)
and

GAPDH:

5'-GAAGGTGAAGGTCGGAGTC-3' (SEQ ID NO: 42)
and

5'-GAAGATGGTGATGGGATTTC-3'. (SEQ ID NO: 43)

5. Flow Cytometry

To analyze a breast CSC-like cell population, the cells were stained with allophycocyanin-conjugated CD44, phycoerythrin-conjugated CD24 (BD Biosciences), and fluorescein isothiocyanate-conjugated ESA (Dako, Carpinteria, CA, USA), as previously described. The ratio of breast CSCs was measured based on the expression of a surface marker (CD44+/CD24−/ESA+) using a FACSCanto II flow cytometer (BD Biosciences).

6. Tumorsphere Analysis

Formation of tumorspheres in CDK12-overexpressing or -knockdown HER2+ breast cancer was analyzed according to methods disclosed in the related art[44]. In summary, BT-474 ($5 \times 10^3$ cells/well), ZR-75-30 ($5 \times 10^3$ cells/well), HCC-1419 ($5 \times 10^3$ cells/well), and HCC-1954 ($5 \times 10^3$ cells/well) were cultured in a DMEM-GlutaMAX medium (Invitrogen), which contained 2% B27 (Invitrogen), 20 ng/mL of a basic fibroblast growth factor (Peprotech, Rocky Hill, NJ, USA), 20 ng/mL of an epidermal growth factor (Sigma-Aldrich), and 4 ng/mL of heparin (Sigma-Aldrich), in a 6-well ultra-low adhesion surface plate (Corning, Corning, NY, USA). After 3 days, 5 days, and 7 days, tumorsphere formation was analyzed, and quantified using an inverted microscope. For a secondary tumorsphere-formation assay, primary tumorspheres (diameter: >100 μm) were harvested after 7 days, and suspended in 0.05% trypsin EDTA to separate single cells. Thereafter, the single cells were cultured as described above.

7. In Vivo Tumor Xenografting

All mouse experiments were approved by the Institutional Animal Care and Use Committee of HanYang University (Seoul, Korea). Five-week-old female NOD/SCID mice were purchased from KoATECH (Pyeongtaek, Korea). For an in vivo limiting-dilution assay, serially diluted CDK12-overexpressing ZR-75-30 cells and CDK12-knockdown BT474 cells were orthotopically injected into mice (see Tables 1 and 2). Here, an E2 pellet (0.72 mg/pellet; 60 day release; Innovative Research of America, Sarasota, FL, U.S.A.) was transplanted into the mice 2 days before the cell injection. Tumor formation frequency was analyzed as previously described[44]. To evaluate an in vivo effect of trastuzumab, BT474 and HCC-1954 cells ($2 \times 10^6$ and $1 \times 10^6$ cells, respectively) mixed with PBS and Matrigel (BD Biosciences) were orthotopically injected into the mice. When the tumor size reached approximately 100 mm$^3$, trastuzumab (20 mg/kg) and/or dinaciclib (20 mg/kg) was intraperitoneally injected into the mice. The size of a tumor was measured twice a week for 5 to 6 weeks, and calculated according to the following Equation 1:

$$\text{Volume(mm}^3\text{)} = (a \times b^2)/2 \quad \text{[Equation 1]}$$

(wherein a represents the largest diameter, and b represent a vertical diameter.)

8. Sulforhodamine B (SRB) Colorimetric Analysis

An in vitro toxicity testing kit (SRB-based TOX6) was purchased from Sigma-Aldrich. To analyze cell growth, ZR-75-30 ($1 \times 10^3$ cells/well), HCC-1419 ($3 \times 10^3$ cells/well), BT474 ($2 \times 10^3$ cells/well), and HCC-1954 ($1 \times 10^3$ cells/well) were seeded in a 96-well plate, and cell proliferation activity was analyzed for 7 days according to the manufacturer's instructions using an SRB analysis kit. To analyze a drug response, the cells ($5 \times 10^3$ cells/well) were cultured in RPMI-1640 supplemented with 10% FBS in a 96 well-plate. Here, 0.1 μg/mL to 10 μg/mL of trastuzumab and/or 5 nM to 10 nM dinaciclib was added or not added to the medium. The medium was replaced with a fresh medium containing the drug every three days. After the treatment with the drug, cell viability was determined using an SRB analysis kit.

9. RNA-Seq Analysis

Total RNA was extracted from the control or CDK12-overexpressing ZR-75-30 cells using a TRIzol RNA isolation reagent (Life Technologies, Carlsbad, CA, USA). RNA integrity was analyzed in a bioanalyzer using an Agilent RNA 6000 Pico kit (Agilent Technologies, Santa Clara, CA, USA). The extracted total RNA was processed into a prepared mRNA-sequencing library according to the manufacturer's instructions using a TruSeq-stranded mRNA LT sample preparation kit (Illumina, San Diego, CA, USA). All the samples were sequenced with an Illumina HiSeq2500 sequencer (Illumina) using paired-end 100-bp reads. The raw image data was converted into sequence data by means of base-calling, and stored in a FASTQ format. The paired-end reads of six separate samples were adjusted for both PCR and a sequencing adaptor using Cutadapt (cutadapt.readthedocs.io/en/stable/, Ver. 1.16).

The adjusted reads were aligned to the hg19 human reference genome using STAR (Ver. 2.6.0c)[46], and the gene-level read counts were prepared using a featureCounts function of a Subread package (Ver. 1.6.2)[47]. The presence of significant difference in expression was determined at the gene level using edgeR (Ver. 3.22.3)[48]. All the genes exhibited at least a 1.5-fold change between the CDK12-overexpressing group and the control. This data was deposited in the Gene Expression Omnibus (GEO) under accession number GSE117523. To functionally classify genes differentially expressed between the control and the CDK12-overexpressing group, all gene sets in the Molecular Signatures Database (software.broadinstitute.org/gsea/msigdb/index.jsp) Ver. 6.2 were analyzed using GSEA (Ver. 3.0), and modified for various hypothesis tests. The false-discovery rate (FDR) threshold value was set to 0.25[49]. A heat map of the difference in gene expression was constructed using the R language (www.r-project.org/; Ver. 3.5.1).

10. Public Data

The data sets of publicly available human breast cancer patients from METABRIC and the Cancer Genome Atlas (TCGA) were downloaded from cBioportal (www.cbioportal.org/) and analyzed again. The breast cancer cohorts (METABRIC and TCGA), and OncoPrint of the Cancer Cell Line Encyclopedia data sets for genetic modification of CDK12 were prepared using cBioportal. In the breast cancer patients from METABRIC, the co-amplification frequency with HER2 and the prognostic impact of a 17q12-amplicon gene were analyzed using an R programming package. In the METABRIC and GEO data sets, disease-free survival (DFS) and overall survival (OS) of the breast cancer patients were analyzed using recently developed web applications CTGS (Cancer Target Gene Screening; ctgs.biohackers.net) and a KM plotter (www.kmplot.com), respectively. To stratify patient groups according to the gene expression level from METABRIC, the most effective cut-off points of the respective genes were calculated based on the highest P-value using CTGS. In the KM plotter, the automatic selective optimum cut-off value of CDK12 (225697 s at) was used. Relative to the NPI and AOL, the independent prognostic impact of CDK12 was expressed by a modified Cox proportional hazard model using Breast Cancer Gene-Expression Miner Ver. 4.1 (bc-GeneExMiner 4.1, bcgenex.centregauducheau.fr). Public data sets, an expression-profiling array of dinaciclib-treated MDA-MB-231 cells (GSE88822[24]), and PolII ChIP-seq (GSE72023[30]) of Jurkat cells were obtained from GEO, and analyzed again.

11. ChIP Assay

A ChIP assay was performed according to the manufacturer's instructions using a ChIP assay kit (Upstate Biotechnology, Lake Placid, NY, USA). Fold enrichment of ChIP signals (signals relative to the background signals) was determined using real-time qPCR. The following primers were used for ChIP-qPCR:

```
IRS1 TSS:
                                        (SEQ ID NO: 44)
5'-CGTGGATTTCAGAGTCGGGG-3'
and (SEQ ID NO: 45)
5'-GAGGCTCCGAAAAACAACCG-3';
WNT1 TSS:
                                        (SEQ ID NO: 46)
5'-CCATTGTCTGCGCCCCTAA-3'
and (SEQ ID NO: 47)
5'-CGGCACCGCCTCTTATAGT-3';
and WNT3 TSS:
                                        (SEQ ID NO: 48)
5'-TCGCTGACATCCTCAAACCC-3'
and (SEQ ID NO: 49)
5'-GACGCCCCAATAGTTGGAA-3'.
```

12. Nuclear and Cytoplasmic Cell Fractions

To analyze an intracellular position of β-catenin, nuclear and cytoplasmic fractions were obtained from cells according to the manufacturer's instructions using an NE-PER nuclear and cytoplasmic extraction reagent (Pierce, Rockford, IL, USA). The fractionated extracts were subjected to immunoblotting, as previously described.

13. Immunofluorescence Staining

The cells ($8 \times 10^4$ cells/well) were seeded on a 4-chamber glass slide, kept overnight, washed, and fixed with cold methanol for 5 minutes. After the cells were blocked with 3% bovine serum albumin for an hour, the cells were stained with anti-3-catenin (1:200), incubated overnight at 4° C., and then treated with anti-rabbit immunoglobulin/R-PE (1:400; P9795; Sigma-Aldrich) for an hour. The stained cells were further stained with 4',6-diamidino-2-phenylindole for 10 minutes to visualize the nuclei. Fluorescence was detected using a fluorescence microscope (Nikon, Tokyo, Japan).

14. Luciferase-Reporter Assay

To analyze β-catenin/TCF-promoter activity, cells were co-transfected with a pTOP-FLASH or pFOP-FLASH luciferase-reporter construct containing either a wild-type or mutant TCF-binding site; and a β-galactosidase expression vector. Luciferase activity was analyzed according to the manufacturer's instructions using a luciferase analysis kit (Promega, Madison, MI, USA). Luciferase activity is expressed in relative light units (RLU), and standardized according to β-galactosidase activity.

15. Human RTK Assay

A phosphorylation level of multiple RTKs in CDK12-knockdown BT474 cells was analyzed according to the manufacturer's instructions using a human phospho-RTK array kit (R&D Systems, Minneapolis, MN, USA). A cell lysate was diluted, and incubated with a human phosphokinase membrane. In this case, a membrane spotted twice with an antibody against a phosphorylated RTK overnight at 4° C. was used. The membrane was reacted with a secondary antibody, and exposed onto an X-ray film. The given relative spot intensity was measured using AlphaEaseFC software (AlphaInnotech, Inc., San Leandro, CA, USA).

16. Statistic Analysis

Statistical significance of a difference between two groups was analyzed using an unpaired Student's t test. Multiple group comparison and repeated measurements were performed using analysis of variance (ANOVA) and repeated measures ANOVA (RM ANOVA), and the results were then subjected to post hoc least-significant difference (LSD) analysis. A Kaplan-Meier plot for survival analysis was evaluated using log-rank analysis. To evaluate the frequency of tumorigenicity, the limiting-dilution assay results were calculated using L-Calc software (Stemcell Technologies, Vancouver, Canada). All the P-values were obtained by a two-sided test, and $P<0.05$ was considered to be statistically significant.

[Experimental Example 1] Confirmation of Genes Having Clinical Implications in Chr17q12

Figure 1:
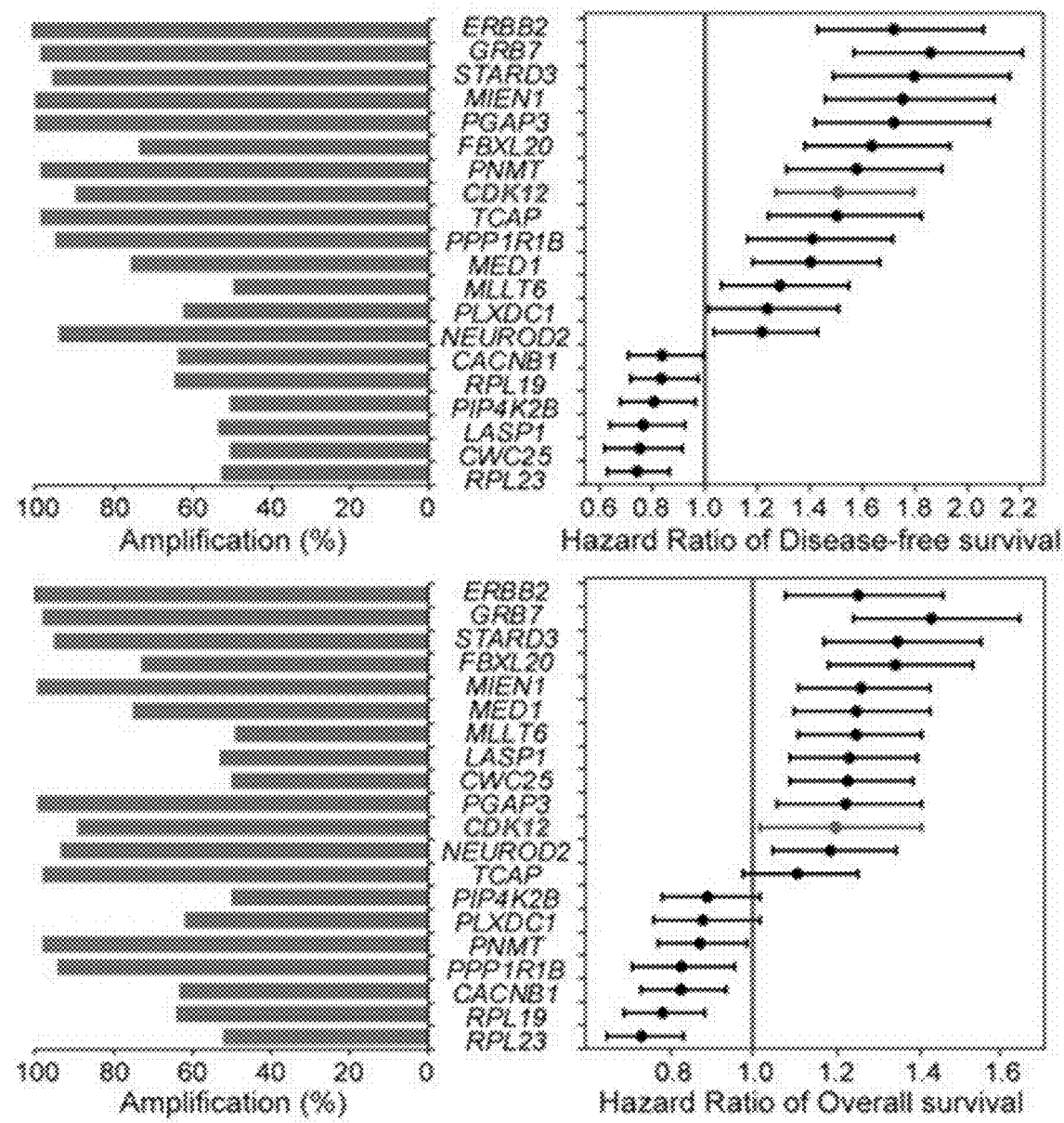
FIGS. 1, 2, 3A, 3B, 4A, 4B, 5A and 5B show the results of confirming whether or not HER2 and genes are amplified in 17q12, the relationship with CDK12, and the relationship between amplification and treatment outcome. Co-amplification of HER2 and CDK2 in 17q12 may be associated with a poor breast cancer prognosis.

In the prior art, the potential importance of a 17q12-amplicon gene in breast cancers has been suggested[11,25], but the clinical relevance of these genes remains unclear. To identify the clinical implications of a HER2 amplicon, an effect of an expression level of each of the genes located at chr17q12 on the survival of breast cancer patients was examined using Molecular Taxonomy of Breast Cancer International Consortium (METABRIC) data sets (n=1980). Many genes in the 17q12 amplicon (including MIEN1, PGAP3, TCAP, GRB7, STARD3, and CDK12 as well as HER2) were associated with the high risk of recurrence or death in the breast cancer patients (FIG. 1). Also, various genes including RPL19, PIP4K2B, and CACNB1 were associated with favorable survival outcomes in the cohort. This indicates that the chr17q12 includes both cancer genes and tumor suppressor genes.

Figure 2:
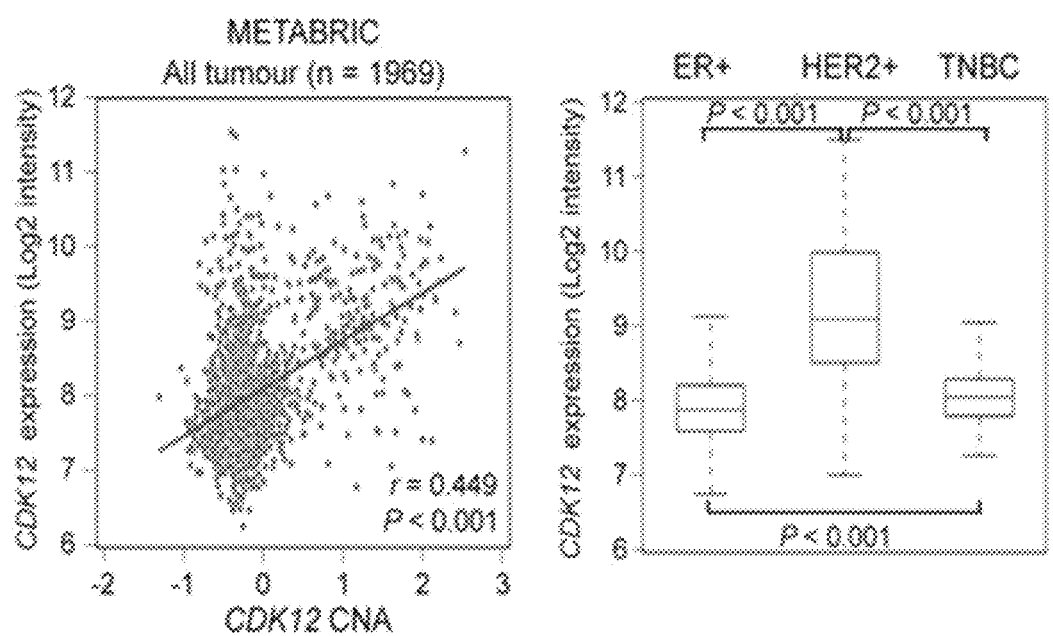
Figure 3A:
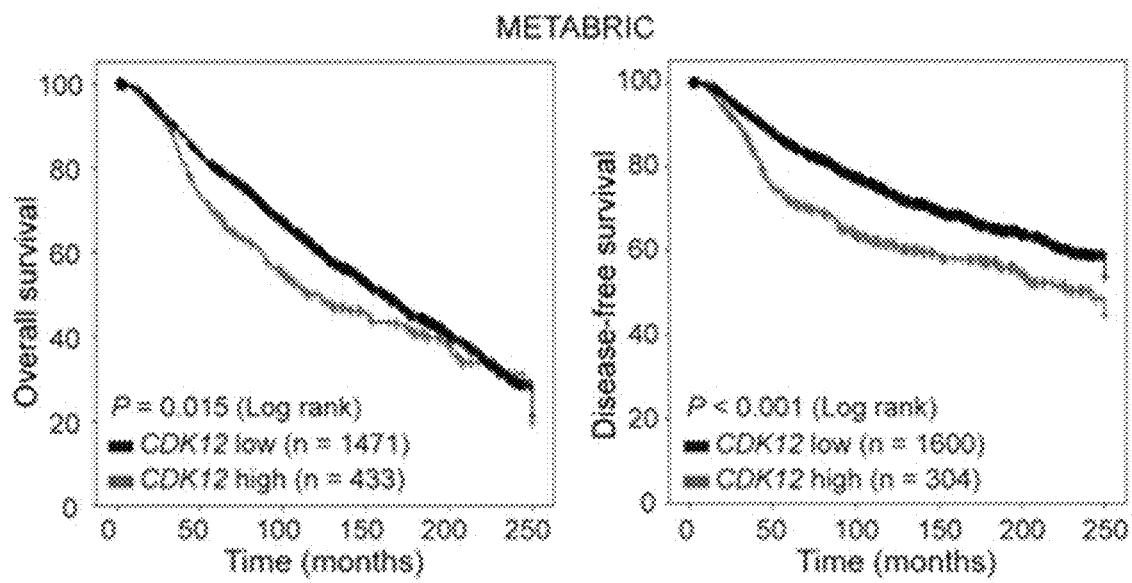
Figure 3B:
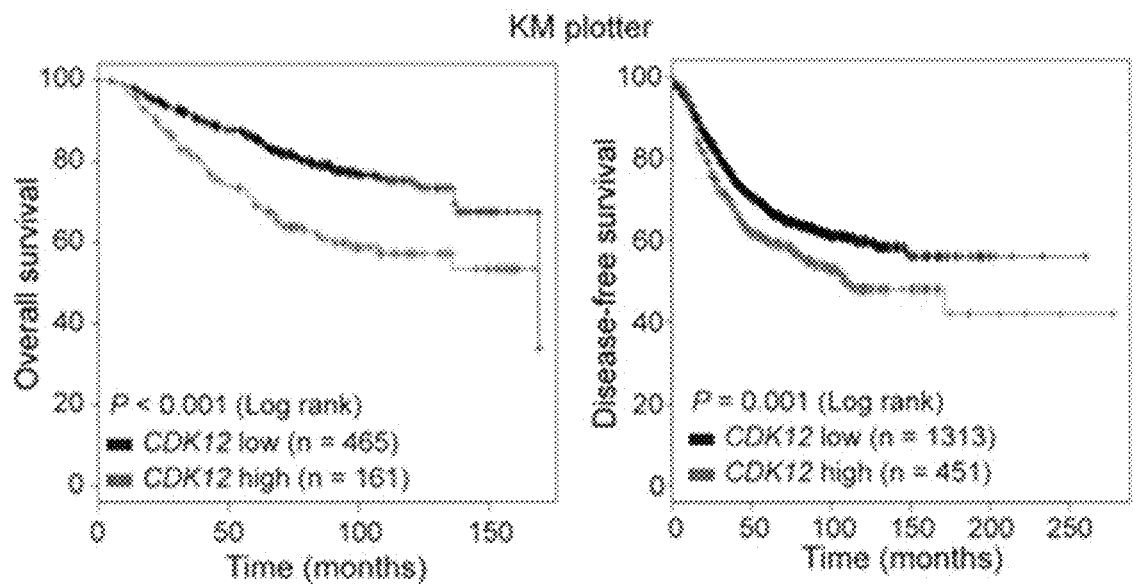
Figure 4A:
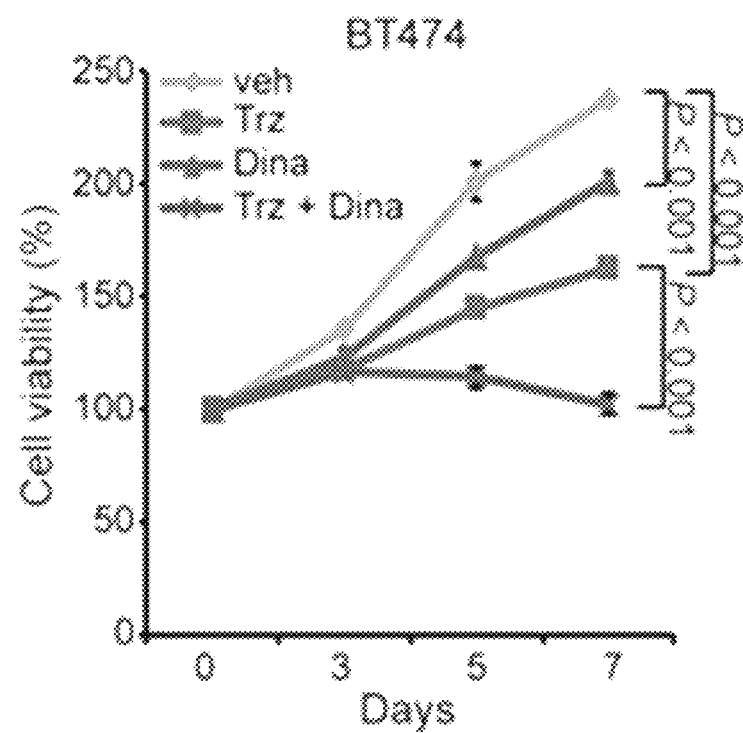
Figure 4B:
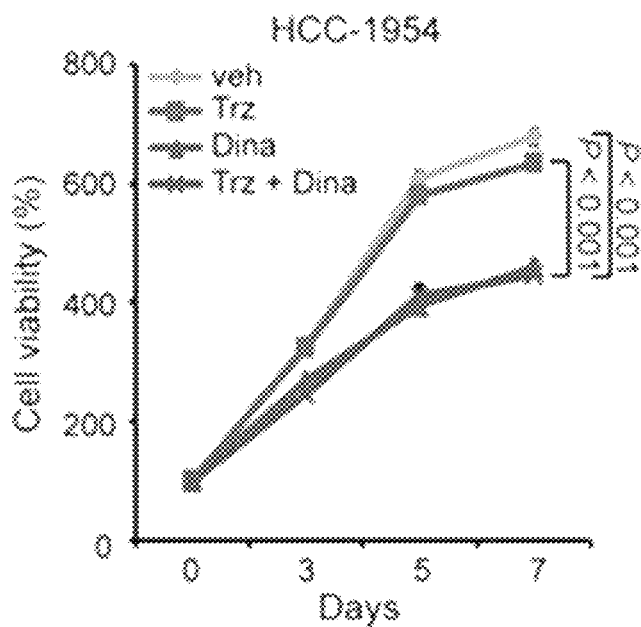
Figure 5A:
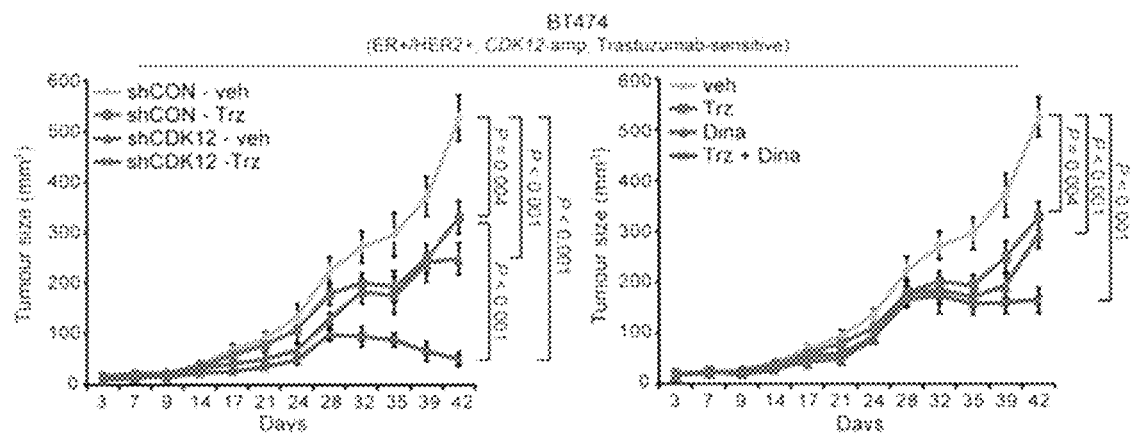
Figure 5A:
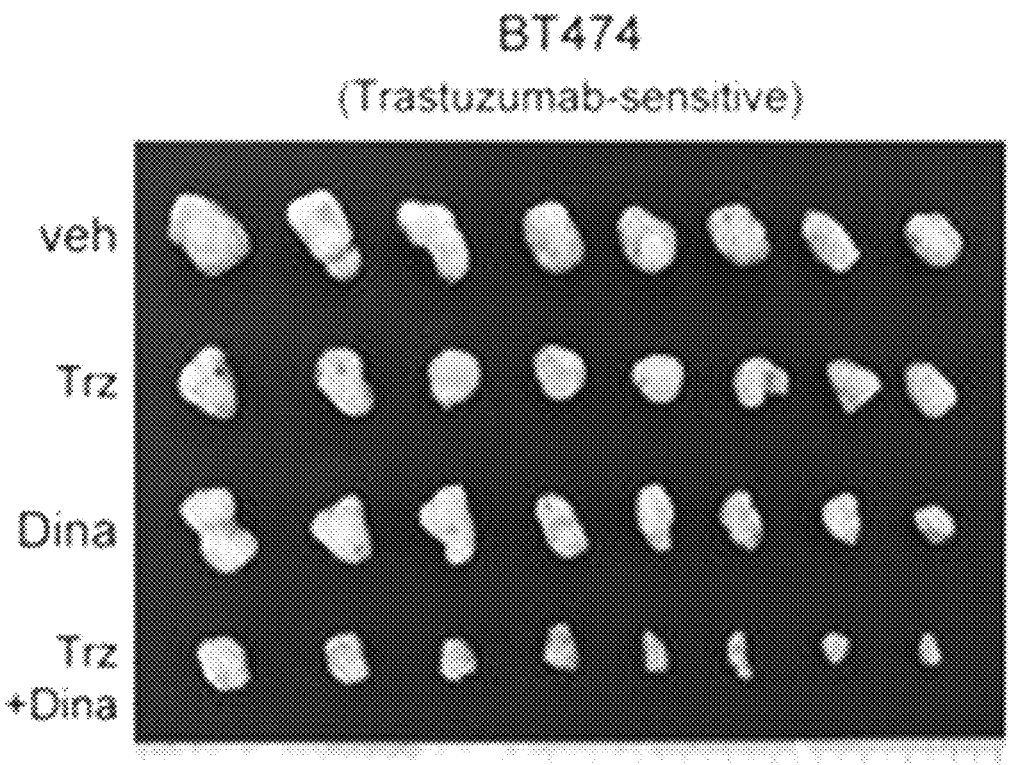
Figure 5B:
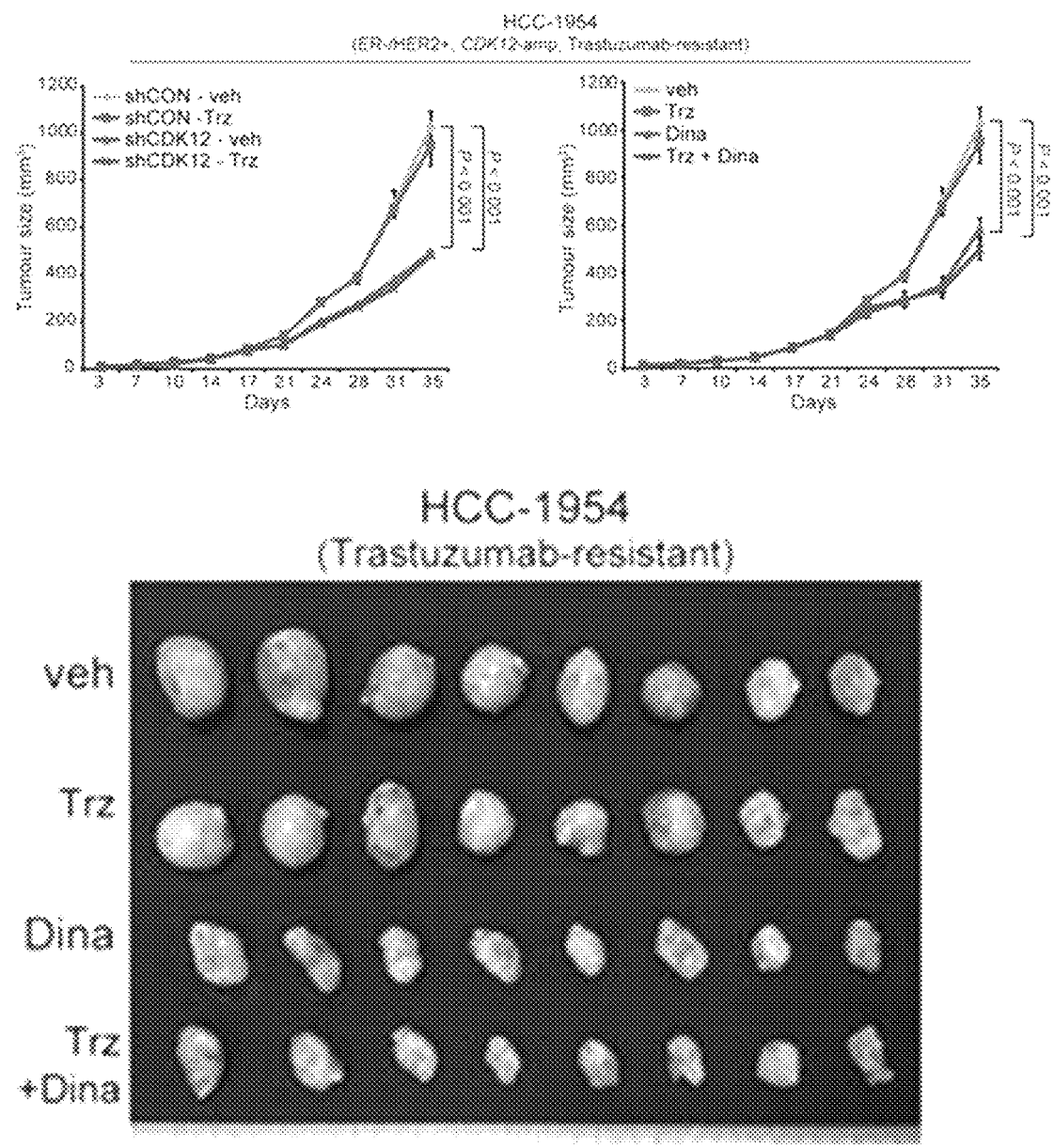
Figure 6:
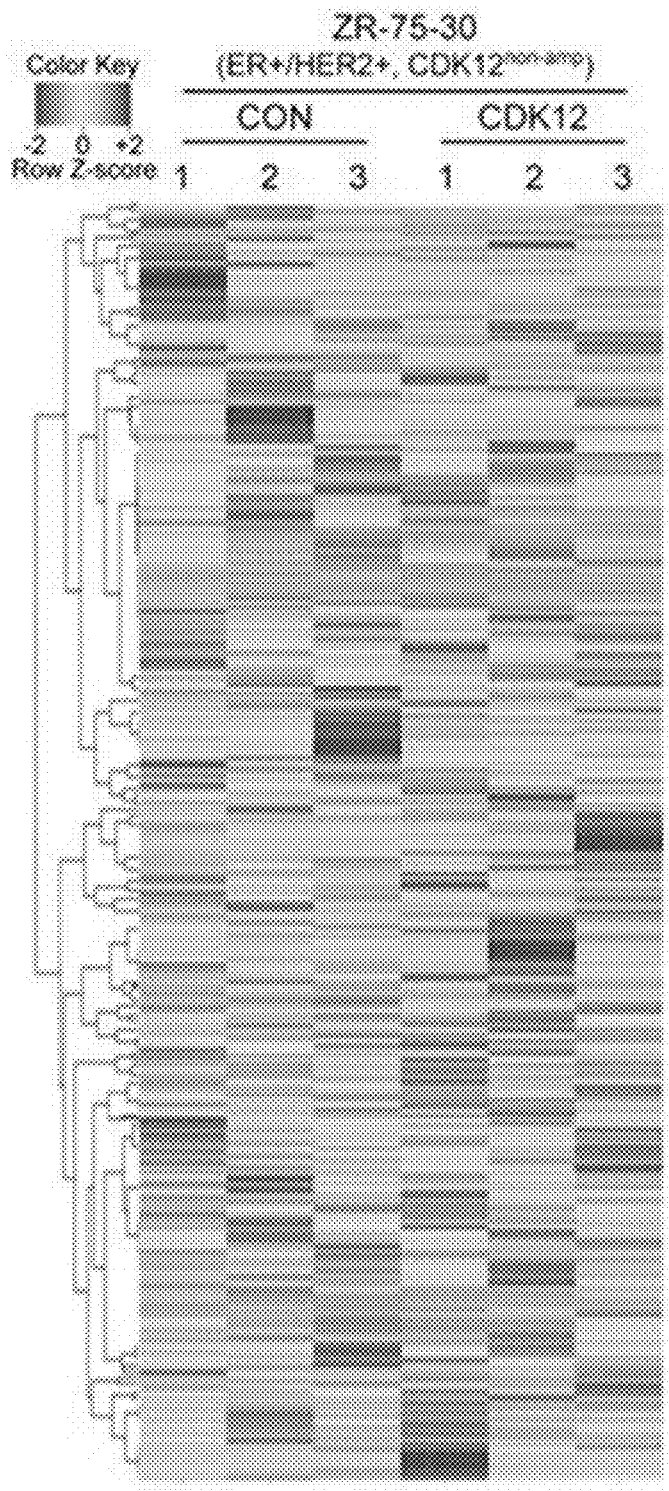
FIGS. 6, 7, 8, 9, 10A, 10B, 11A and 11B show the results of determining roles of CDK12 that transcriptionally upregulates activation factors in various tumor signaling cascades.
Figure 7:
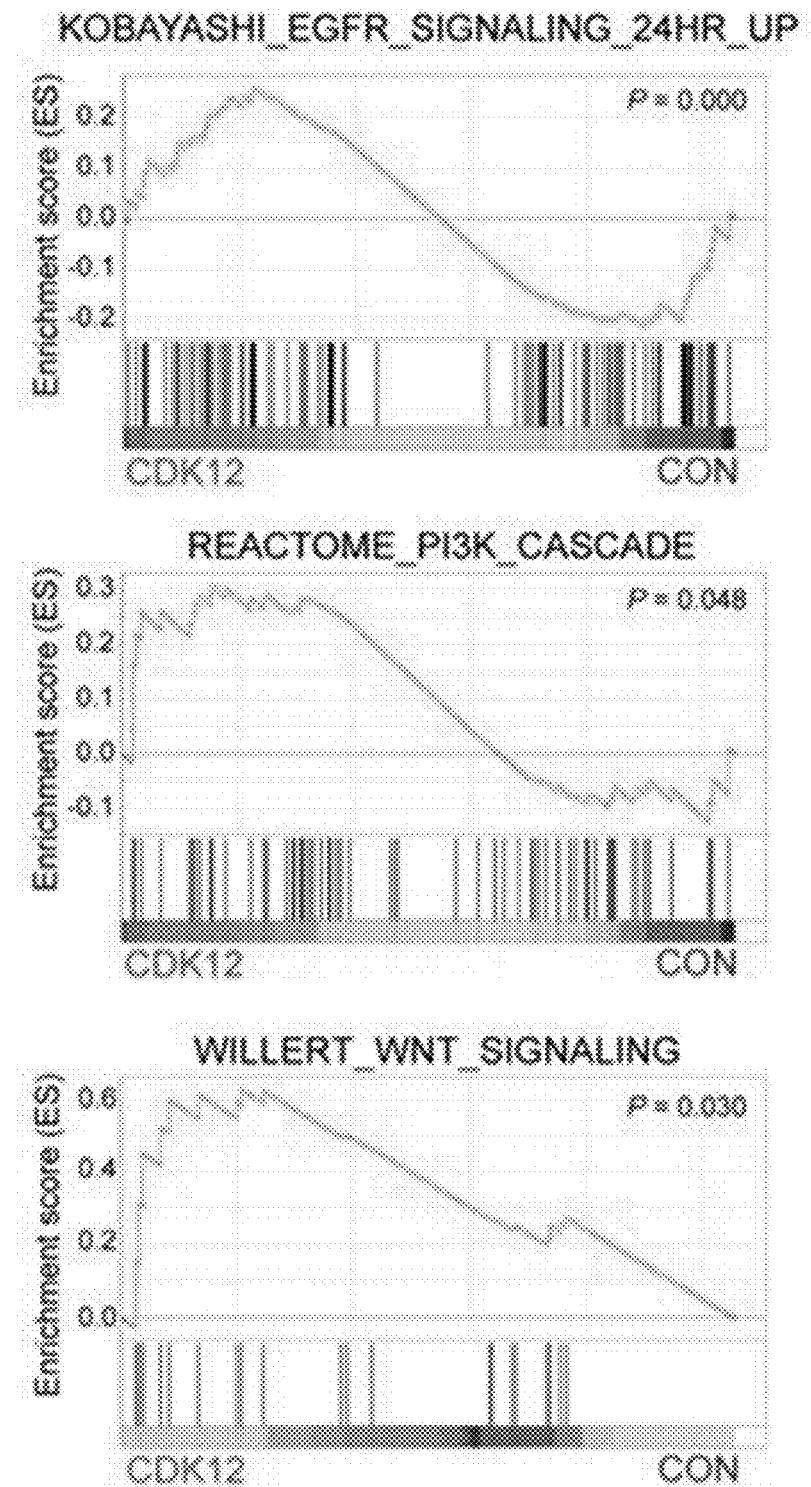
Figure 25:
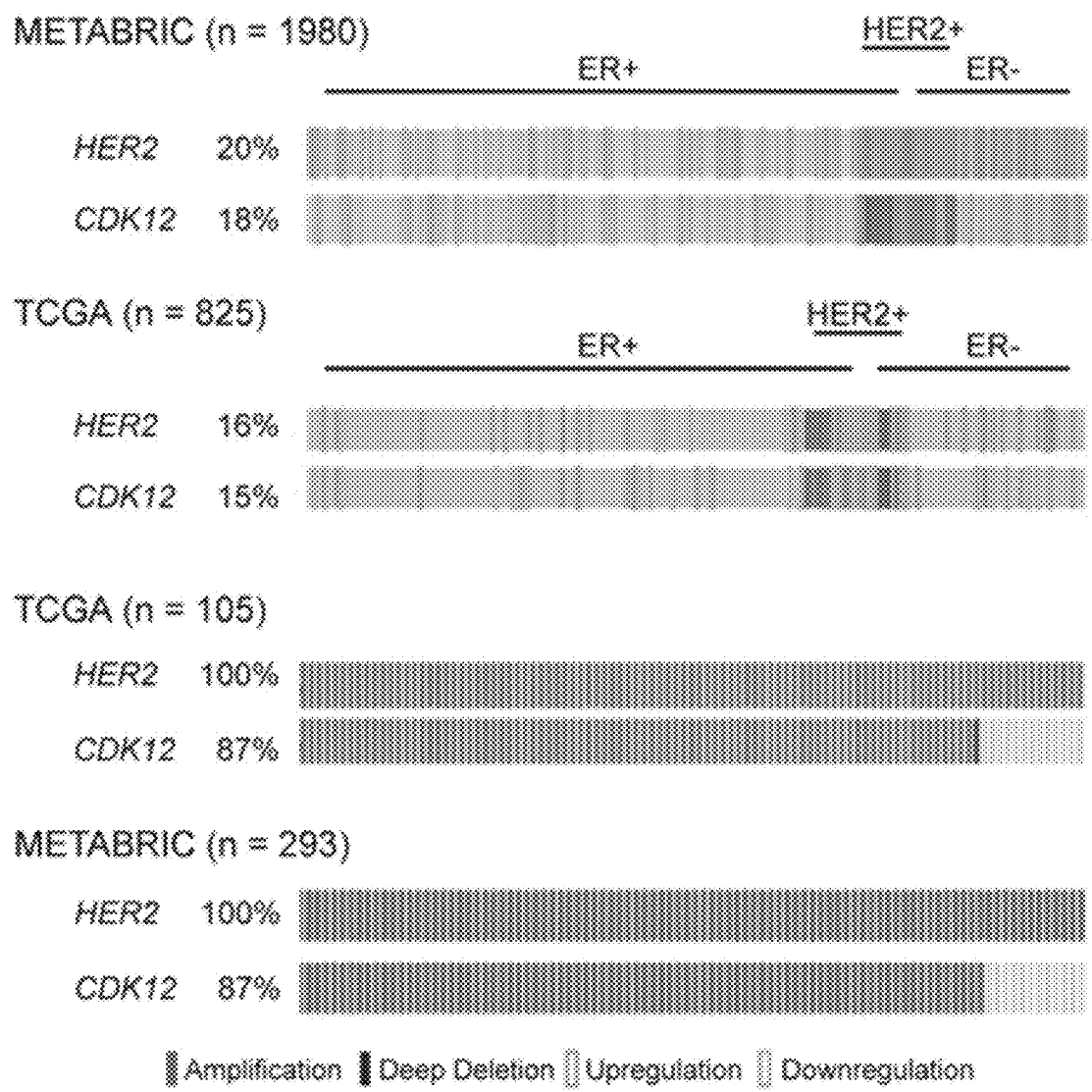
FIGS. 25, 26, 27, 28 and 29 show the relationship between CDK12 amplification and poor prognosis in HER2+ breast cancer.
Figure 26:
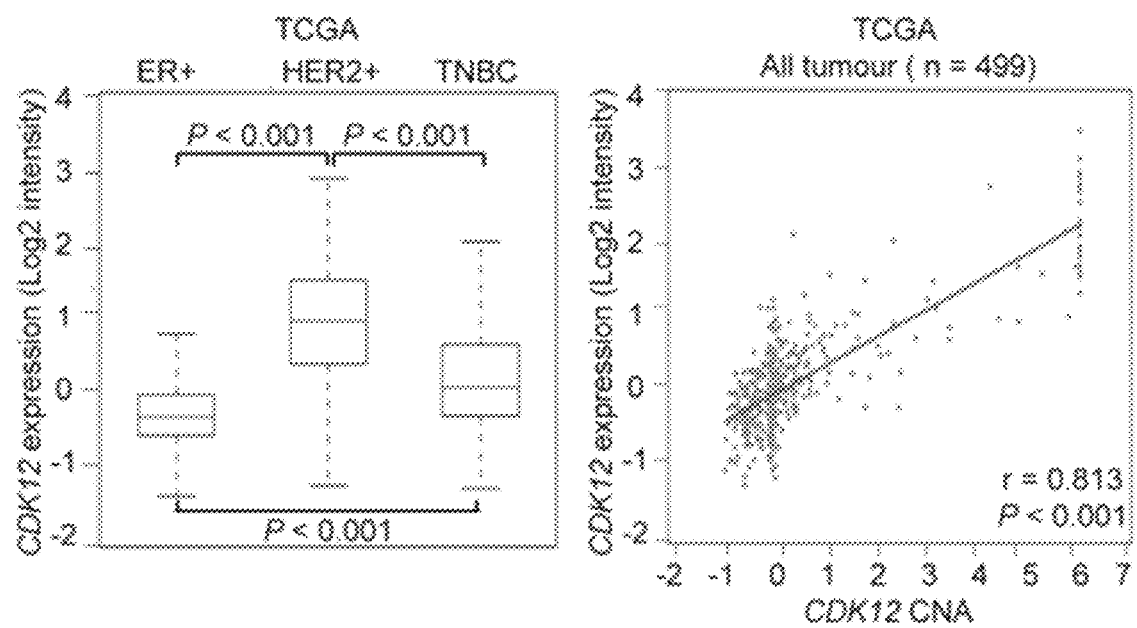
Figure 27:
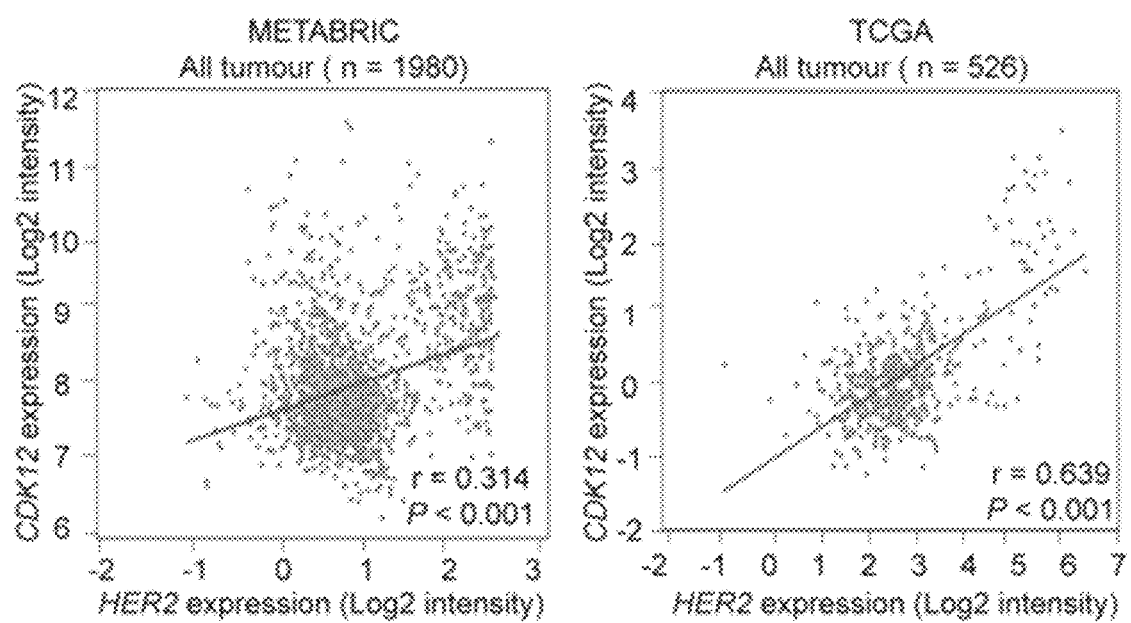
Figure 28:
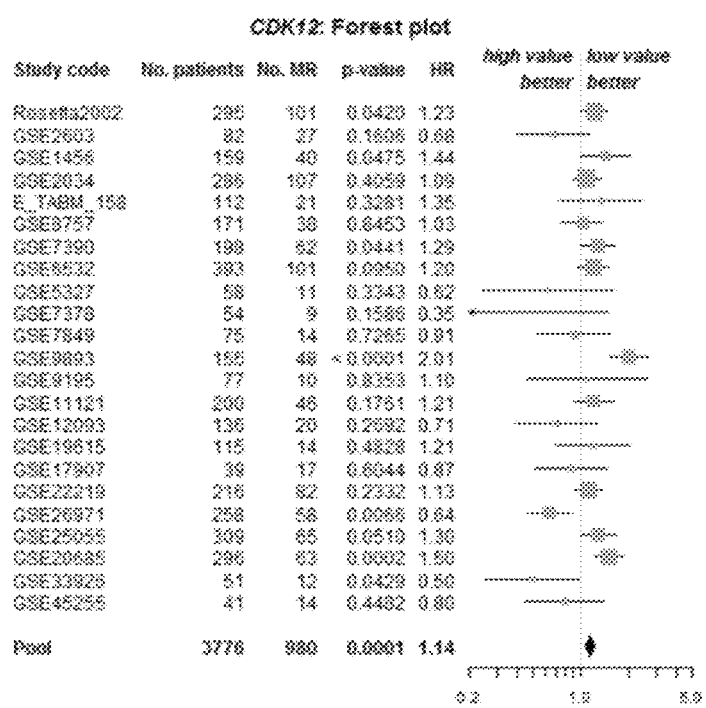
Figure 29:
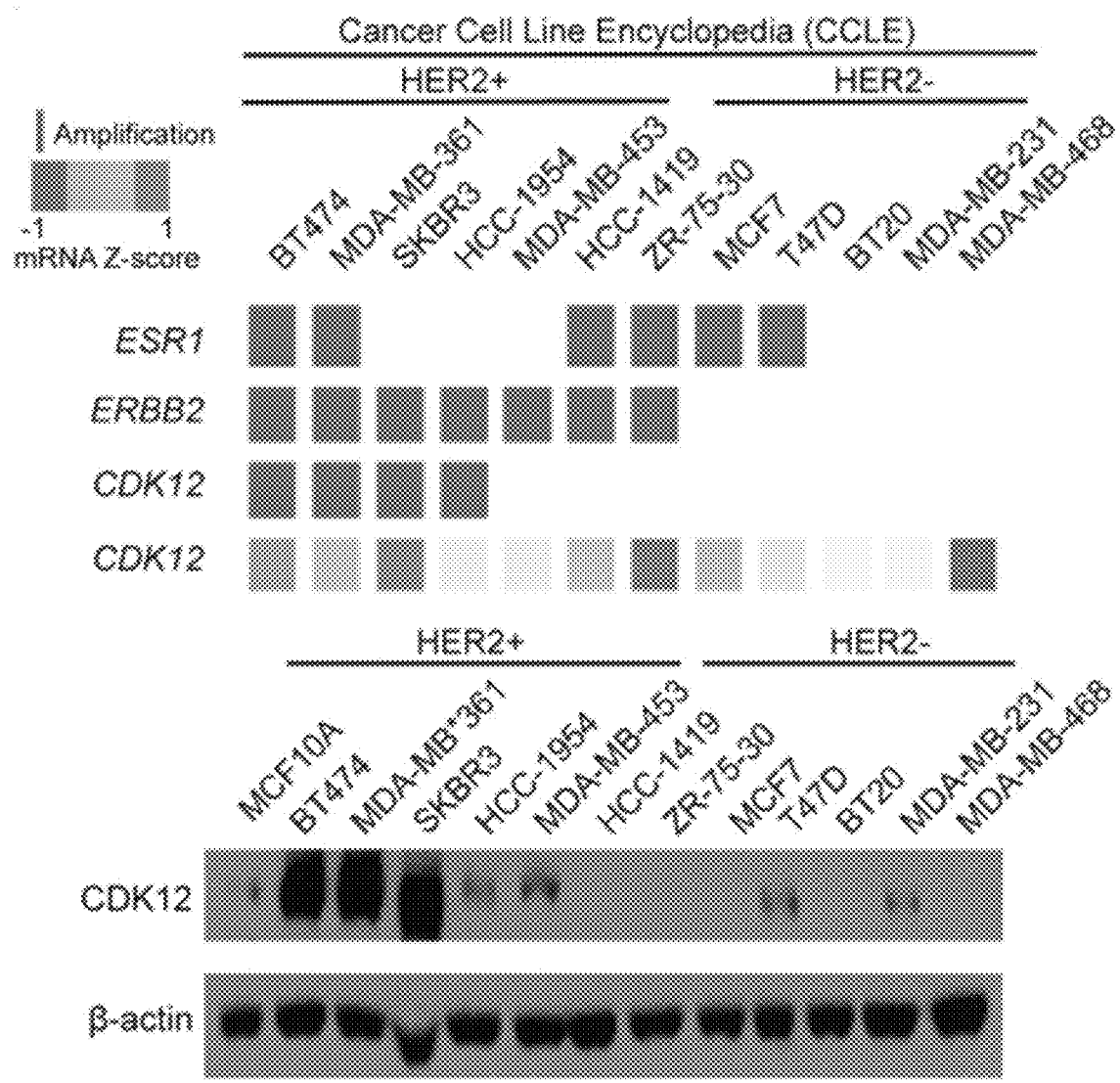
Figure 30A:
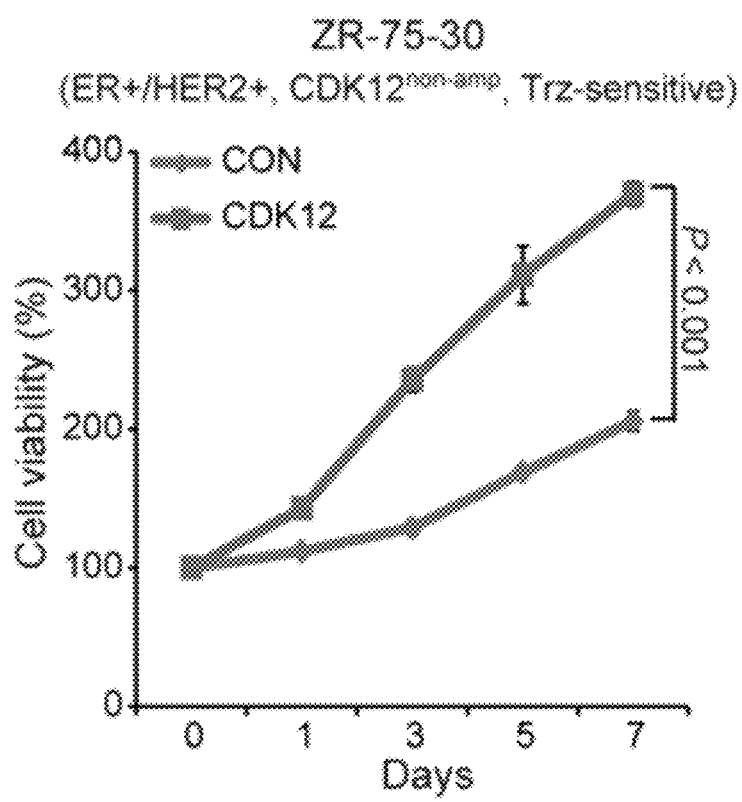
FIGS. 30A, 30B, 30C, 30D, 31A and 31B show that CDK12 promotes the growth of a tumor in HER2+ breast cancer.
Figure 30B:
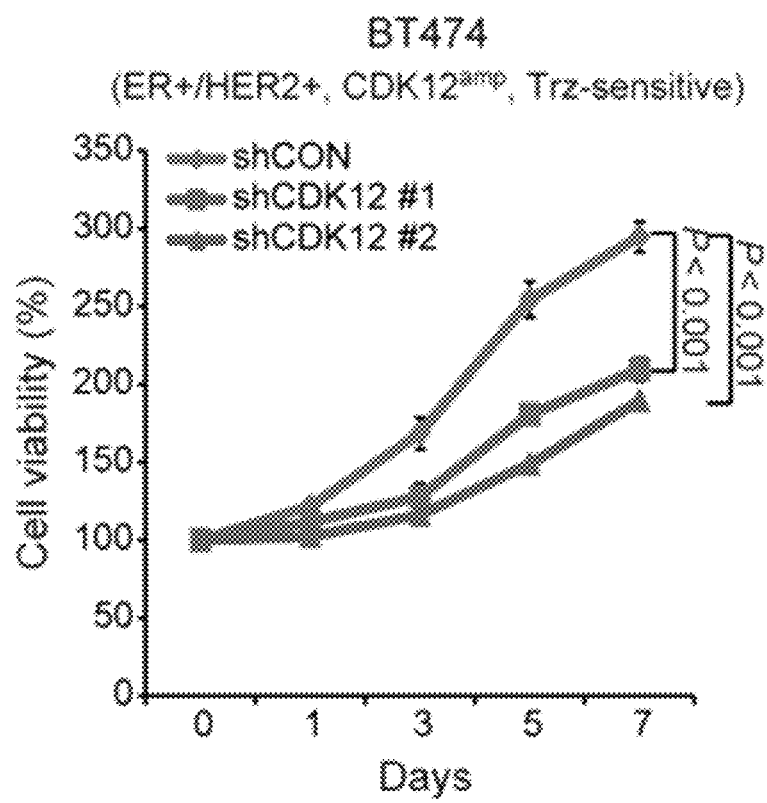
Figure 30C:
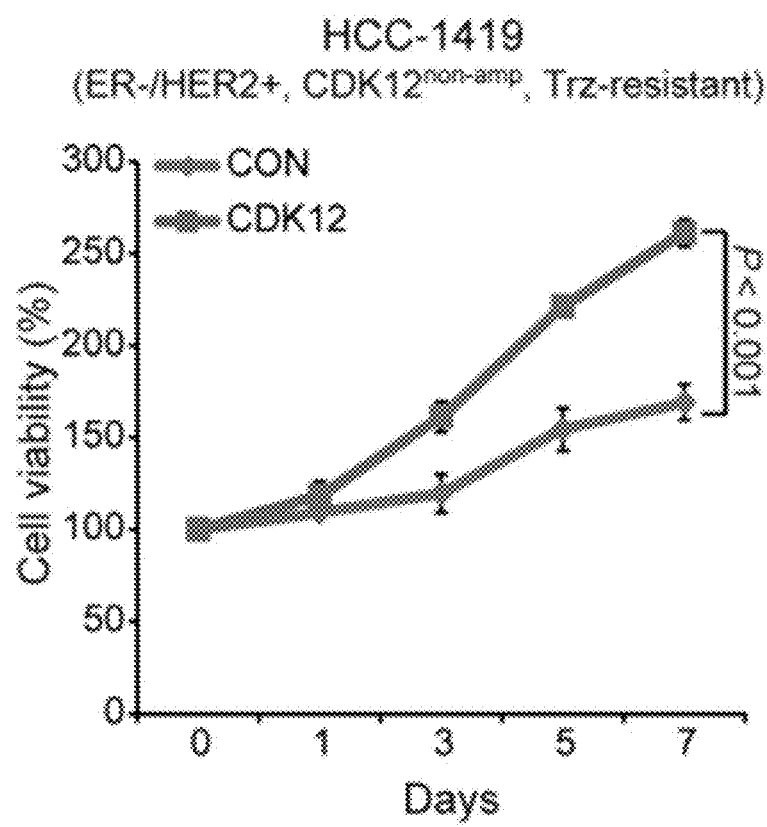
Figure 30D:
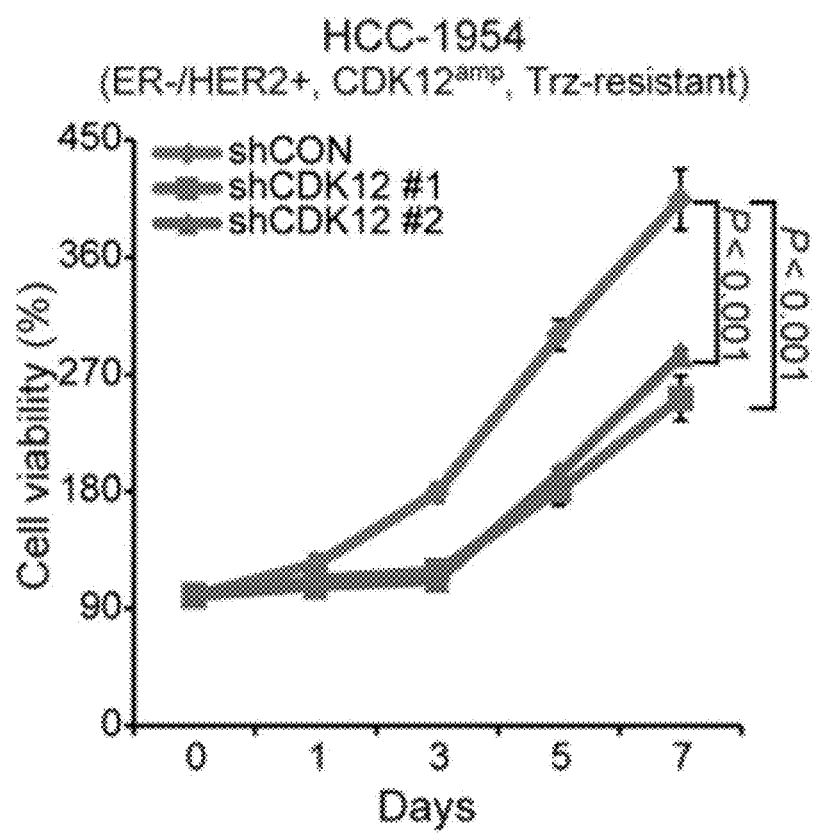
Figure 31A:
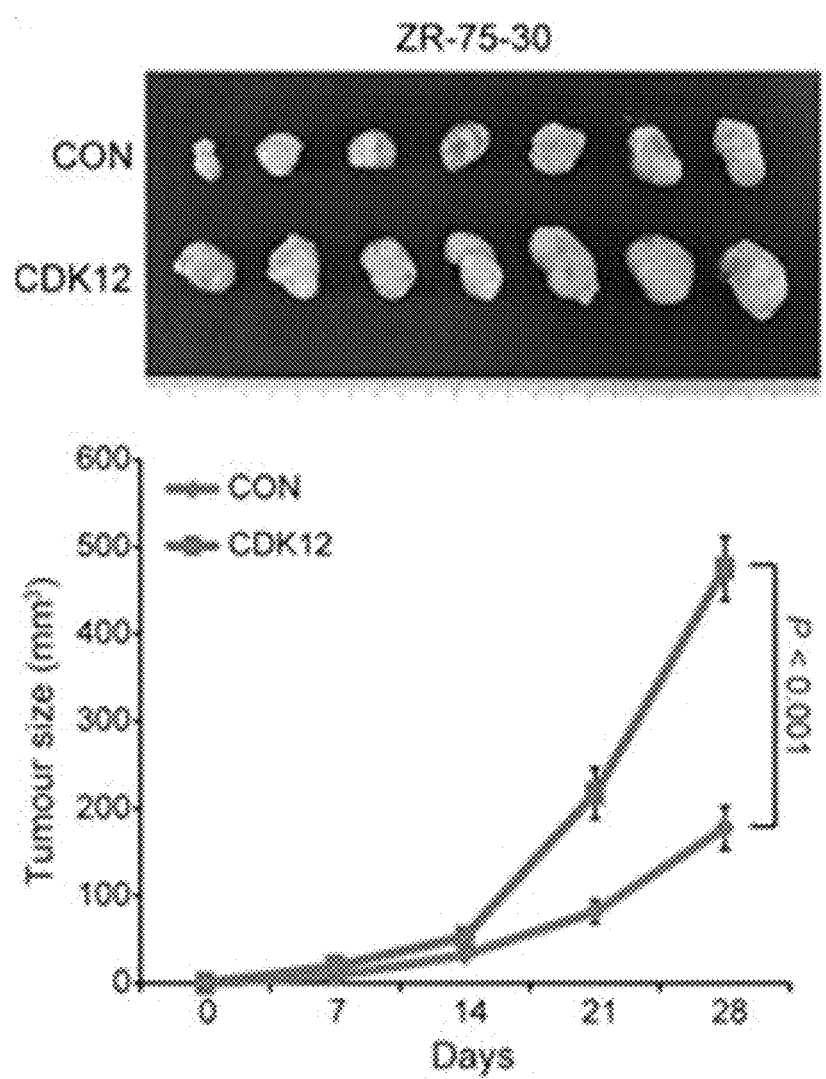
Figure 31B:
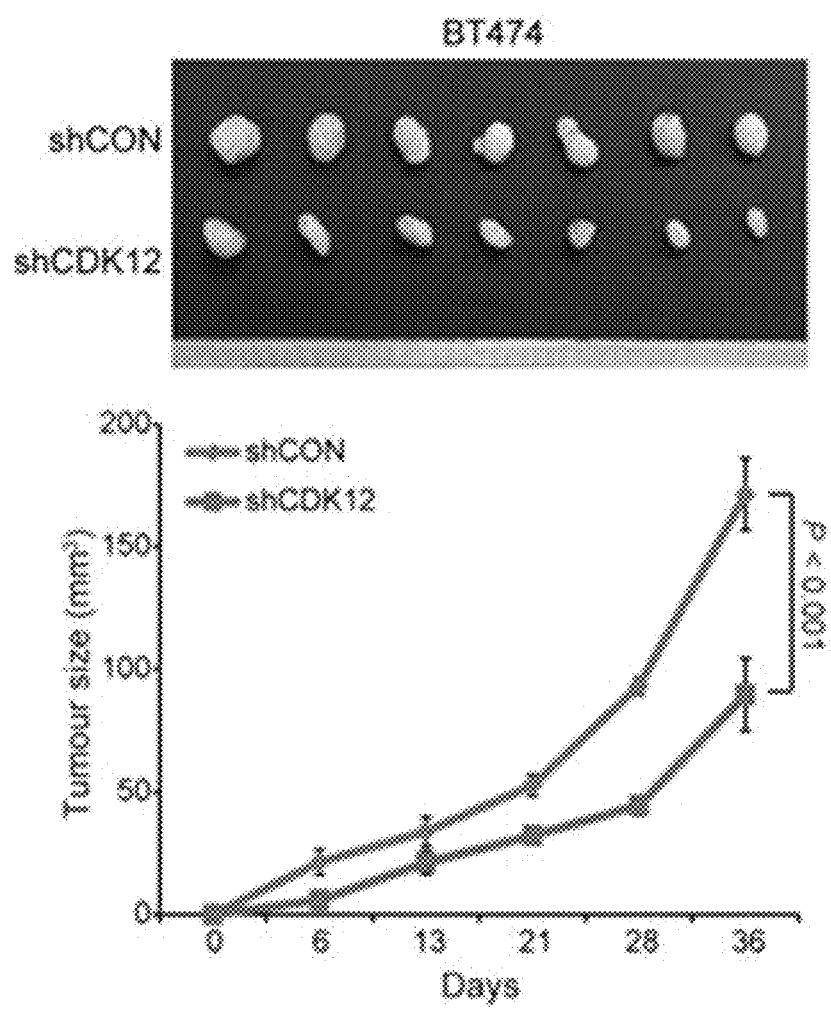
Figure 32A:
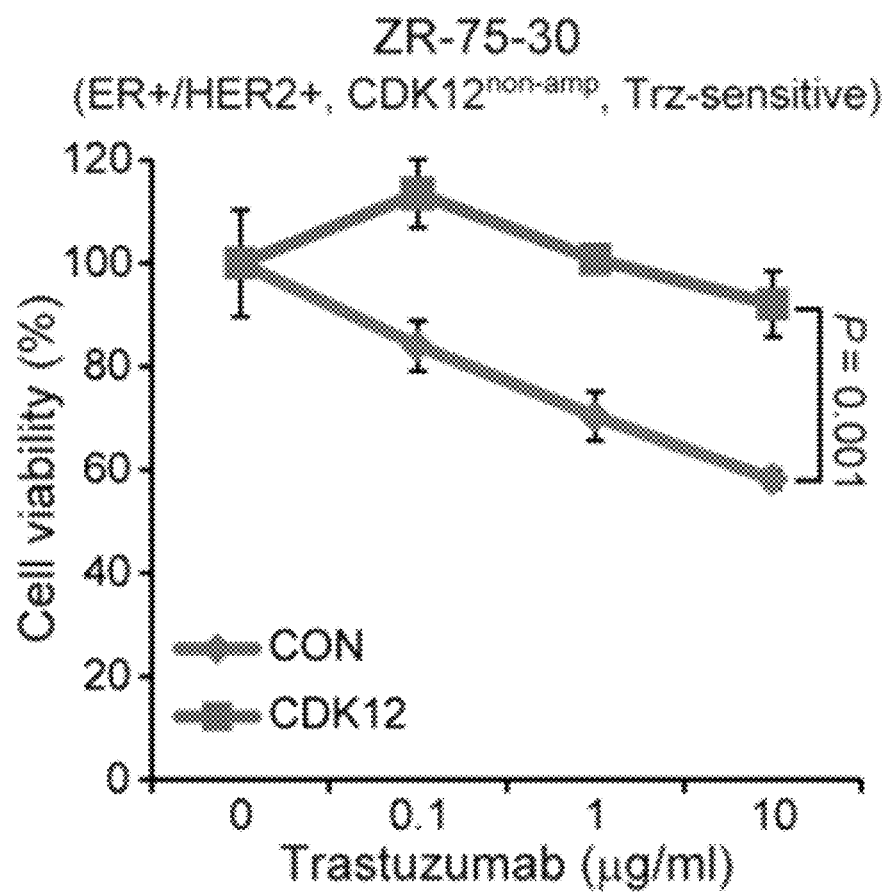
FIGS. 32A, 32B, 32C, 32D, 33A, 33B, 33C and 33D show the results showing an effect of CDK12 on reactivity of trastuzumab responsiveness in HER2+ breast cancer.
Figure 32B:
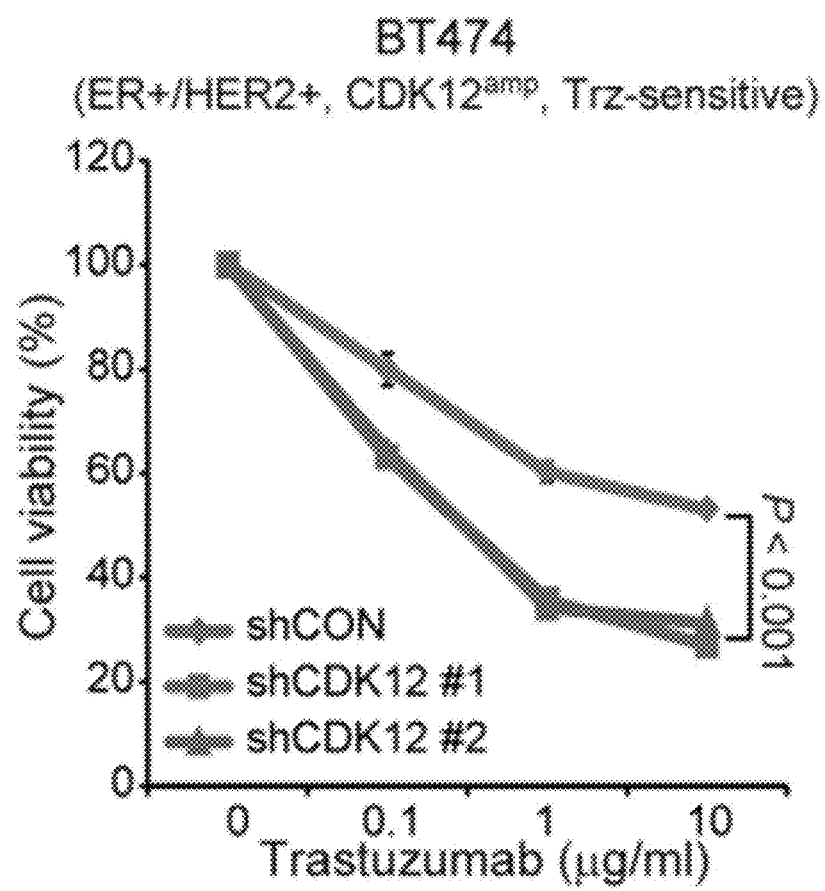
Figure 32C:
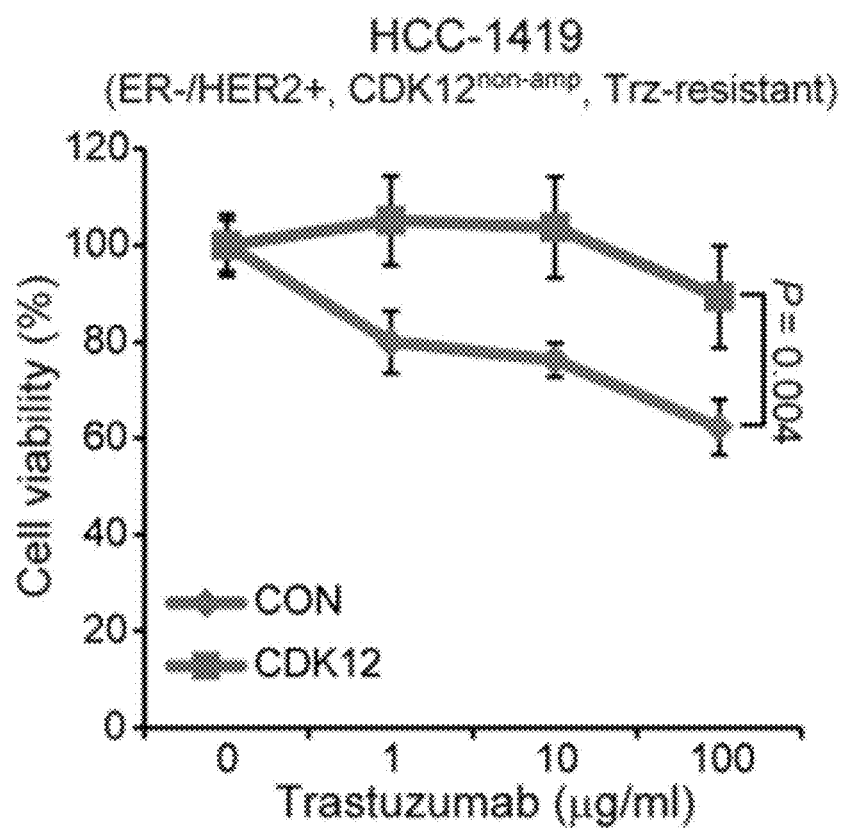
Figure 32D:
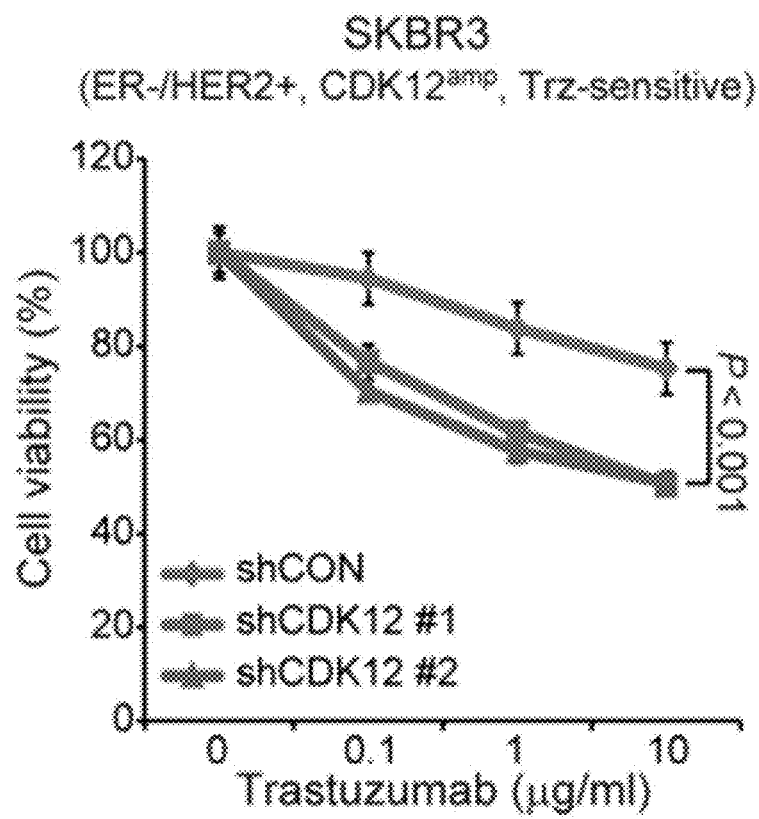
Figure 33A:
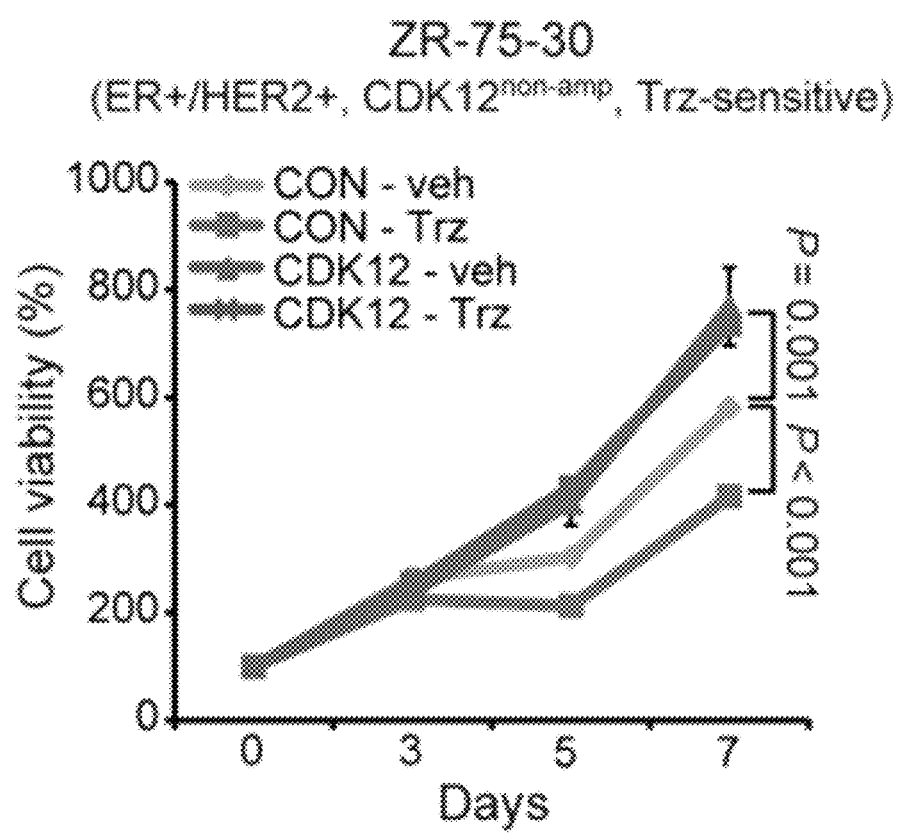
Figure 33B:
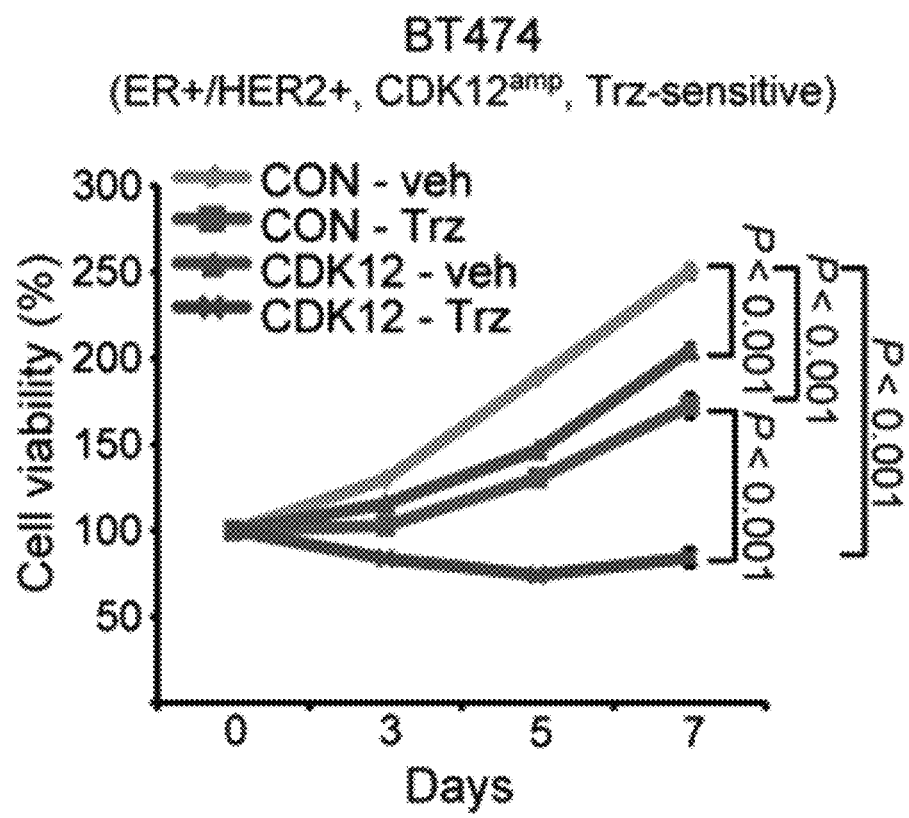
Figure 33C:
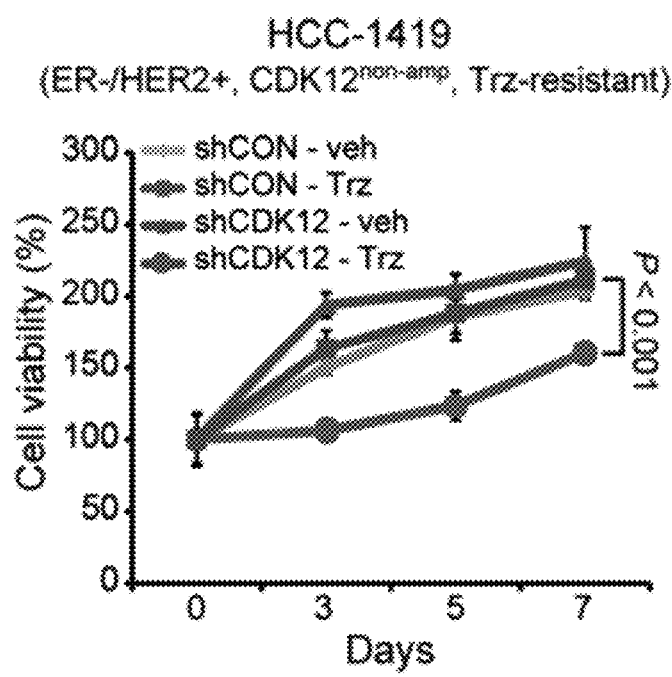
Figure 33D:
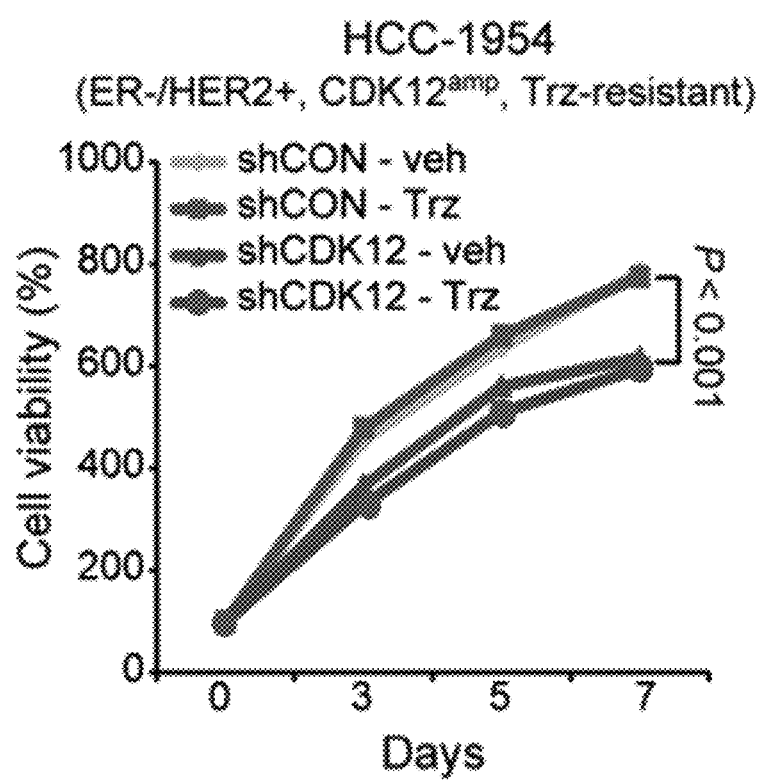
Figure 34:
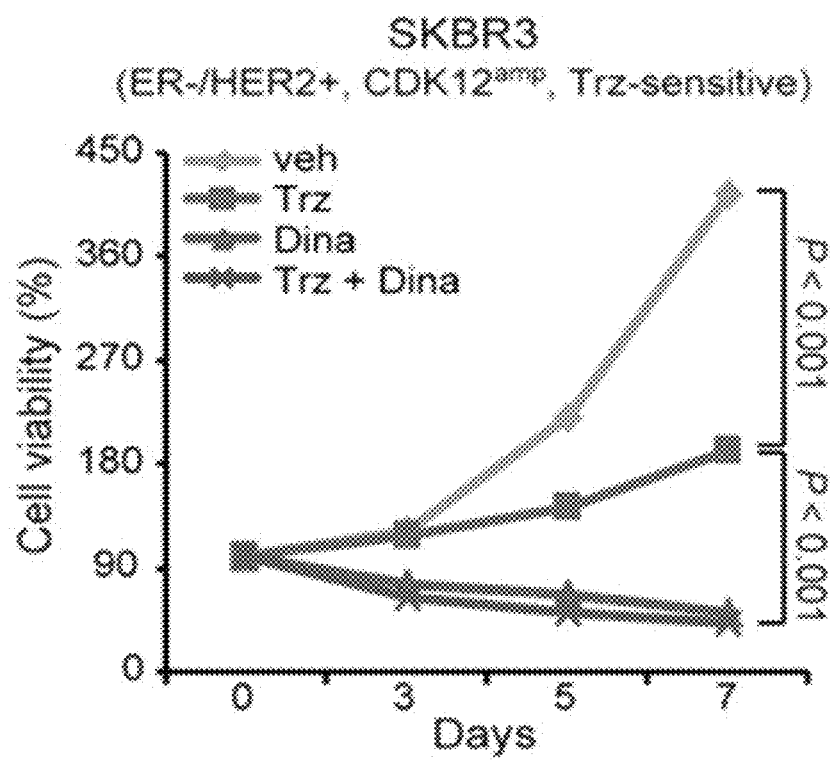
FIG. 34 shows the results of cell viability measured in the SKBR3 cells by SRB analysis after the SKBR3 cells are treated with 1 μg/mL trastuzumab (Trz) and/or 5 nM dinaciclib (Dina). Data is expressed as the mean±S.D. (n=3). The P-value was calculated by RM ANOVA using a post-hoc LSD test.
Figure 35A:
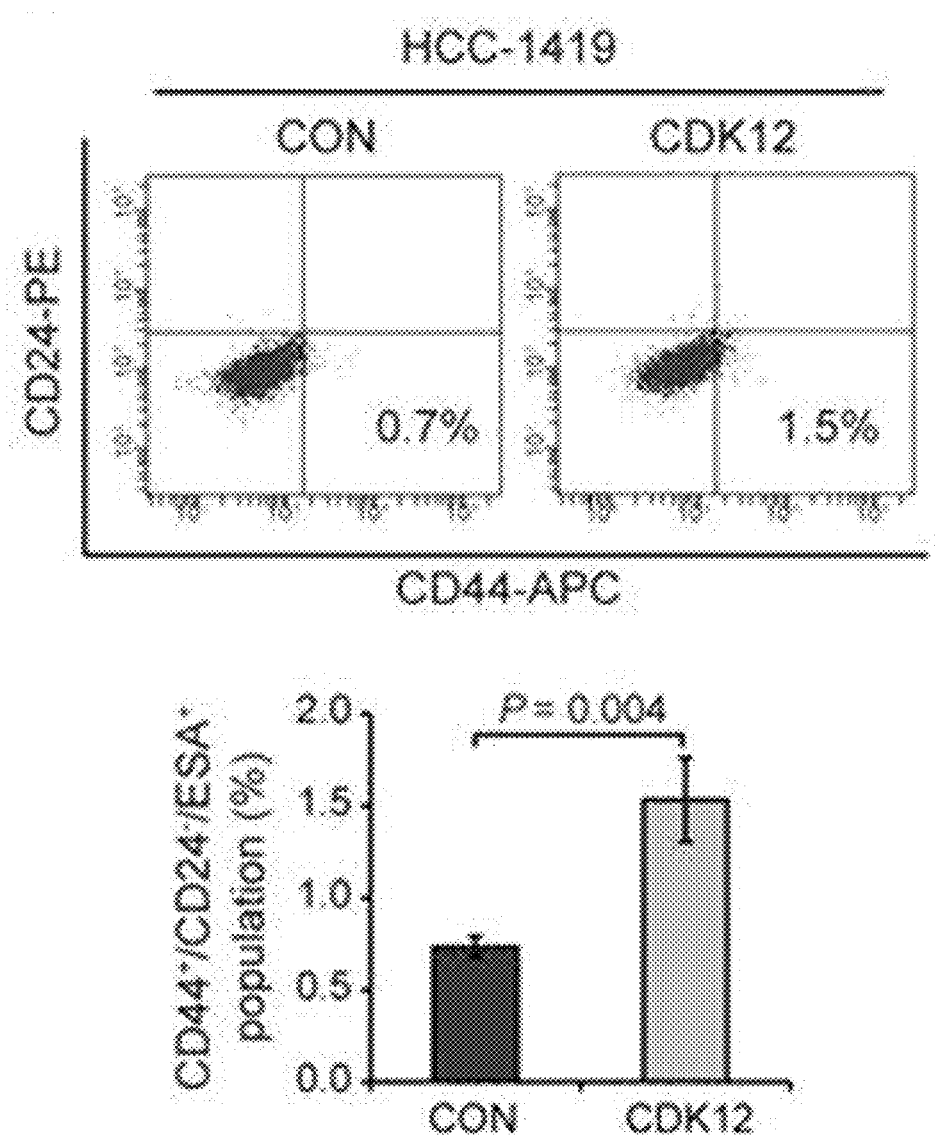
FIGS. 35A, 35B, 36A, and 36B show an effect of CDK12 on breast CSCs in HER2+ breast cancer.
Figure 35B:
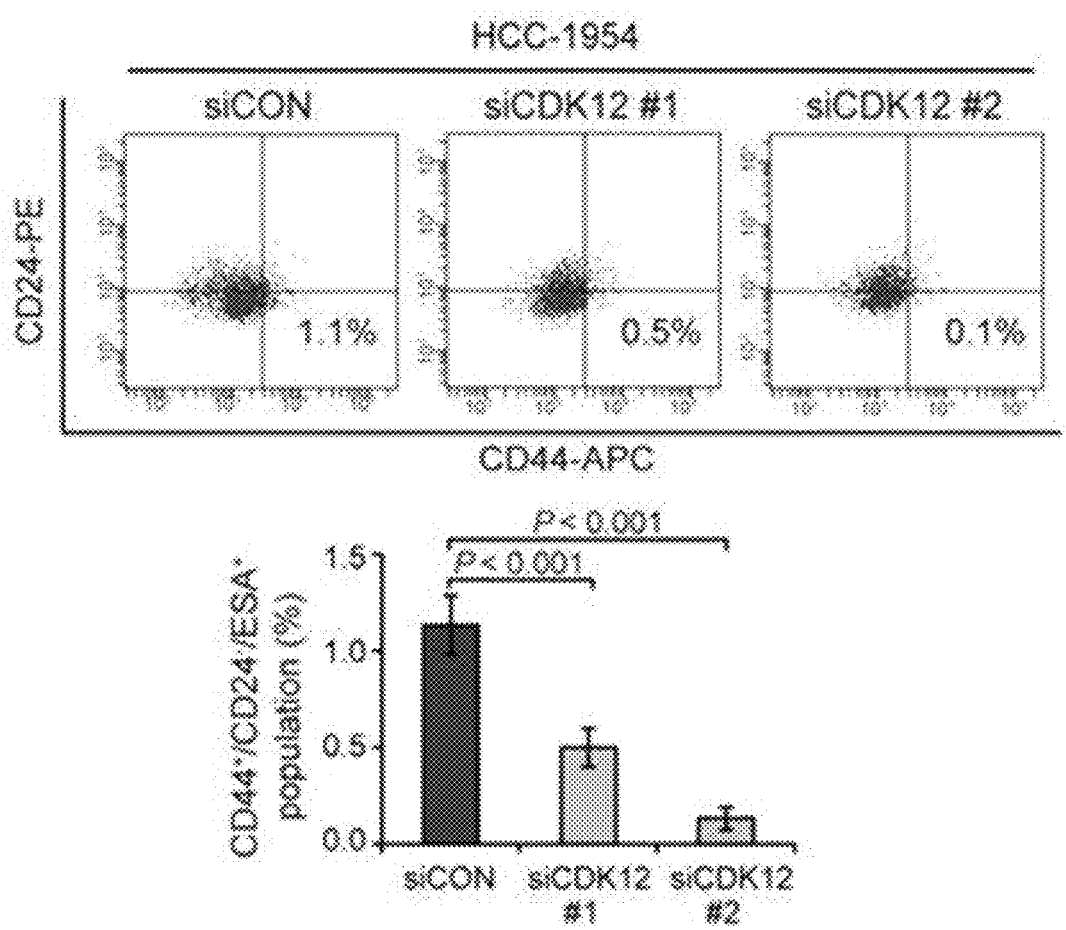
Figure 36A:
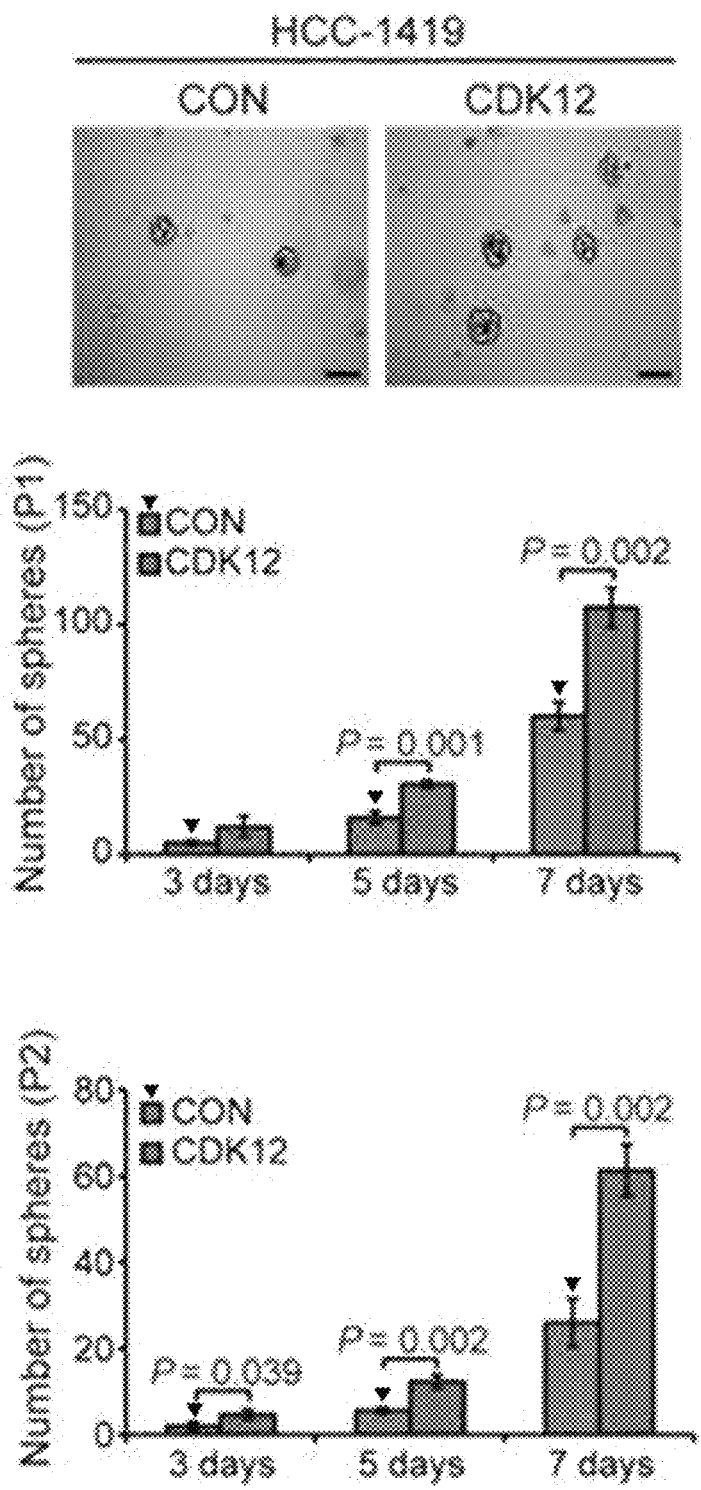
Figure 36B:
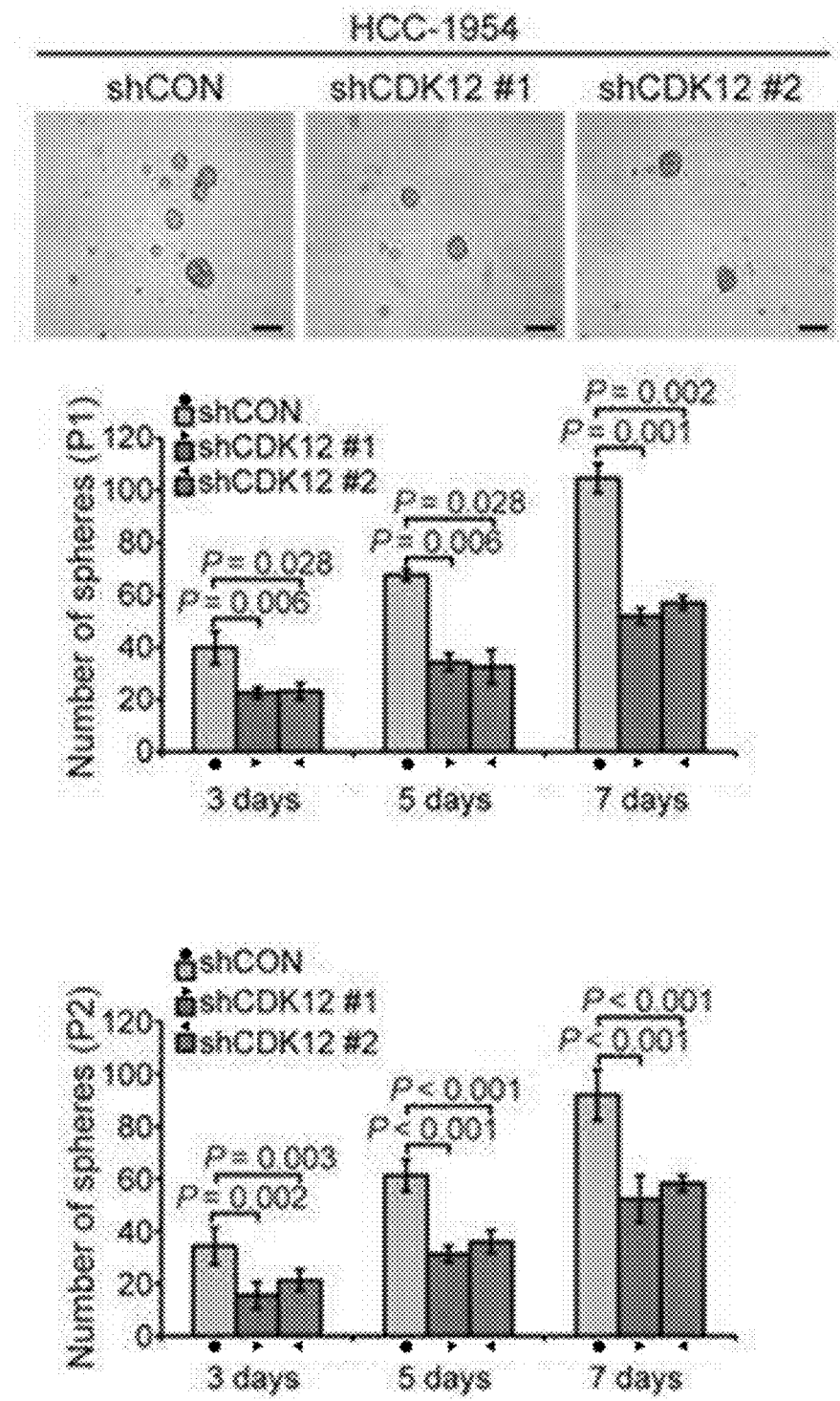

Among the genes having a poor prognostic outcome and unclear functions in HER2+ breast cancer, a potential role[12,19,20] of CDK12, which is a kinase associated with the phosphorylation of RNA PolII CTD often identified as a cancer target, was further confirmed in HER2+ breast cancer. Consistent with previous reports[8,13], it was found that approximately 90% of the HER2+ breast cancers had CDK12 amplification (FIG. 25). Also, CDK12 expression was highest in HER2+× breast cancer among breast cancer subtypes, and an enhanced level of CDK12 was associated with its gene amplification and HER2 expression (FIG. 2, FIG. 26 and FIG. 27). According to the METABRIC data sets and the Kaplan-Meier plotter (KM plotter, kmplot.com), CDK12 expression in breast cancer patients was associated with poor overall survival (OS) and disease-free survival (DFS; OS, P=0.015; DFS, P<0.001 in the METABRIC data sets; FIGS. 3A and 3C). Also, CDK12 was a well-established breast cancer prognostic index, that is, a Nottingham prognostic index (NPI)[26,27] and a separate prognostic factor (bcgenex.centregauducheau.fr)[29] having a high risk of metastatic relapse (MR) with respect to Adjuvant Online (AOL)[28] (FIG. 28). These results show that the genes in the chr17q12 amplicon are of clinical significance and CDK12 is suggested as a potential prognostic marker in the breast cancer.

[Experimental Example 2] Possibility of Targeting CDK12 Amplification in HER2+ Breast Cancer Next, it was examined whether or not high co-amplification levels of HER2+ and CDK12 functioned in various subgroups of HER2+ breast cancer. The lentiviral overexpression of CDK12 in an estrogen receptor (ER)+/HER2+ or ER−/HER2+ breast cancer cell line in which CDK12 expression was relatively low due to its non-amplification promoted cell growth, and also induced insensitivity to trastuzumab (FIGS. 29, 30A, 30B, 30C, 30D, 32A, 32B, 32C, 32D, 33A, 33B, 33C and 33D). In the trastuzumab-sensitive ER+/HER2+ or ER−/HER2+ breast cancer cells with CDK12 amplification, short-hairpin RNA (shRNA)-mediated CDK12 knockdown reduced cell growth, and also allowed the cells to respond to trastuzumab (FIGS. 29, 30A, 30B, 30C, 30D, 32A, 32B, 32C, 32D, 33A, 33B, 33C and 33D). In the trastuzumab-resistant HER2+ breast cancer cells with CDK12 amplification, CDK12 knockdown did not give sensitivity to trastuzumab, but induced delayed growth (FIGS. 33A, 33B, 33C and 33D). This data was confirmed in an orthotopic tumor xenograft model (FIGS. 5A, 5B, 31A and 31B). Also, the results of co-administration of trastuzumab and dinaciclib (CDK12 kinase inhibitor[24]) showed that the trastuzumab and dinaciclib had a significant anti-tumor effect in vitro and in vivo in the trastuzumab-sensitive HER2+ breast cancer cells (FIGS. 4A, 4B, 5A, 5B, and 34). In particular, dinaciclib monotherapy has an excellent anti-tumor effect in the HER2+ breast cancer cells having in vitro and in vivo resistance to trastuzumab (FIGS. 4A, 4B, 5A, and 5B), indicating that the dinaciclib targeted CDK12 in HER2+ breast cancer to overcome the resistance to trastuzumab therapy. Therefore, the above-described results suggest that CDK12 may be an effective therapeutic target in HER2+ breast cancer showing different hormone-receptor statuses and responses to trastuzumab.

[Experimental Example 3] Investigation of Role of CDK12 Kinase Activity in Transcriptional Upregulation of Genes that Promote a Tumor Signaling Pathway To determine how CDK12 regulated the tumor growth and trastuzumab responsiveness in HER2+ breast cancer, genome-wide CDK12-target genes were examined in CDK12-overexpressing ZR-75-30 cells using RNA-seq analysis.

Also, 500 to 10,000 ZR-75-30 control (CON) or CDK12-overexpressing cells (CDK12) were injected into fat pads of NOD/SCID mice using a limiting-dilution assay to confirm in vivo tumorigenicity. The tumor-initiating cell (TIC) frequency was calculated using L-Calc software. The results are shown in Table 1 below.

TABLE 1

| Cell Type | Injected Cell Counts | Days | | | |
|---|---|---|---|---|---|
| | | 7 | 14 | 21 | 28 |
| ZR-75-30- CON | 500 | 0/7 | 0/7 | 0/7 | 0/7 |
| | 1,000 | 0/7 | 0/7 | 0/7 | 0/7 |
| | 5,000 | 0/7 | 0/7 | 3/7 | 3/7 |
| | 10,000 | 0/7 | 3/7 | 7/7 | 7/7 |
| TIC Frequency | | | 1/33,250 | 1/6,315 | 1/6,315 |
| | | | (1/10,907- | (1/3,368- | (1/3,368- |
| | | | 1/101,364) | 1/11,839) | 1/11,839) |
| ZR-75-30- CDK12 | 500 | 0/7 | 0/7 | 0/7 | 3/7 |
| | 1,000 | 0/7 | 0/7 | 4/7 | 7/7 |
| | 5,000 | 0/7 | 4/7 | 7/7 | 7/7 |
| | 10,000 | 2/7 | 7/7 | 7/7 | 7/7 |
| TIC Frequency | | 1/52,592 | 1/5,327 | 1/1,619 | 1/504 |
| | | (1/13,338- | (1/2,887- | (1/834- | (1/257- |
| | | 1/207,374) | 1/9,829) | 1/3,145) | 1/987) |
| P | | | 0.0048 | 0.0036 | 0.0001 |

This experiment was performed in the same manner as described above, except that different cells were used instead of the CDK12-overexpressing cells, in order to determine whether or not CDK12 knockdown in HER2+ breast cancer with CDK12 amplification had an inhibitory effect on in vivo tumorigenicity. 5,000 to 100,000 BT474 cells transfected with control shRNA (shCON) or CDK12-suppressing shRNA (shCDK12) were injected into fat pads of the NOD/SCID mice, and the TIC frequency was calculated using L-Calc software.

TABLE 2

| Cell Type | Injected Cell Counts | Days | | | | |
|---|---|---|---|---|---|---|
| | | 6 | 13 | 21 | 28 | 36 |
| BT474 shCON | 5000 | 0/7 | 0/7 | 1/7 | 3/7 | 5/7 |
| | 10,000 | 1/7 | 3/7 | 3/7 | 4/7 | 5/7 |
| | 50,000 | 1/7 | 6/7 | 7/7 | 7/7 | 7/7 |
| | 100,000 | 5/7 | 7/7 | 7/7 | 7/7 | 7/7 |
| TIC Frequency | | 1/119,832 | 1/25,420 | 1/16,559 | 1/10,151 | 1/5,893 |
| | | (1/56,942- | (1/13,702- | (1/8,544- | (1/5,075- | (1/2,996- |
| | | 1/252,180) | 1/47,158) | 1/32,091) | 1/20,304) | 1/11,589) |
| BT474 shCDK12 | 5,000 | 0/7 | 0/7 | 0/7 | 1/7 | 2/7 |
| | 10,000 | 0/7 | 0/7 | 0/7 | 0/7 | 3/7 |
| | 50,000 | 0/7 | 0/7 | 2/7 | 6/7 | 6/7 |
| | 100,000 | 1/7 | 5/7 | 7/7 | 7/7 | 7/7 |

TABLE 2-continued

| Cell Type | Injected Cell Counts | Days | | | | |
|---|---|---|---|---|---|---|
| | | 6 | 13 | 21 | 28 | 36 |
| TIC Frequency | | 1/1,104,245 (1/157,095- 1/7,761,907) | 1/176,298 (1/74,940- 1/414,747) | 1/74,865 (1/39,049- 1/143,530) | 1/32,937 (1/18,032- 1/60,161) | 1/5,893 (1/2,996- 1/11,589) |
| P | | | 0.0048 | 0.0036 | 0.0001 | 0.0001 |

Figure 8:
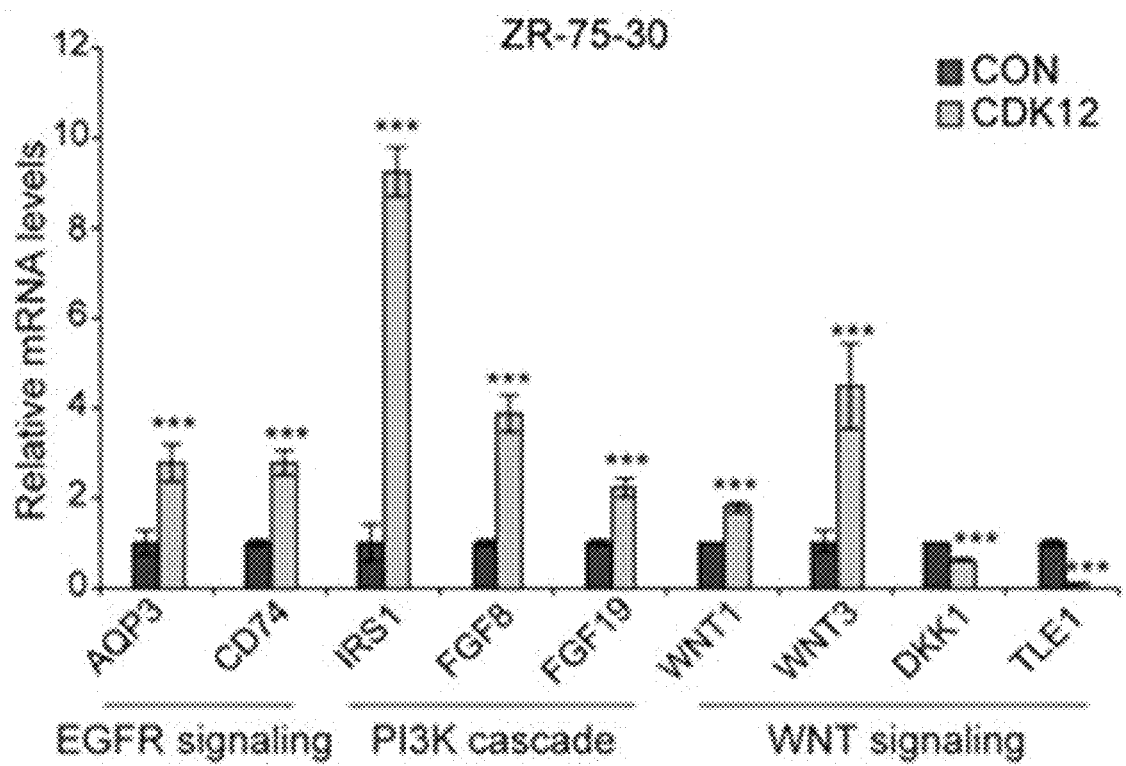
Figure 9:
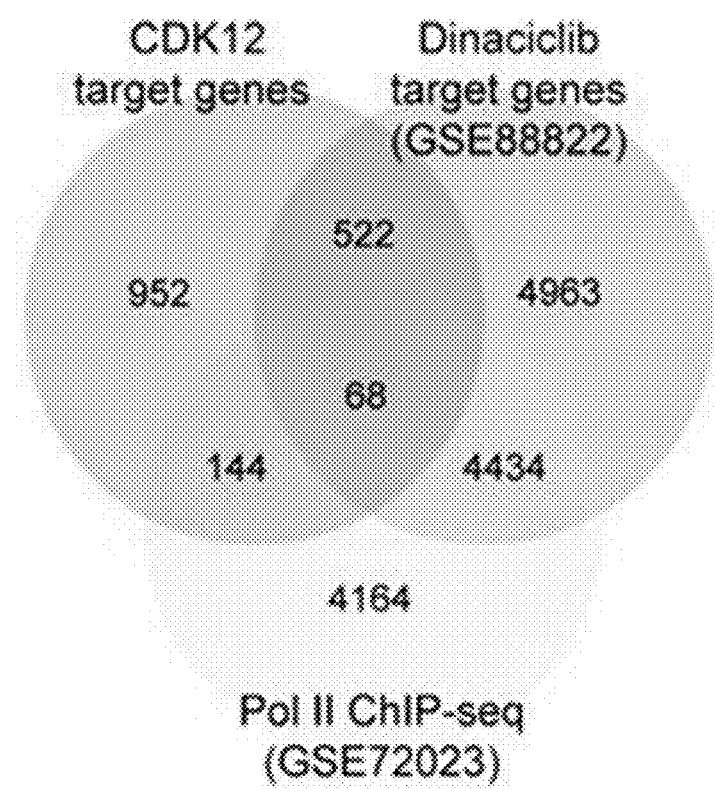
Figure 10A:
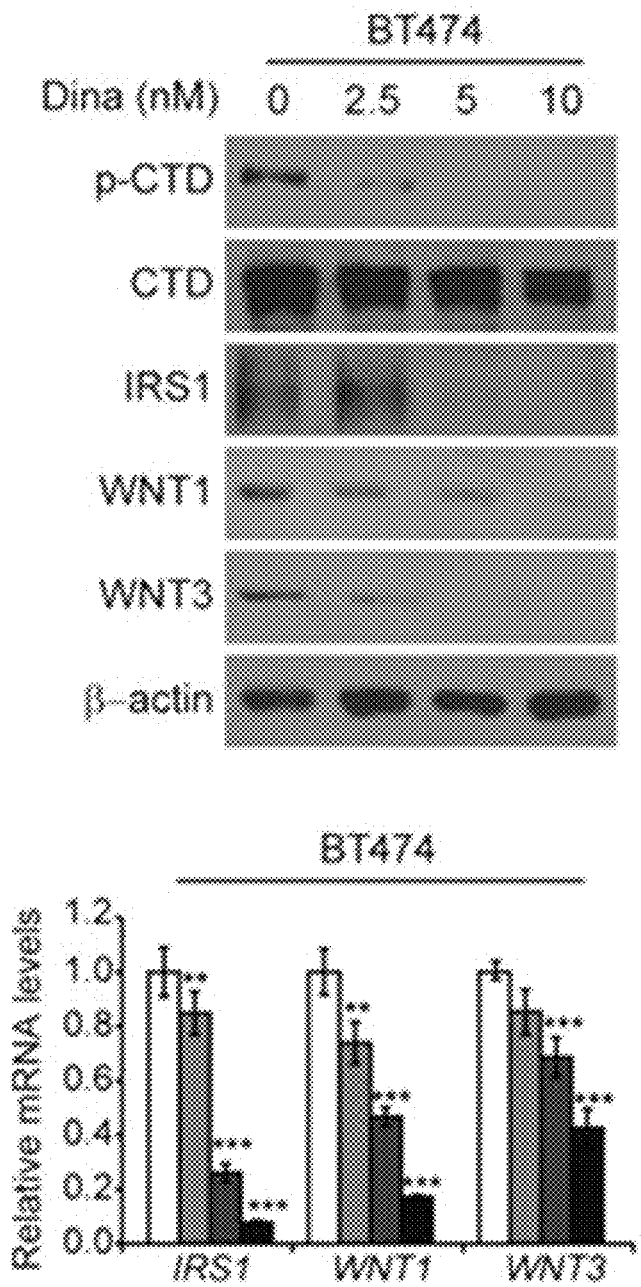
Figure 10B:
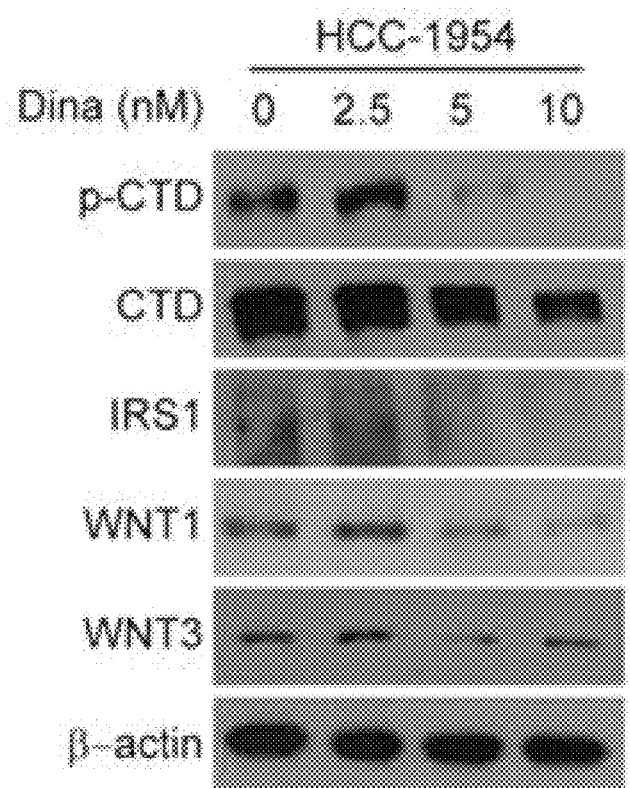
Figure 10B:
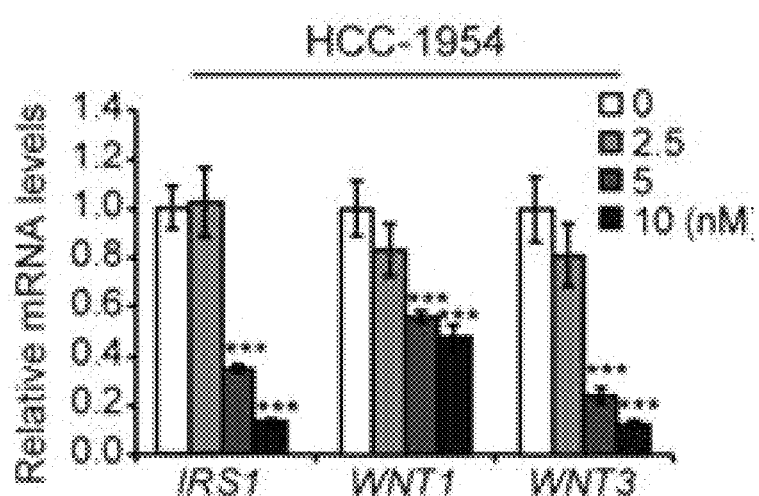
Figure 11A:
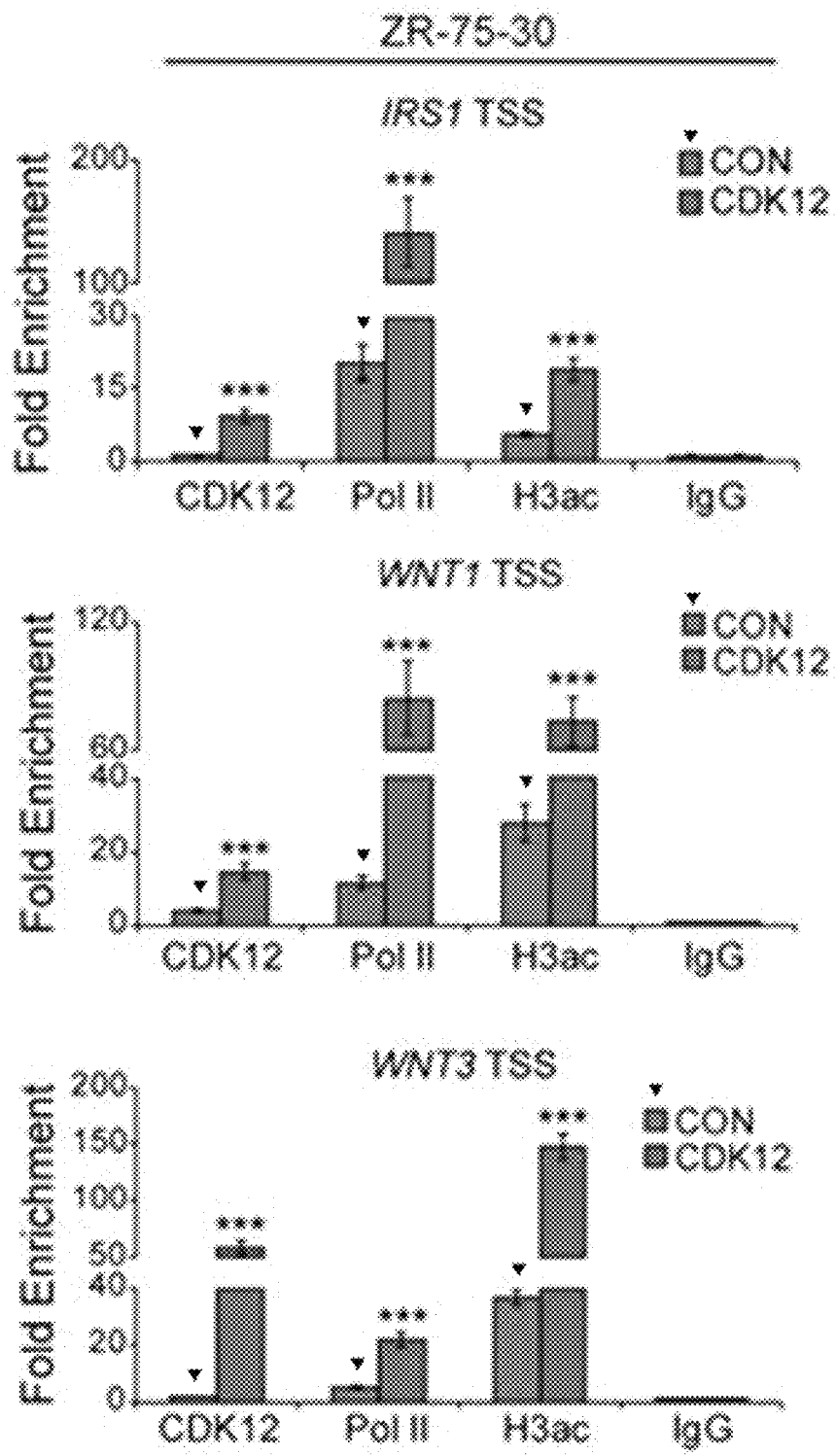
Figure 11B:
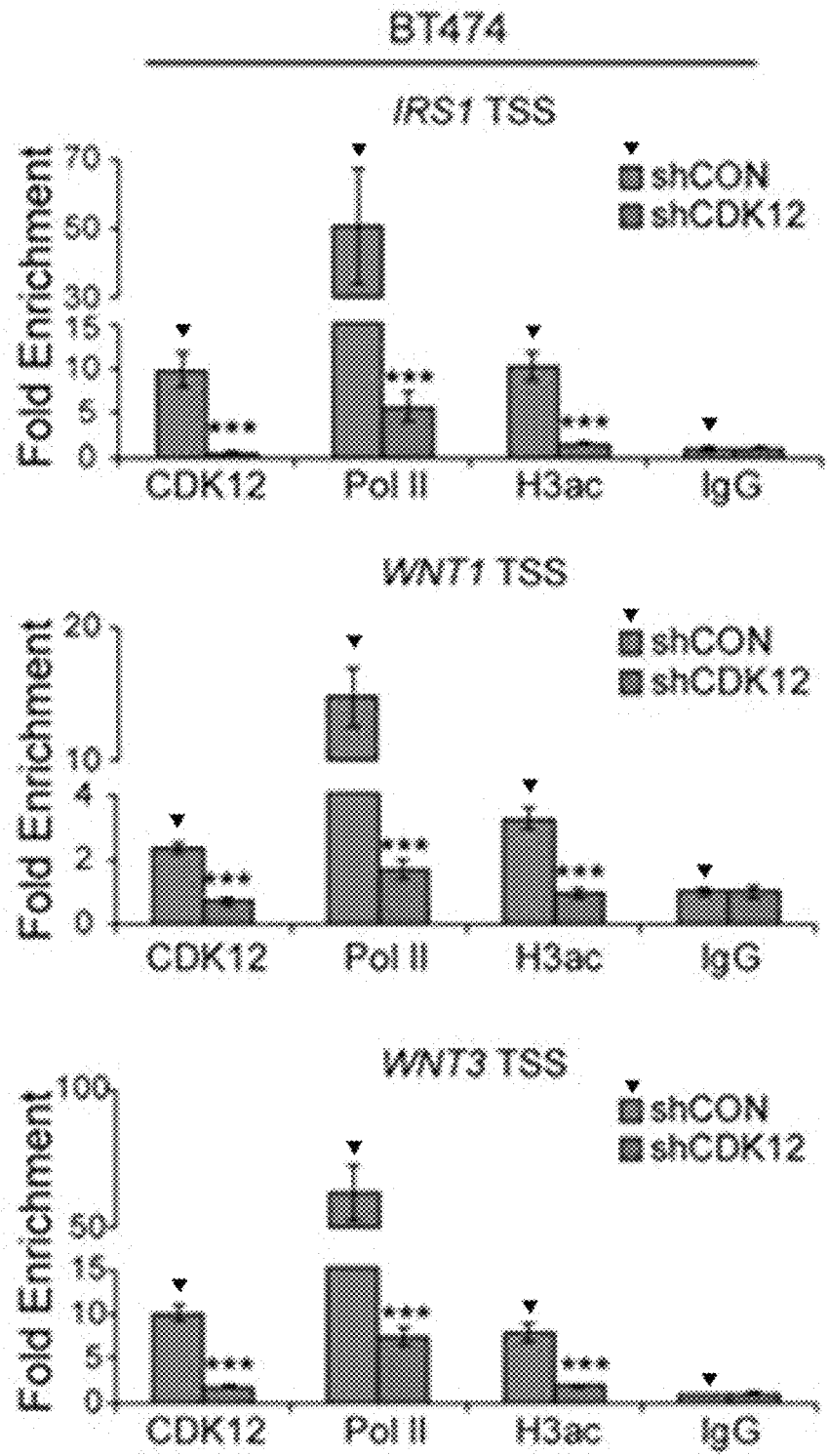
Figure 12A:
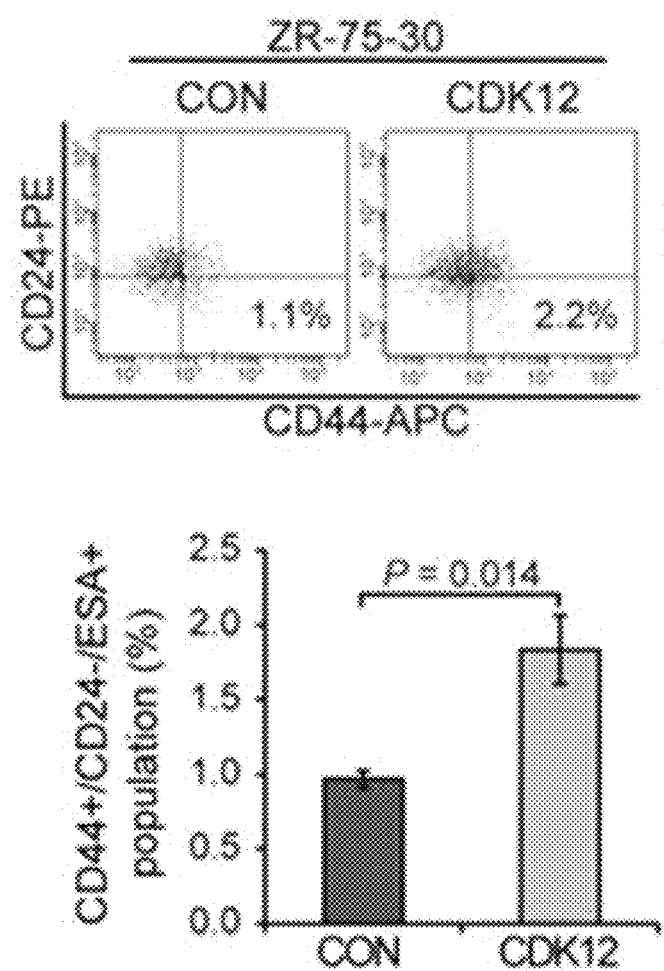
FIGS. 12A, 12B, 13A, 13B, 14, 15A, 15B, 16A, 16B, 17A, 17B, and 18 show that CDK12 regulates the cancer sternness and a WNT/β-catenin signaling pathway by upregulating a WNT ligand in HER2+ breast cancer.
Figure 12B:
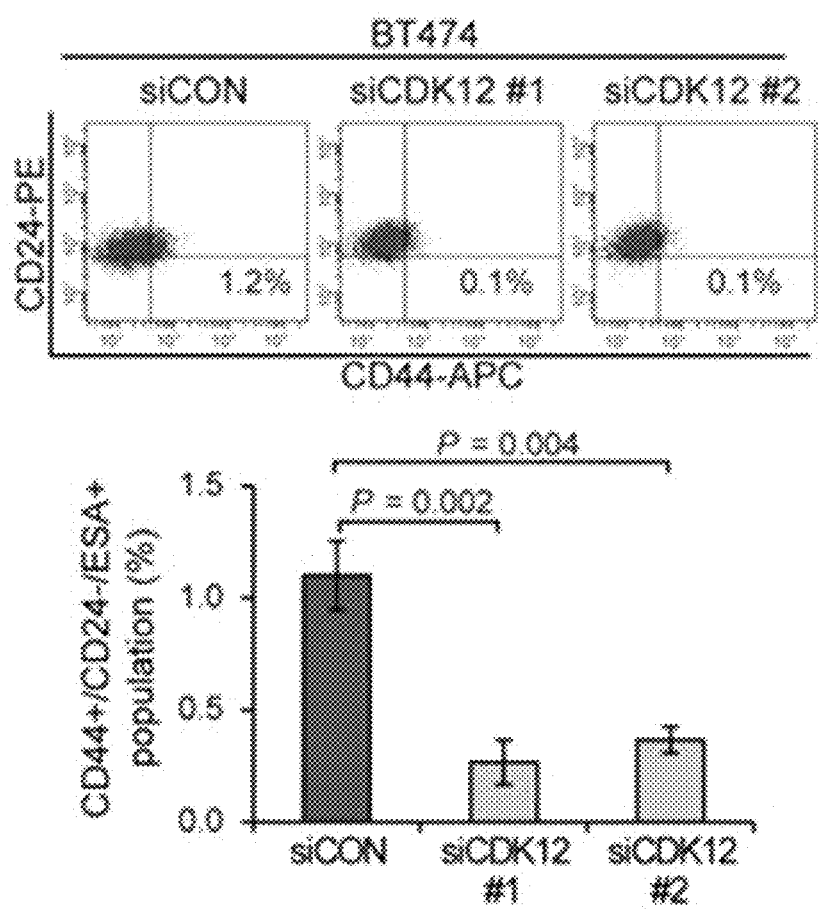
Figure 13A:
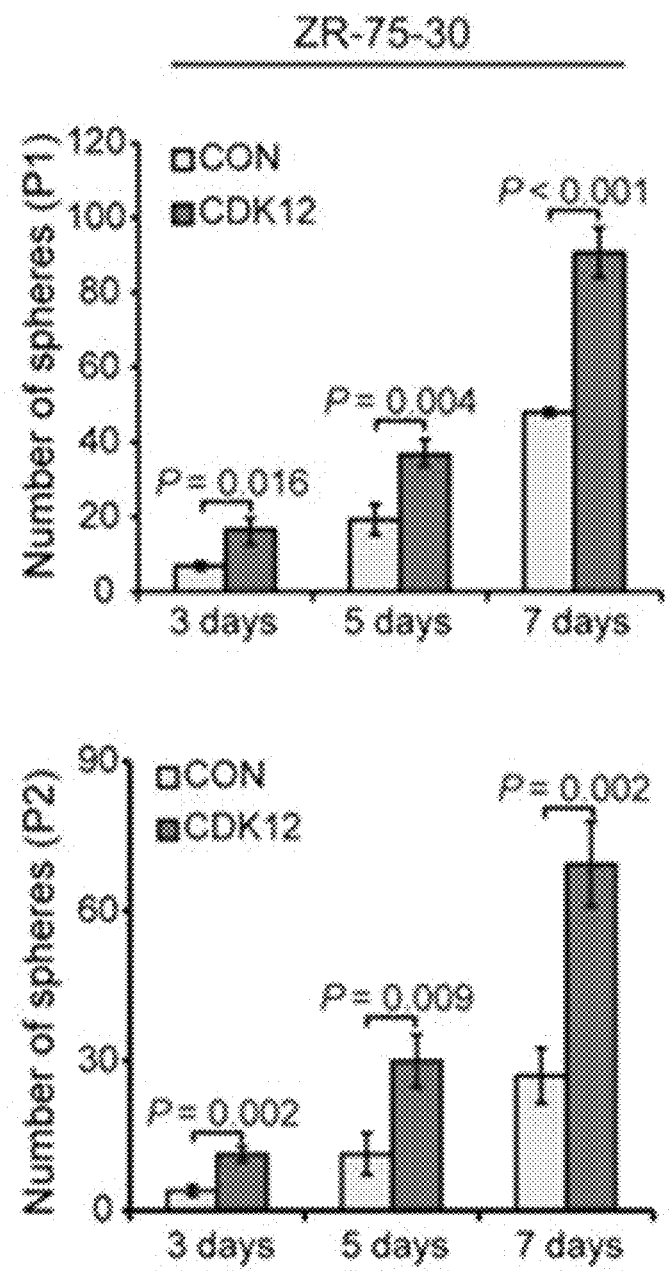
Figure 13B:
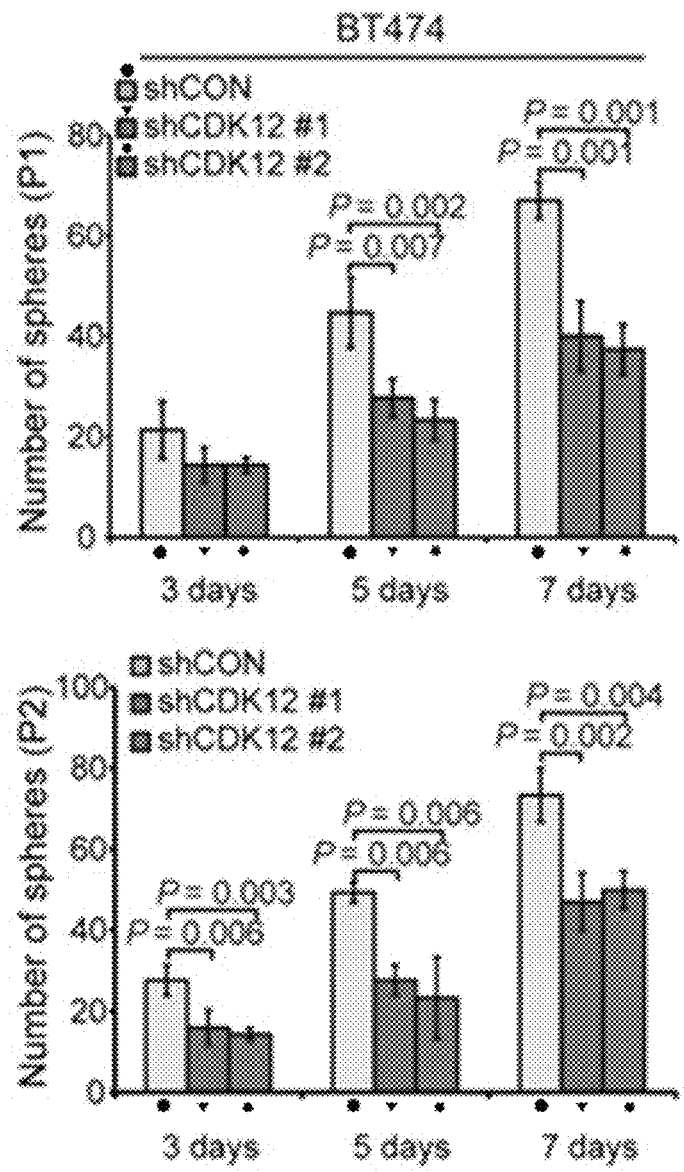

The expression levels of the genes differentially expressed in the presence of CDK2 overexpression were further enhanced in some tumor signaling cascades such as an epidermal growth factor receptor (EGFR) signaling, a phosphoinositide 3-kinase (PI3K) cascade, and a WNT signaling pathway (FIGS. 2A and 2B, Table 1). The changes in expression of these genes were verified by quantitative reverse transcription polymerase chain reaction (qRT-PCR) (FIG. 8). Also, the CDK12-target genes associated with the enzymatic activity for PolII CTD phosphorylation, which includes an ErbB-PI3K-AKT regulatory factor insulin receptor substrate 1 (IRS1) and several WNT ligands, were confirmed by comparative analysis of the gene-expression microarray data obtained from breast cancer cells treated with dinaciclib[24] and PolII chromatin immunoprecipitation (ChIP) data obtained from cells treated with a recently developed CDK12inhibitor 'THZ-531'[30] with RNA-seq data (FIG. 9). Consistently, the treatment with dinaciclib reduced the expression of IRS1, WNT1, and WNT3 at a transcriptional level in a dose-dependent manner in the trastuzumab-sensitive and -resistant HER2+ breast cancer cells (FIGS. 10A and 10B). Also, ChIP assay results showed that CDK12 and PolII were gathered together around transcription start sites (TSS) of IRS1, WNT1, and WNT3 (FIGS. 11A and 11B). At the target loci, the acetylation of histone H3 was also enhanced, indicating that the transcription of these genes was activated by CDK12 and PolII (FIGS. 11A and 11B). Therefore, the above-described results show that the CDK12 kinase activity is important for transcriptional regulation of the genes involved in EGFR-, PI3K- and WNT-signaling cascades in HER2+ breast cancer.

[Experimental Example 4] Effect of CDK12 on WNT/β-Catenin Signal Transduction and Cancer Stemness Enhancement in HER2+ Breast Cancer Because WNT ligands WNT1 and WNT3 are involved in mammary tumorigenesis, stem cell-like traits, or resistance to trastuzumab in breast cancers, an effect of CDK12 on cancer stem cell (CSC) activity in HER2+ breast cancer was evaluated. Fluorescence-activated cell sorting (FACS) analysis of differentiation clusters of CD44+/CD24−/epithelial-specific antigen (ESA+) partial subpopulations and tumorspheres showed that CDK12 overexpression enhanced the self-renewal of CSC-like populations, but CDK12 knockdown reduced formation of CSC populations and spheres in various types of HER2+ breast cancer cells including both trastuzumab-sensitive and -resistant cell lines (FIGS. 12A, 12B, 13A, 13B, 35A, 35B, 36A, and 36B). Consistent with the in vitro results, it was revealed that tumorigenesis was promoted in orthotopically xenografted mice having CDK12-overexpressing ZR-75-30 cells, which indicated that the mice having CDK12-knockdown BT474 cells had an impaired tumor-initiating ability (Tables 1 and 2). These results show that CDK12 enhances the self-renewal and tumorigenesis of CSCs in HER2+ breast cancer.

Figure 14:
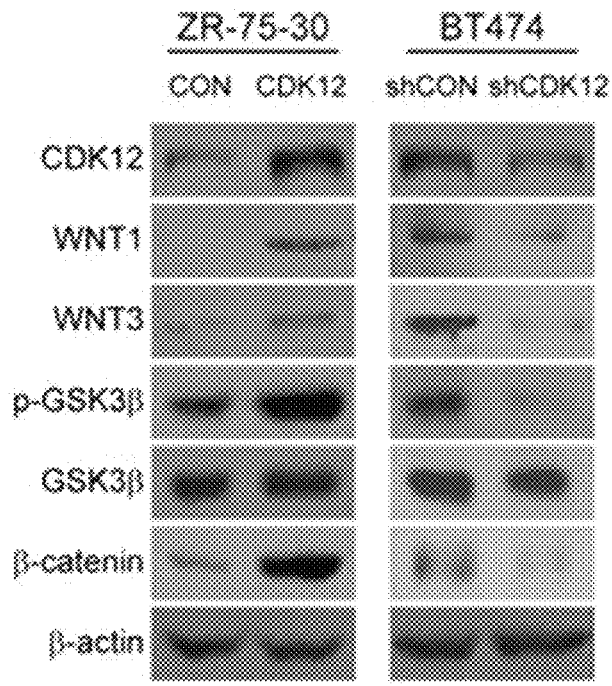
Figure 14:
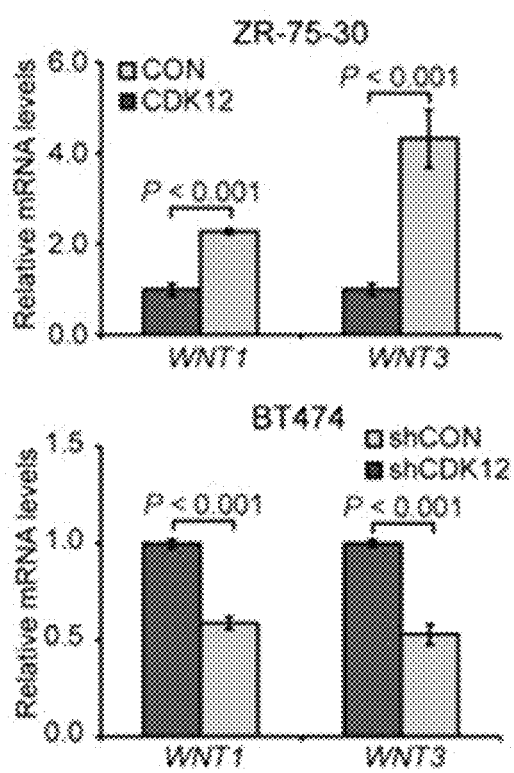
Figure 15A:
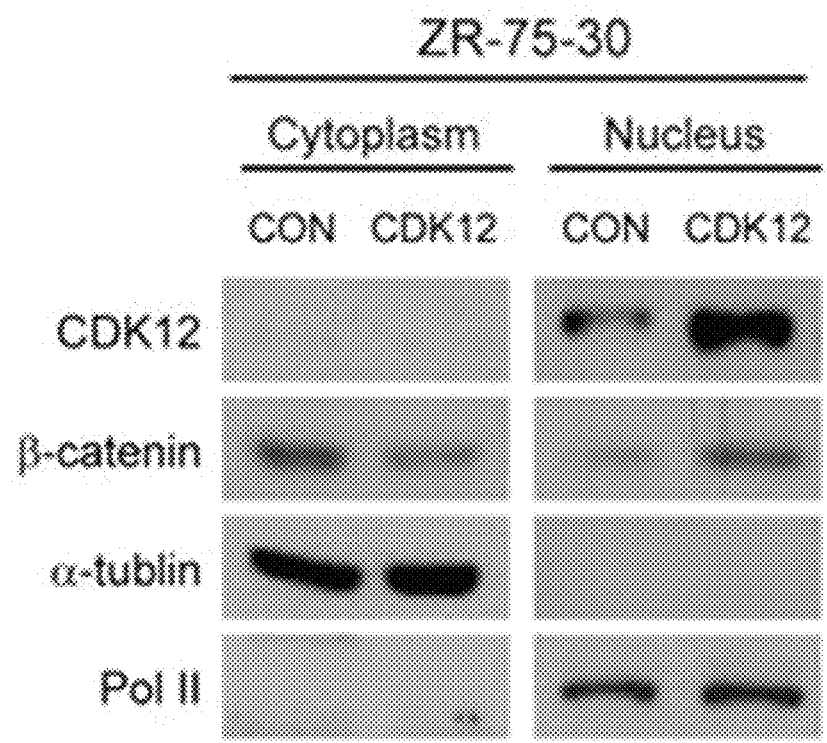
Figure 15B:
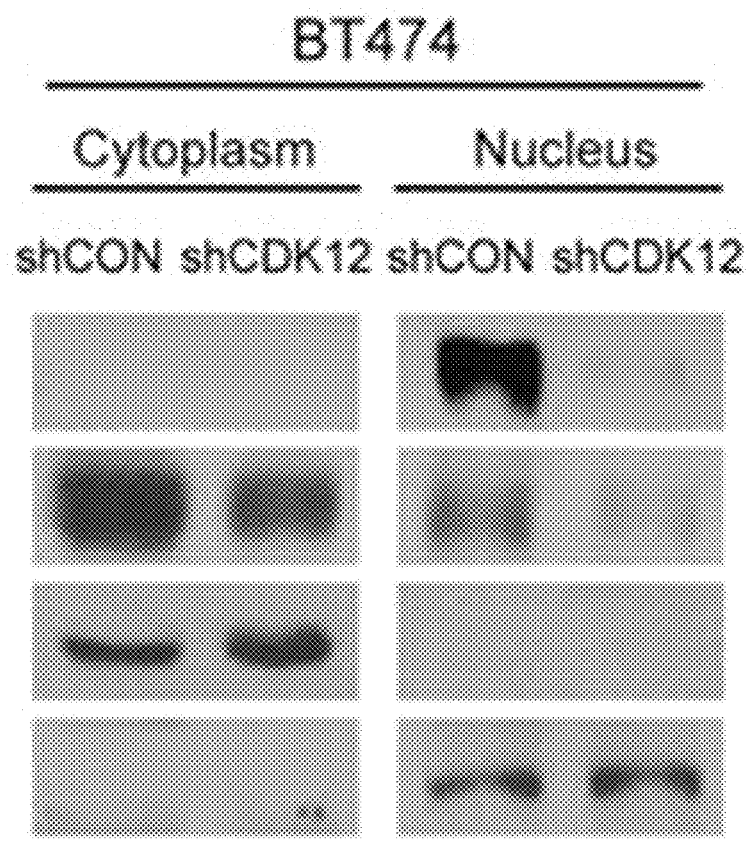
Figure 16A:
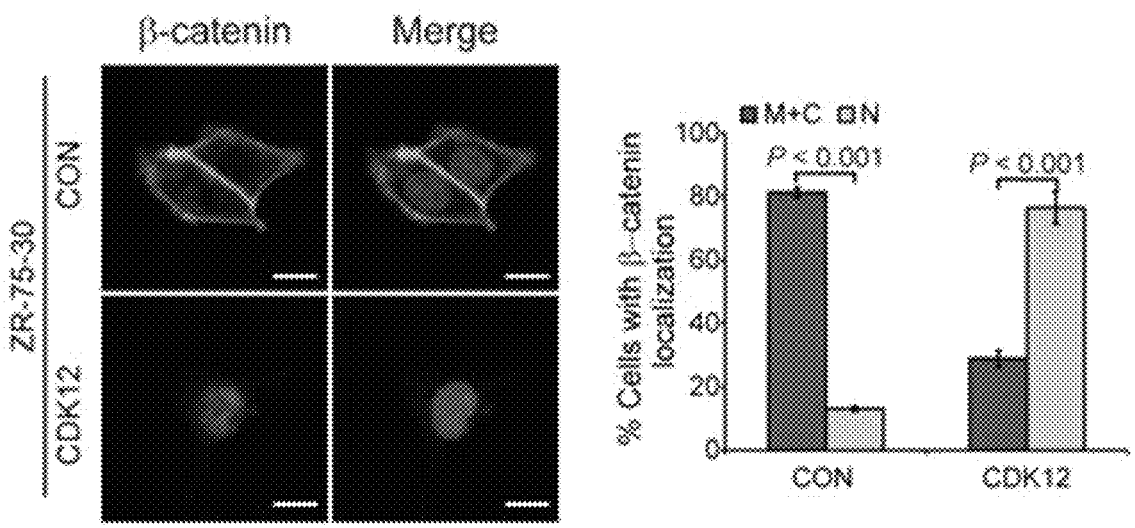
Figure 16B:
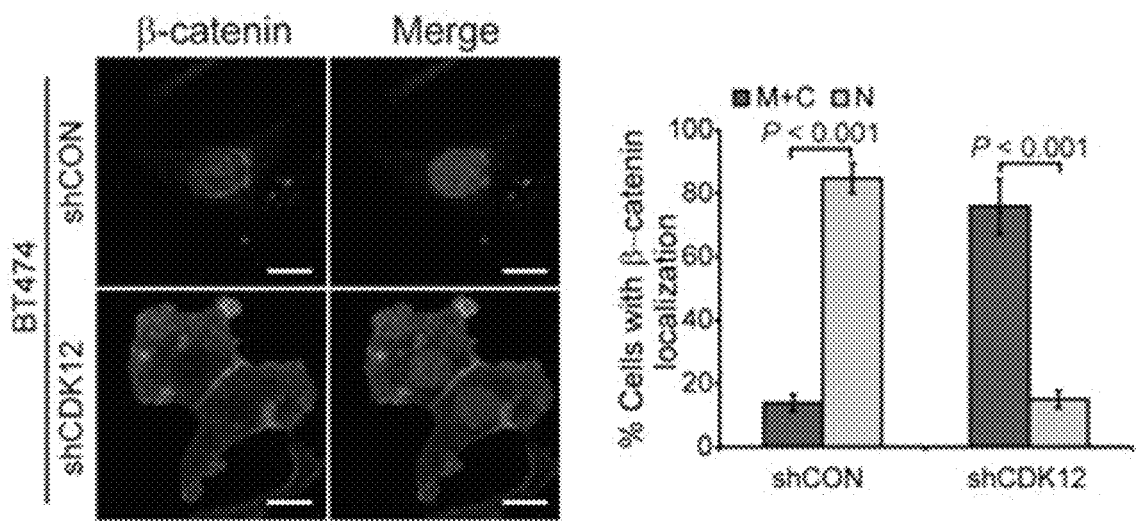
Figure 17A:
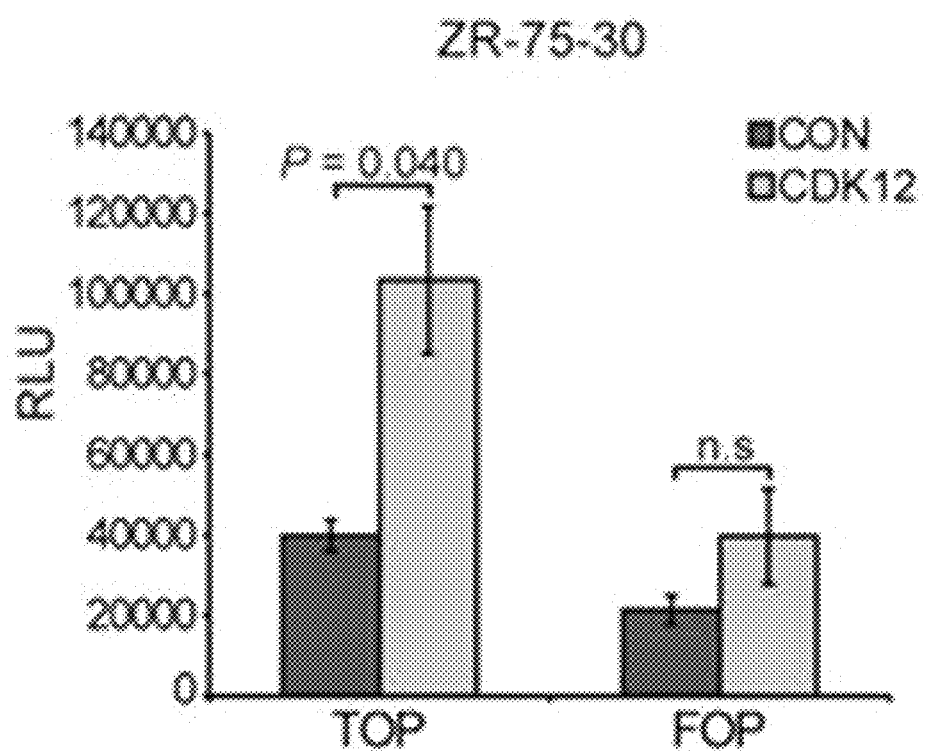
Figure 17B:
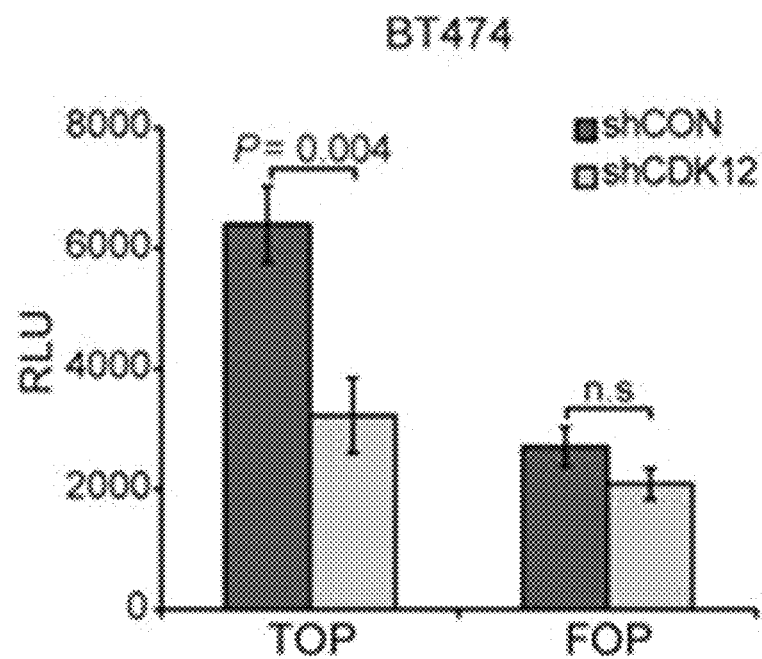
Figure 18:
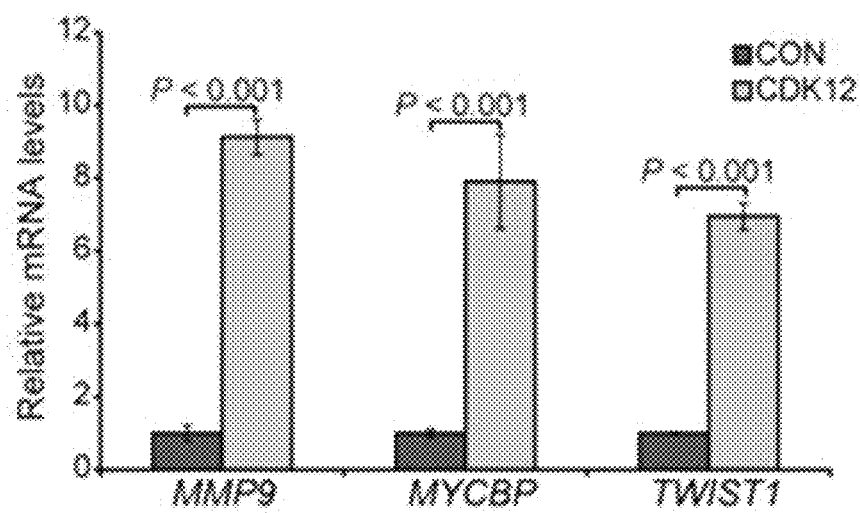

It was further examined whether or not an increase in CDK12-mediated expression of WNT1 and WNT3 had an influence on the activity of a canonical WNT signaling pathway in HER2+ breast cancer. CDK12 overexpression increased glycogen synthase kinase-3β (GSK-3β) phosphorylation and β-catenin expression in ZR-75-30 cells, whereas CDK12-knockdown reduced these GSK-33 and β-catenin activities in the BT474 cells (FIG. 14). Furthermore, a change in CDK12 expression caused a change in WNT1 and WNT3 expression (FIG. 14). Also, the immunoblot and immunofluorescence staining analyses showed that β-catenin was accumulated in the nuclei in response to CDK12 overexpression (FIGS. 15A, 15B, 16A and 16B). As a result, TCF/LEF-promoter activity and the expression of the β-catenin/TCF-target gene were positively regulated by CDK12 (FIGS. 17A, 17B and 18). In summary, the above-described results suggest that CDK12 activates a WNT/β-catenin signaling cascade through the expression of WNT ligands to improve the stemness of HER2+ breast cancer.

[Experimental Example 5] Activation of ErbB-PI3K-AKT Signaling Cascade Through Promotion of Interactions Among IRS1, ErbBs, and p 85 of CDK12

To more clearly demonstrate that CDK12 is involved in the regulation of the EGFR- and PI3K-signaling cascades based on gene-set enrichment analysis (GSEA) of the RNA-seq results, a receptor tyrosine kinase (RTK) array was performed using the CDK12-knockdown BT474 cells.

Figure 19:
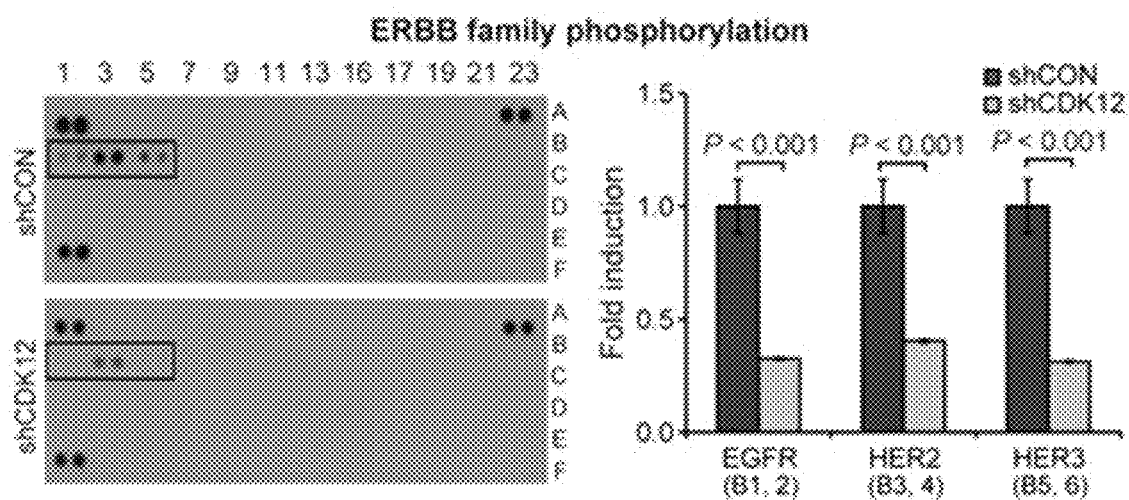
FIGS. 19, 20, 21, 22, 23 and 24 show that CDK12 upregulates IRS1 expression to activate an EGFR-HER2-PI3K-AKT signal.
Figure 20:
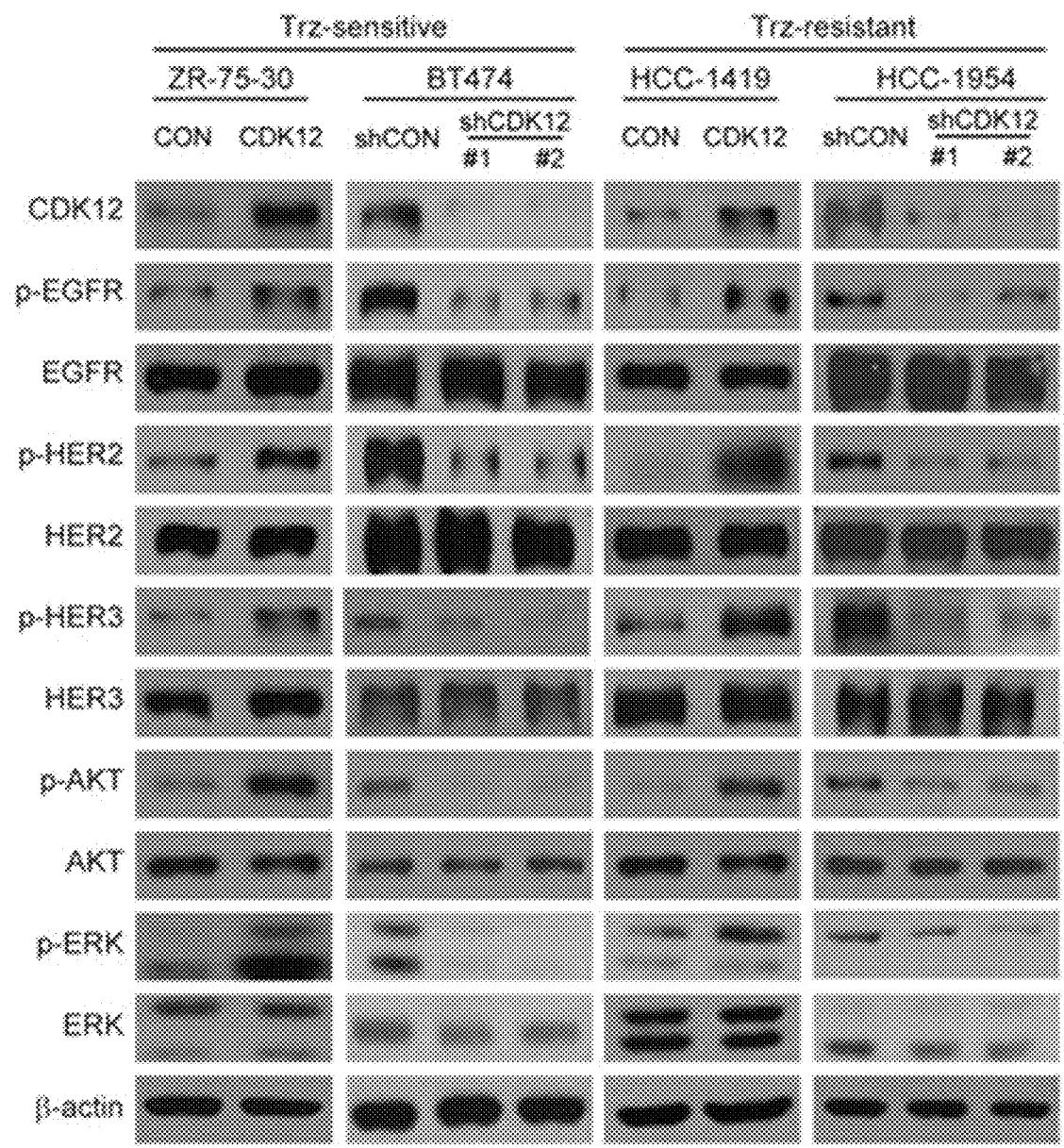

As a result, it was confirmed that the phosphorylation levels of ErbB family members (including EGFR, HER2, and HER3, but excluding HER4) were reduced by CDK12 knockdown in these cells (FIG. 19). Consistent with these results, the immunoblot analysis results showed that the phosphorylated forms of the ErbB family members and their downstream AKT and extracellular signal-regulated kinase (ERK) signal transduction were changed in response to CDK12 expression in the various HER2+ breast cancer cell lines having different response rates to trastuzumab (FIG. 20).

Figure 21:
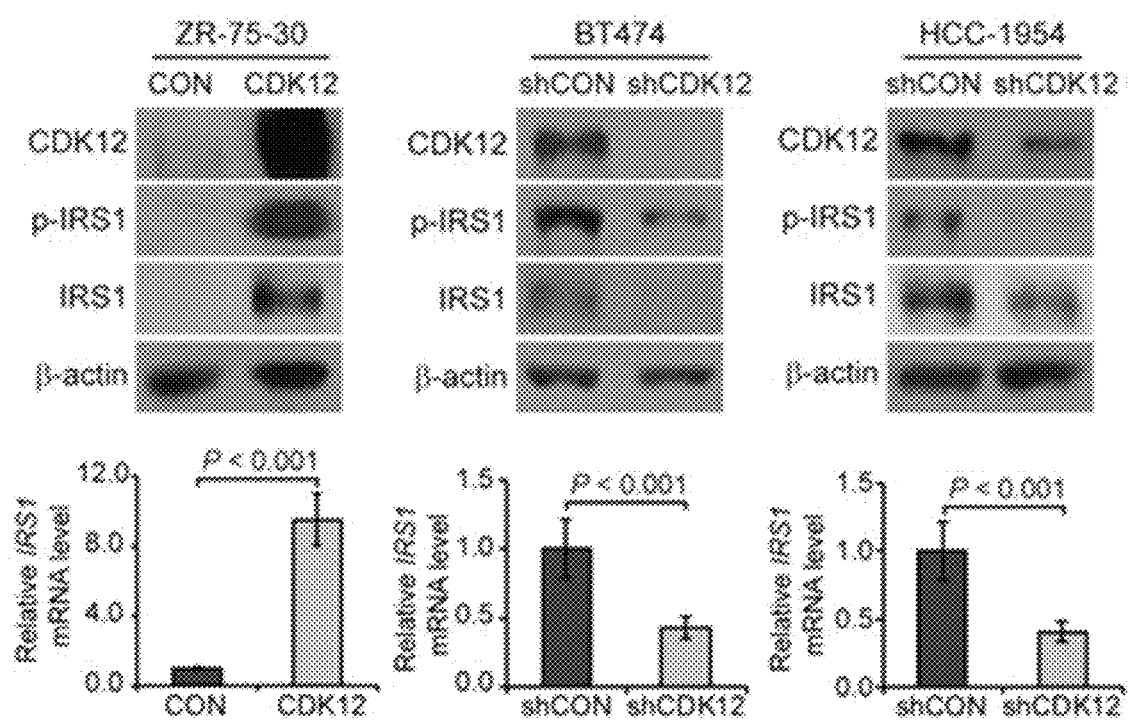
Figure 22:
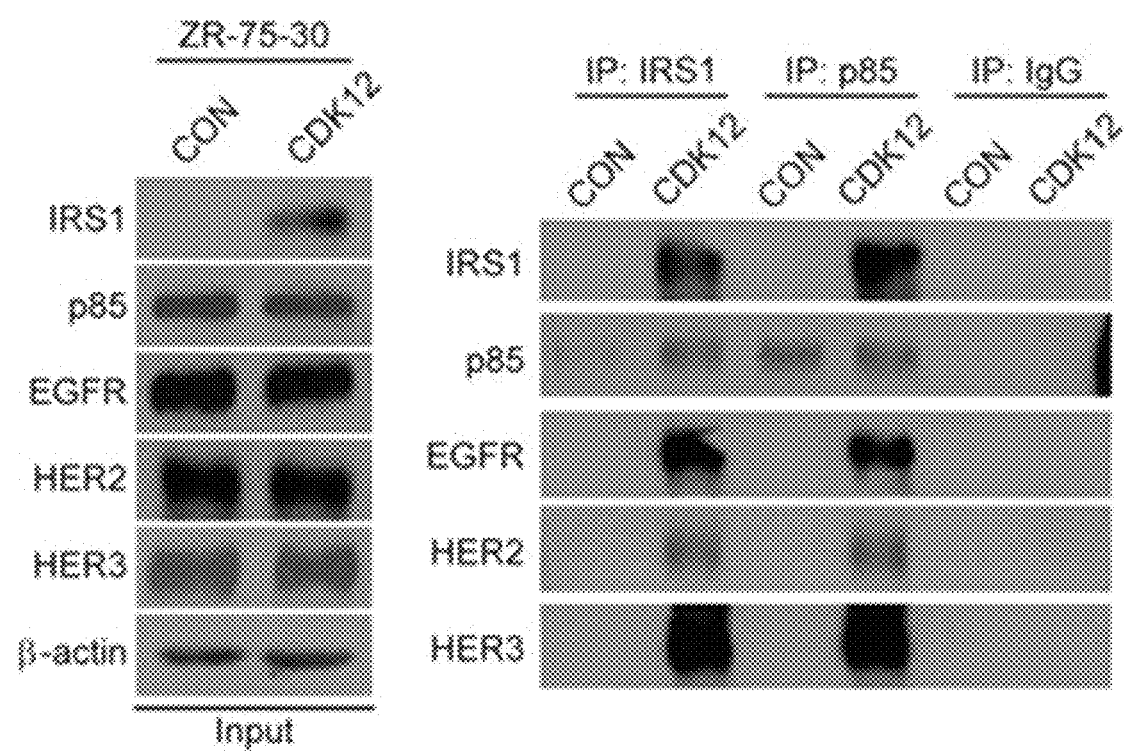
Figure 23:
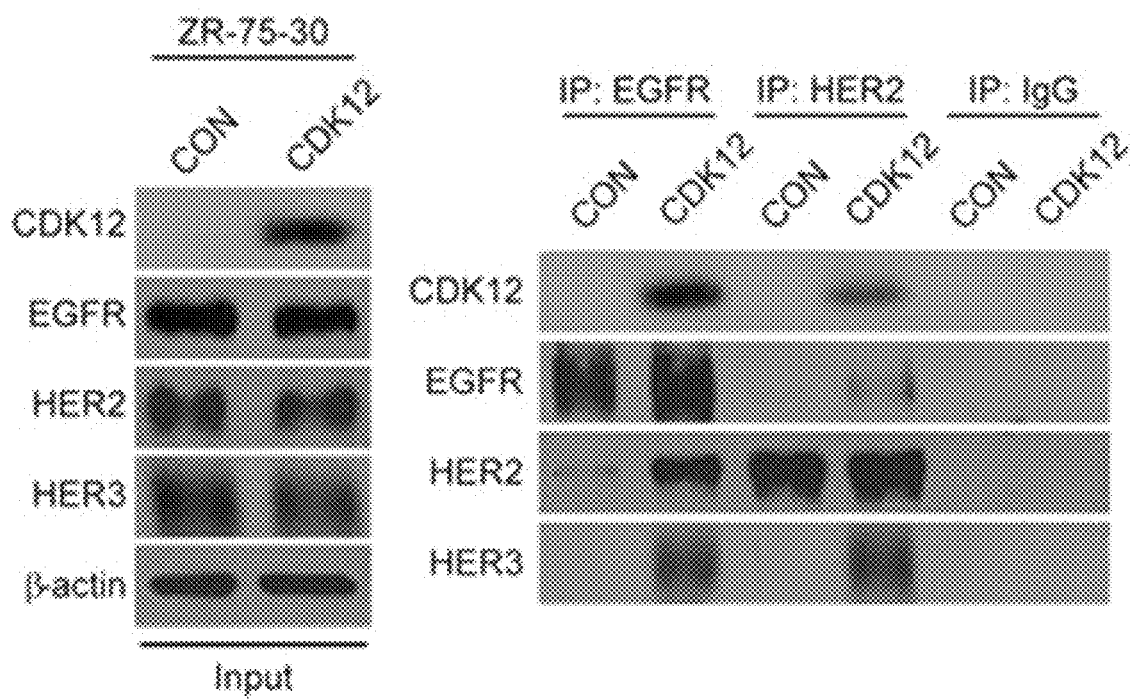

IRS1 proven as a CDK12-target gene by RNA-seq analysis directly interacts with various ErbB receptors and a regulatory subunit (p 85) of PI3K to regulate AKT phosphorylation[36-38]. Consistent with the RNA-seq results, immunoblot and qRT-PCR analyses showed that levels of IRS1 and a phosphorylated form [IRS1(Y612)] thereof were positively regulated by CDK12 in trastuzumab-sensitive and -resistant HER2+ breast cancer cells (FIG. 21). Co-immunoprecipitation analysis showed that increased IRS1 expression and activity enhanced the binding affinity between the IRS1 and the p 85 as well as between the IRS1 and the ErbB receptor (FIG. 22). Also, this relationship showed that heterodimerization was induced among EGFR, HER2 and HER3 (FIG. 23). Therefore, these results showed that CDK12 activated ErbB-PI3K- and ERK-signaling cascades by promoting IRS1-p 85-ErbB-receptor binding and enhancing the expression and activity of IRS1 in trastuzumab-sensitive and -resistant HER2+ breast cancers.

The CDK12 of the present invention is a prognostic/predictive factor of the response of a subject to an anti-HER2-targeted therapeutic agent in HER2+ cancer, and is thus suitable for companion diagnostics of the HER2-targeted therapeutic agent in the subject suffering from HER2+ cancer, and can overcome resistance to the HER2-targeted therapeutic agent and further improve a therapeutic effect of the HER2-targeted therapeutic agent through co-administration of a CDK12 inhibitor, thereby further enhancing efficiency of the HER2-targeted therapeutic agent by HER2 therapy.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method for treating a HER2 positive cancer of a subject in need thereof, the method comprising
   (a) providing a test sample from the subject suffering from a H E R2 positive cancer;
   (b) determining a CDK12 level in the test sample;
   (c) determining the presence of an increase in the CDK12 level in the test sample compared to a reference value,
   (d) administering a monotherapy consisting of CDK12 inhibitor alone to the subject with an increased CDK12 level compared to the reference value,
   wherein the subject exhibits drug resistance to a HER2 targeted therapeutic agent.

2. The method of claim 1, wherein the (b) determining CDK12 level is conducted using a method selected from the group consisting of fluorescence in situ hybridization (FISH), a comparative genomic hybridization (CGH)-based array, a single nucleotide polymorphism array (a SNP array), sequence assembly comparison, paired-end sequencing, a multiplex ligation dependent probe amplification (MLPA) method, a multiplex amplifiable probe hybridization (MAPH) method, quantitative multiplex PCR of short fluorescent fragments (QMPSF), a microsatellite genotyping method, Southern blotting, immunohistochemistry (IHC), a polymerase chain reaction (PCR), a quantitative polymerase chain reaction (qPCR), a quantitative real-time polymerase chain reaction (qRT-PCR), a real-time polymerase chain reaction (real-time PCR), microarray-based comparative genomic hybridization, and a ligase chain reaction (LCR).

3. The method of claim 1, wherein the CDK12 inhibitor comprises one or more selected from the group consisting of an antisense nucleotide, small interfering RNA (siRNA), short hairpin RNA (shRNA), a peptide, a peptide mimetic, an aptamer, and an antibody, which complementarily or specifically bind to CDK12, or comprises one or more selected from the group consisting of dinaciclib and THZ-531.

4. The method of claim 1, wherein the HER2 targeted therapeutic agent is selected from the group consisting of trastuzumab, pertuzumab, and trastuzumab emtansine (T-DM1).

5. The method of claim 1, wherein the step (b) determining CDK12 level comprises one or more of the following (i)-(iii):
   (i) determining a copy number of CDK12 genes in the test sample;
   (ii) determining an expression level of CDK12 proteins in the test sample; and
   (iii) determining an expression level of CDK12 mRNAs in the test sample.

6. The method of claim 3, wherein the HER2 targeted therapeutic agent is selected from the group consisting of trastuzumab, pertuzumab, and trastuzumab emtansine (T-DM1).

7. The method of claim 5, wherein the (i) determining a copy number of CDK12 genes is performed by fluorescent in situ hybridization (FISH) in the tissue or blood sample.

8. The method of claim 1, wherein the step (b) determining CDK12 level is performed with a sense primer, an antisense primer, an antibody, an aptamer, or a probe, which is complementary or specifically binds CDK12.

9. The method of claim 7, wherein the FISH is performed with a nucleic acid probe that is fluorescently labeled.

10. The method of claim 5, wherein the CDK12 genes comprise the sequence of SEQ ID NO: 3.

11. The method of claim 1, wherein the CDK12 inhibitor is a short hairpin RNA (shRNA) or dinaciclib, and wherein the HER2 targeted therapeutic agent is trastuzumab or trastuzumab emtansine (T-DM1).

* * * * *

SEQUENCE LISTING

<160> NUMBER OF SEQ ID NOS: 49

<210> SEQ ID NO 1
<211> LENGTH: 8283
<212> TYPE: DNA
<213> ORGANISM: Homo sapiens

<400> SEQUENCE: 1

```
gtgtgactgg gtctgtgtga gggagagagt gtgtgtggtg tggaggtgaa acggaggcaa      60 gaaaggggc tacctcagga gcgagggaca aagggggcgt gaggcaccta ggccgcggca     120
ccccggcgac aggaagccgt cctgaaccgg gctaccgggt aggggaaggg cccgcgtagt     180
cctcgcaggg ccccagagct ggagtcggct ccacagcccc gggccgtcgg cttctcactt     240
cctggacctc cccggcgccc gggcctgagg actggctcgg cggagggaga agaggaaaca     300
gacttgagca gctccccgtt gtctcgcaac tccactgccg aggaactctc atttcttccc     360
tcgctccttc acccccacc tcatgtagaa gggtgctgag gcgtcgggag ggaggaggag     420
cctgggctac cgtccctgcc ctccccaccc ccttcccggg gcgctttggt gggcgtggag     480
ttggggttgg gggggtgggt gggggttgct ttttggagtg ctggggaact ttttcccctt     540
cttcaggtca gggaaaggg aatgcccaat tcagagagac atgggggcaa gaaggacggg     600
agtggaggag cttctggaac tttgcagccg tcatcgggag gcggcagctc taacagcaga     660
gagcgtcacc gcttggtatc gaagcacaag cggcataagt ccaaacactc caaagacatg     720
gggttggtga cccccgaagc agcatccctg ggcacagtta tcaaacctttt ggtggagtat     780 gatgatatca gctctgattc cgacaccttc tccgatgaca tggccttcaa actagaccga     840
agggagaacg acgaacgtcg tggatcagat cggagcgacc gcctgcacaa acatcgtcac     900
caccagcaca ggcgttcccg ggacttacta aaagctaaac agaccgaaaa agaaaaaagc     960
caagaagtct ccagcaagtc gggatcgatg aaggaccgga tatcgggaag ttcaaagcgt    1020
tcgaatgagg agactgatga ctatgggaag gcgcaggtag ccaaaagcag cagcaaggaa    1080
tccaggtcat ccaagctcca caaggagaag accaggaaag aacgggagct gaagtctggg    1140
cacaaagacc ggagtaaaag tcatcgaaaa agggaaacac ccaaaagtta caaacagtg    1200 gacagcccaa aacggagatc caggagcccc cacaggaagt ggtctgacag ctccaaacaa    1260
gatgatagcc cctcgggagc ttcttatggc caagattatg accttagtcc ctcacgatct    1320
catacctcga gcaattatga ctcctacaag aaaagtcctg gaagtacctc gagaaggcag    1380
tcggtcagtc cccttacaa ggagccttcg gcctaccagt ccagcacccg gtcaccgagc    1440
ccctacagta ggcgacagag atctgtcagt ccctatagca ggagacggtc gtccagctac    1500
gaaagaagtg gctcttacag cgggcgatcg cccagtccct atggtcgaag gcggtccagc    1560 agcccttttcc tgagcaagcg gtctctgagt cggagtccac tccccagtag gaaatccatg    1620
```

```
aagtccagaa gtagaagtcc tgcatattca agacattcat cttctcatag taaaaagaag    1680
agatccagtt cacgcagtcg tcattccagt atctcacctg tcaggcttcc acttaattcc    1740
agtctgggag ctgaactcag taggaaaaag aaggaaagag cagctgctgc tgctgcagca    1800
aagatggatg gaaaggagtc caagggttca cctgtatttt tgcctagaaa agagaacagt    1860
tcagtagagg ctaaggattc aggtttggag tctaaaaagt tacccagaag tgtaaaattg    1920
gaaaaatctg ccccagatac tgaactggtg aatgtaacac atctaaacac agaggtaaaa    1980
aattcttcag atacagggaa agtaaagttg gatgagaact ccgagaagca tcttgttaaa    2040
gatttgaaag cacagggaac aagagactct aaacccatag cactgaaaga ggagattgtt    2100
actccaaagg agacagaaac atcagaaaag gagacccctc cacctcttcc cacaattgct    2160
tctcccccac cccctctacc aactactacc cctccacctc agacaccccc tttgccacct    2220
ttgcctccaa taccagctct tccacagcaa ccacctctgc ctccttctca gccagcattt    2280
agtcaggttc ctgcttccag tacttcaact ttgccccctt ctactcactc aaagacatct    2340
gctgtgtcct ctcaggcaaa ttctcagccc cctgtacagg tttctgtgaa gactcaagta    2400
tctgtaacag ctgctattcc acacctgaaa acttcaacgt tgcctccttt gcccctccca    2460
cccttattac ctggagatga tgacatggat agtccaaaag aaactcttcc ttcaaaacct    2520
gtgaagaaag agaaggaaca gaggacacgt cacttactca cagaccttcc tctccctcca    2580
gagctccctg gtggagatct gtctccccca gactctccag aaccaaaggc aatcacacca    2640
cctcagcaac catataaaaa gagaccaaaa atttgttgtc ctcgttatgg agaaagaaga    2700
caaacagaaa gcgactgggg gaaacgctgt gtggacaagt ttgacattat tgggattatt    2760
ggagaaggaa cctatggcca agtatataaa gccaaggaca aagacacagg agaactagtg    2820
gctctgaaga aggtgagact agacaatgag aaagagggct tcccaatcac agccattcgt    2880
gaaatcaaaa tccttcgtca gttaatccac cgaagtgttg ttaacatgaa ggaaattgtc    2940
acagataaac aagatgcact ggatttcaag aaggacaaag gtgccttttta ccttgtattt    3000 gagtatatgg accatgactt aatgggactg ctagaatctg gtttggtgca cttttctgag    3060
gaccatatca agtcgttcat gaaacagcta atggaaggat tggaatactg tcacaaaaag    3120
aatttcctgc atcgggatat taagtgttct aacattttgc tgaataacag tgggcaaatc    3180 aaaactagcag attttggact tgctcggctc tataactctg aagagagtcg cccttacaca    3240
aacaaagtca ttactttgtg gtaccgacct ccagaactac tgctaggaga ggaacgttac    3300
acaccagcca tagatgtttg gagctgtgga tgtattcttg gggaactatt cacaaagaag    3360
cctatttttc aagccaatct ggaactggct cagctagaac tgatcagccg actttgtggt    3420
agcccttgtc cagctgtgtg gcctgatgtt atcaaactgc cctacttcaa caccatgaaa    3480
ccgaagaagc aatatcgaag gcgtctacga aagaattct ctttcattcc ttctgcagca    3540
cttgatttat tggaccacat gctgacacta gatcctagta agcggtgcac agctgaacag    3600
accctacaga gcgacttcct taaagatgtc gaactcagca aaatggctcc tccagacctc    3660
ccccactggc aggattgcca tgagttgtgg agtaagaaac ggcgacgtca gcgacaaagt    3720
ggtgttgtag tcgaagagcc acctccatcc aaaacttctc gaaaagaaac tacctcaggg    3780
acaagtactg agcctgtgaa gaacagcagc ccagcaccac ctcagcctgc tcctggcaag    3840
gtggagtctg ggctgggga tgcaataggc cttgctgaca tcacacaaca gctgaatcaa    3900
agtgaattgg cagtgttatt aaacctgctg cagagccaaa ccgacctgag catccctcaa    3960
```

```
atggcacagc tgcttaacat ccactccaac ccagagatgc agcagcagct ggaagccctg    4020
aaccaatcca tcagtgccct gacggaagct acttcccagc agcaggactc agagaccatg    4080
gccccagagg agtctttgaa ggaagcaccc tctgcccag tgatcctgcc ttcagcagaa     4140
cagacgaccc ttgaagcttc aagcacacca gctgacatgc agaatatatt ggcagttctc    4200
ttgagtcagc tgatgaaaac ccaagagcca gcaggcagtc tggaggaaaa caacagtgac    4260
aagaacagtg ggccacaggg gccccgaaga actcccacaa tgccacagga ggaggcagca    4320
gcatgtcctc ctcacattct tccaccagag aagaggcccc ctgagccccc cggacctcca    4380
ccgccgccac ctccaccccc tctggttgaa ggcgatcttt ccagcgcccc ccaggagttg    4440
aacccagccg tgacagccgc cttgctgcaa ctttttatcc cagcctgaagc agagcctcct   4500 ggccacctgc cacatgagca ccaggccttg agaccaatgg agtactccac ccgaccccgt    4560
ccaaacagga cttatggaaa cactgatggg cctgaaacag ggttcagtgc cattgacact    4620
gatgaacgaa actctggtcc agccttgaca gaatccttgg tccagaccct ggtgaagaac    4680
aggaccttct caggctctct gagccacctt ggggagtcca gcagttacca gggcacaggg    4740
tcagtgcagt ttccagggga ccaggacctc cgttttgcca gggtccccct agcgttacac    4800
ccggtggtcg gcaaccatt cctgaaggct gagggaagca gcaattctgt ggtacatgca    4860
gagaccaaat tgcaaaacta gggagctg gggccaggaa ccactggggc cagcagctca     4920
ggagcaggcc ttcactgggg gggcccaact cagtcttctg cttatggaaa actctatcgg    4980
gggcctacaa gagtcccacc aagagggga gagggagag gagttcctta ctaacccaga     5040
gacttcagtg tcctgaaaga ttcctttcct atccatcctt ccatccagtt ctctgaatct    5100
ttaatgaaat catttgccag agcgaggtaa tcatctgcat ttggctactg caaagctgtc    5160
cgttgtattc cttgctcact tgctactagc aggcgactta cgaaataatg atgttggcac    5220
cagttccccc tggatgggct atagccagaa catttacttc aactctacct tagtagatac    5280
aagtagagaa tatggagagg atcattacat tgaaaagtaa atgttttatt agttcattgc    5340
ctgcacttac tgatcggaag agagaaagaa cagtttcagt attgagatgg ctcaggagag    5400
gctctttgat ttttaaagtt ttggggtggg ggattgtgtg tggtttcttt cttttgaatt    5460
ttaatttagg tgttttgggt ttttttcctt taaagagaat agtgttcaca aaatttgagc    5520
tgctctttgg cttttgctat aagggaaaca gagtggcctg gctgatttga ataaatgttt    5580
ctttcctctc caccatctca cattttgctt ttaagtgaac acttttttccc cattgagcat   5640 cttgaacata cttttttttcc aaataaatta ctcatcctta aagttactc cactttgaca   5700 aaagatacgc ccttctccct gcacataaag caggttgtag aacgtggcat tcttgggcaa   5760
gtaggtagac tttacccagt ctctttcctt ttttgctgat gtgtgctctc tctctctctt   5820
tctctctctc tctctctctc tctctctctc tctctctctc tgtctcgctt gctcgctctc   5880
gctgtttctc tctctttgag gcatttgttt ggaaaaaatc gttgagatgc ccaagaacct   5940
gggataattc tttactttttt ttgaaataaa ggaaaggaaa ttcagactct acattgttc   6000 tctgtaactc ttcaattcta aaatgttttg tttttttaaac catgttctga tggggaagtt   6060
gatttgtaag tgtggacagc ttggacattg ctgctgagct gtggttagag atgatgcctc    6120
cattcctaga gggctaataa cagcatttag catattgttt acacatatat ttttatgtca    6180
aaaaaaaaac aaaaaccttt caaacagagc attgtgatat tgtcaaagag aaaaacaaat    6240
cctgaagata catggaaatg taacctagtt tagggtgggt attttctga agatacatca     6300 atacctgacc ttttttaaaa aaataatttt aaaacagcat actgtgagga agaacagtat    6360
```

```
tgacatacccc acatcccagc atgtgtaccc tgccagttct tttagggatt tttcctccaa    6420
agagatttgg atttggtttt ggtaaaaggg gttaaattgt gcttccaggc aagaactttg    6480
ccttatcata aacaggaaat gaaaaaggga agggctgtca ggatgggata atttgggagg    6540
cttctcattc tggcttctat ttctatgtga gtaccagcat atagagtgtt ttaaaaacag    6600
atacatgtca tataatttat ctgcacagac ttagaccttc aggaaacata ggttaagccc    6660
ccttttacaa agaaaagta acatacttc agcatcttgg agggtagttt tcaaaactca    6720
agtttcatgt ttcaatgcca agttcttatt ttaaaaaata aaatctactt ataagagaaa    6780
ggtgcattac ttaaaaaaaa aaaactttaa agaaatgaaa aagaacccct cttcagatac    6840
ttacttgaag actgttttcc cctgttaatg agatatagct agatatcggt gtgtgtattt    6900
ctttattatt ctctggtttt tgatctggcc ttgcctccag ggccaaacac tgatttagaa    6960
agagagcctt ctagctattt tggcattgat ggcttttat accagtgtgt ccagttagat    7020
ttactaggct tactgacatg ctattggtaa atcgcattaa agttcatctg aaccttctgt    7080
ctgttgactt cttagtcctc agacatgggc ctttgtgttt tagaatattt gaattttgagt    7140 tattgggccc cactccctgt tttttattaa agaacgtgag cctgggatac ttcagaagt    7200 atctgttcaa tgaaaaaaag ttggtttccc atcaaatatg aataaaattc tctatatatt    7260
tcattgtatt ttggttatca gcagtcatca ataatgtttt tccctcccct ctcccacctc    7320
ttatttttaa ttatgccaaa tatcctaaat aatatactta agcctccatt ccctcatccc    7380
tactagggaa gggggtgagt gtatgtgtga gtgtatgtgt atgtatgatc ccatctcacc    7440 cccacccca ttttgggagt cttttaaaat gaaaacaaag tttggtagtt ttgactattt    7500
ctaaaagcag aggagaaaaa aaaacttatt taaatatcct ggaatctgta tggaggaaga    7560
aaaggtattt gttaattttt cagttacgtt atctataaac atgatggaag taaaggtttg    7620
gcagaatttc accttgacta tttgaaaatt acagacccaa ttaattccat tcaaaagtgg    7680
ttttcgtttt gttttaatta ttgtacaatg agagatattg tctattaaat acattatttt    7740
gaacagatga gaaatctgat tctgttcatg agtgggaggc aaaactggtt tgaccgtgat    7800 cattttgtg gttttgaaaa caaatatact tgacccagtt tccttagttt tttcttcaac    7860
tgtccatagg aacgataagt atttgaaagc aacatcaaat ctatacgttt aaagcagggc    7920
agttagcaca aatttgcaag tagaacttct attagcttat gccatagaca tcacccaacc    7980
acttgtatgt gtgtgtgtat atataatatg catatatagt taccgtgcta aaatggttac    8040
cagcaggttt tgagagagaa tgctgcatca gaaaagtgtc agttgccacc tcattctccc    8100
tgatttaggt tcctgacact gattcctttc tctctcgttt ttgaccccca ttgggtgtat    8160
cttgtctatg tacagatatt ttgtaatata ttaaattttt ttctttcagt ttataaaaat    8220
ggaaagtgga gattggaaaa ttaaatattt cctgttacta taccactttt gctccattgc    8280
att                                                                  8283

<210> SEQ ID NO 2
<211> LENGTH: 8256
<212> TYPE: DNA
<213> ORGANISM: Homo sapiens

<400> SEQUENCE: 2
gtgtgactgg gtctgtgtga gggagagagt gtgtgtggtg tggaggtgaa acggaggcaa      60 gaaaggggggc tacctcagga gcgagggaca aagggggcgt gaggcaccta ggccgcggca    120
```

```
ccccggcgac aggaagccgt cctgaaccgg gctaccgggt aggggaaggg cccgcgtagt    180
cctcgcaggg ccccagagct ggagtcggct ccacagcccc gggccgtcgg cttctcactt    240
cctggacctc cccggcgccc gggcctgagg actggctcgg cggagggaga agaggaaaca    300
gacttgagca gctccccgtt gtctcgcaac tccactgccg aggaactctc atttcttccc    360
tcgctccttc acccccacc  tcatgtagaa gggtgctgag gcgtcgggag ggaggaggag    420
cctgggctac cgtccctgcc ctccccaccc ccttcccggg gcgctttggt gggcgtggag    480
ttggggttgg gggggtgggt ggggttgct  ttttggagtg ctggggaact ttttccctt     540
cttcaggtca ggggaaaggg aatgcccaat tcagagagac atgggggcaa gaaggacggg    600
agtggaggag cttctggaac tttgcagccg tcatcgggag gcggcagctc taacagcaga    660
gagcgtcacc gcttggtatc gaagcacaag cggcataagt ccaaacactc caaagacatg    720
gggttggtga cccccgaagc agcatccctg ggcacagtta tcaaaccttt ggtggagtat    780
gatgatatca gctctgattc cgacaccttc tccgatgaca tggccttcaa actagaccga    840
agggagaacg acgaacgtcg tggatcagat cggagcgacc gcctgcacaa acatcgtcac    900
caccagcaca ggcgttcccg ggacttacta aaagctaaac agaccgaaaa agaaaaaagc    960
caagaagtct ccagcaagtc gggatcgatg aaggaccgga tatcgggaag ttcaaagcgt   1020
tcgaatgagg agactgatga ctatgggaag gcgcaggtag ccaaaagcag cagcaaggaa   1080
tccaggtcat ccaagctcca caaggagaag accaggaaaa aacggagct  gaagtctggg   1140
cacaaagacc ggagtaaaag tcatcgaaaa agggaaacac ccaaaagtta caaaacagtg   1200
gacagcccaa aacggagatc caggagcccc cacaggaagt ggtctgacag ctccaaacaa   1260
gatgatagcc cctcgggagc ttcttatggc caagattatg accttagtcc ctcacgatct   1320
catacctcga gcaattatga ctcctacaag aaaagtcctg gaagtacctc gagaaggcag   1380
tcggtcagtc ccccttacaa ggagccttcg gcctaccagt ccagcacccg gtcaccgagc   1440
ccctacagta ggcgacagag atctgtcagt ccctatagca ggagacggtc gtccagctac   1500
gaaagaagtg gctcttacag cgggcgatcg cccagtccct atggtcgaag gcggtccagc   1560
agcccttttcc tgagcaagcg gtctctgagt cggagtccac tccccagtag gaaatccatg   1620
aagtccagaa gtagaagtcc tgcatattca agacattcat cttctcatag taaaaagaag   1680
agatccagtt cacgcagtcg tcattccagt atctcacctg tcaggcttcc acttaattcc   1740
agtctgggag ctgaactcag taggaaaaag aaggaaagag cagctgctgc tgctgcagca   1800
aagatggatg gaaaggagtc caagggttca cctgtatttt tgcctagaaa agagaacagt   1860
tcagtagagg ctaaggattc aggtttggag tctaaaaagt tacccagaag tgtaaaattg   1920
gaaaaatctg ccccagatac tgaactggtg aatgtaacac atctaaacac agaggtaaaa   1980
aattcttcag atacagggaa agtaaagttg gatgagaact ccgagaagca tcttgttaaa   2040
gatttgaaag cacagggaac aagagactct aaacccatag cactgaaaga ggagattgtt   2100
actccaaagg agacagaaac atcagaaaag gagacccctc cacctcttcc cacaattgct   2160
tctccccccac cccctctacc aactactacc cctccacctc agacacccc  tttgccacct   2220
ttgcctccaa taccagctct tccacagcaa ccacctctgc ctccttctca gccagcattt   2280
agtcaggttc ctgcttccag tacttcaact ttgccccctt ctactcactc aaagacatct   2340
gctgtgtcct ctcaggcaaa ttctcagccc cctgtacagg tttctgtgaa gactcaagta   2400
tctgtaacag ctgctattcc acacctgaaa acttcaacgt tgcctccttt gcccctccca   2460
cccttattac ctggagatga tgacatggat agtccaaaag aaactcttcc ttcaaaacct   2520
```

```
gtgaagaaag agaaggaaca gaggacacgt cacttactca cagaccttcc tctccctcca    2580
gagctccctg gtggagatct gtctccccca gactctccag aaccaaaggc aatcacacca    2640
cctcagcaac catataaaaa gagaccaaaa atttgttgtc ctcgttatgg agaaagaaga    2700
caaacagaaa gcgactgggg gaaacgctgt gtggacaagt tgacattat tgggattatt     2760 ggagaaggaa cctatggcca agtatataaa gccaaggaca agacacagg agaactagtg     2820 gctctgaaga aggtgagact agacaatgag aaagagggct tcccaatcac agccattcgt    2880
gaaatcaaaa tccttcgtca gttaatccac cgaagtgttg ttaacatgaa ggaaattgtc    2940
acagataaac aagatgcact ggatttcaag aaggacaaag gtgccttta ccttgtattt     3000 gagtatatgg accatgactt aatgggactg ctagaatctg gtttggtgca cttttctgag    3060
gaccatatca agtcgttcat gaaacagcta atggaaggat tggaatactg tcacaaaaag    3120
aatttcctgc atcgggatat taagtgttct aacattttgc tgaataacag tgggcaaatc    3180
aaactagcag attttggact tgctcggctc tataactctg aagagagtcg cccttacaca    3240
aacaaagtca ttactttgtg gtaccgacct ccagaactac tgctaggaga ggaacgttac    3300
acaccagcca tagatgtttg gagctgtgga tgtattcttg gggaactatt cacaaagaag    3360
cctatttttc aagccaatct ggaactggct cagctagaac tgatcagccg actttgtggt    3420
agcccttgtc cagctgtgtg gcctgatgtt atcaaactgc cctacttcaa caccatgaaa    3480
ccgaagaagc aatatcgaag gcgtctacga gaagaattct ctttcattcc ttctgcagca    3540
cttgatttat tggaccacat gctgacacta gatcctagta gcggtgcac agctgaacag     3600 accctacaga gcgacttcct taaagatgtc gaactcagca aaatggctcc tccagacctc    3660
ccccactggc aggattgcca tgagttgtgg agtaagaaac ggcgacgtca gcgacaaagt    3720
ggtgttgtag tcgaagagcc acctccatcc aaaacttctc gaaaagaaac tacctcaggg    3780
acaagtactg agcctgtgaa gaacagcagc ccagcaccac ctcagcctgc tcctggcaag    3840
gtggagtctg gggctgggga tgcaataggc cttgctgaca tcacacaaca gctgaatcaa    3900
agtgaattgg cagtgttatt aaacctgctg cagagccaaa ccgacctgag catccctcaa    3960
atggcacagc tgcttaacat ccactccaac ccagagatgc agcagcagct ggaagccctg    4020
aaccaatcca tcagtgccct gacggaagct acttcccagc agcaggactc agagaccatg    4080
gccccagagg agtctttgaa ggaagcaccc tctgccccag tgatcctgcc ttcagcagaa    4140
cagacgaccc ttgaagcttc aagcacacca gctgacatgc agaatatatt ggcagttctc    4200
ttgagtcagc tgatgaaaac ccaagagcca gcaggcagtc tggaggaaaa caacagtgac    4260
aagaacagtg ggccacaggg gccccgaaga actcccacaa tgccacagga ggaggcagca    4320
gagaagaggc cccctgagcc ccccggacct ccaccgccgc cacctccacc ccctctggtt    4380
gaaggcgatc tttccagcgc ccccaggag ttgaacccag ccgtgacagc cgccttgctg     4440 caactttat cccagcctga agcagagcct cctggccacc tgccacatga gcaccaggcc     4500
ttgagaccaa tggagtactc caccccgaccc cgtccaaaca ggacttatgg aaacactgat    4560
gggcctgaaa cagggttcag tgccattgac actgatgaac gaaactctgg tccagccttg    4620
acagaatcct tggtccagac cctggtgaag aacaggacct tctcaggctc tctgagccac    4680
cttggggagt ccagcagtta ccagggcaca gggtcagtgc agtttccagg ggaccaggac    4740
ctccgttttg ccagggtccc cttagcgtta cacccggtgg tcgggcaacc attcctgaag    4800
gctgagggaa gcagcaattc tgtggtacat gcagagacca aattgcaaaa ctatgggag     4860
```

-continued

```
ctggggccag gaaccactgg ggccagcagc tcaggagcag gccttcactg ggggggccca    4920
actcagtctt ctgcttatgg aaaactctat cggggggcta caagagtccc accaagaggg    4980
ggaagaggga gaggagttcc ttactaaccc agagacttca gtgtcctgaa agattccttt    5040
cctatccatc cttccatcca gttctctgaa tctttaatga aatcatttgc cagagcgagg    5100
taatcatctg catttggcta ctgcaaagct gtccgttgta ttccttgctc acttgctact    5160
agcaggcgac ttacgaaata atgatgttgg caccagttcc ccctggatgg gctatagcca    5220
gaacatttac ttcaactcta ccttagtaga tacaagtaga gaatatggag aggatcatta    5280
cattgaaaag taaatgtttt attagttcat tgcctgcact tactgatcgg aagagagaaa    5340
gaacagtttc agtattgaga tggctcagga gaggctcttt gattttaaaa gttttggggt    5400
gggggattgt gtgtggtttc tttcttttga attttaattt aggtgttttg ggttttttc     5460 cttaaagag aatagtgttc acaaaatttg agctgctctt tggcttttgc tataagggaa     5520
acagagtggc ctggctgatt tgaataaatg tttctttcct ctccaccatc tcacattttg    5580
cttttaagtg aacactttt ccccattgag catcttgaac atacttttt tccaaataaa      5640 ttactcatcc ttaaagttta ctccactttg acaaaagata cgcccttctc cctgcacata    5700
aagcaggttg tagaacgtgg cattcttggg caagtaggta gactttaccc agtctctttc    5760
cttttttgct gatgtgtgct ctctctctct ctttctctct ctctctctct ctctctctct    5820
ctctctctct ctctgtctcg cttgctcgct ctcgctgttt ctctctcttt gaggcatttg    5880
tttggaaaaa atcgttgaga tgcccaagaa cctgggataa ttctttactt tttttgaaat    5940
aaaggaaagg aaattcagac tcttacattg ttctctgtaa ctcttcaatt ctaaaatgtt    6000
ttgtttttta aaccatgttc tgatggggaa gttgatttgt aagtgtggac agcttggaca    6060
ttgctgctga gctgtggtta gagatgatgc ctccattcct agagggctaa taacagcatt    6120
tagcatattg tttacacata tattttatg tcaaaaaaaa aacaaaaacc tttcaaacag     6180
agcattgtga tattgtcaaa gagaaaaaca atcctgaag atacatggaa atgtaaccta     6240
gtttagggtg ggtattttc tgaagataca tcaatacctg acctttttta aaaaaataat    6300
tttaaaacag catactgtga ggaagaacag tattgacata cccacatccc agcatgtgta    6360
ccctgccagt tcttttaggg attttttcctc caaagagatt tggatttggt tttggtaaaa    6420
ggggttaaat tgtgcttcca ggcaagaact ttgccttatc ataaacagga aatgaaaaag    6480
ggaagggctg tcaggatggg ataatttggg aggcttctca ttctggcttc tatttctatg    6540
tgagtaccag catatagagt gttttaaaaa cagatacatg tcatataatt tatctgcaca    6600
gacttagacc ttcaggaaac ataggttaag cccccttta caaagaaaaa gtaaacatac     6660
ttcagcatct tggagggtag ttttcaaaac tcaagtttca tgtttcaatg ccaagttctt    6720
attttaaaaa ataaaatcta cttataagag aaaggtgcat tacttaaaaa aaaaaaactt    6780
taaagaaatg aaagaagaac cctcttcaga tacttacttg aagactgttt tcccctgtta    6840
atgagatata gctagatatc ggtgtgtgta tttctttatt attctctggt ttttgatctg    6900
gccttgcctc cagggccaaa cactgattta gaaagagagc cttctagcta ttttggcatt    6960
gatggctttt tataccagtg tgtccagtta gatttactag gcttactgac atgctattgg    7020
taaatcgcat taaagttcat ctgaaccttc tgtctgttga cttcttagtc ctcagacatg    7080
ggcctttgtg ttttagaata tttgaatttg agttattggg ccccactccc tgtttttttat    7140 taaagaacgt gagcctggga tactttcaga agtatctgtt caatgaaaaa aagttggttt    7200
cccatcaaat atgaataaaa ttctctatat atttcattgt attttggtta tcagcagtca    7260
```

```
tcaataatgt ttttccctcc cctctcccac ctcttatttt taattatgcc aaatatccta    7320
aataatatac ttaagcctcc attccctcat ccctactagg aagggggtg agtgtatgtg      7380 tgagtgtatg tgtatgtatg atcccatctc accccaccc ccatttgg agtcttttaa       7440 aatgaaaaca aagtttggta gttttgacta tttctaaaag cagaggagaa aaaaaaactt    7500
atttaaatat cctggaatct gtatggagga agaaaaggta tttgttaatt tttcagttac    7560
gttatctata aacatgatgg aagtaaaggt ttggcagaat ttcaccttga ctatttgaaa    7620
attacagacc caattaattc cattcaaaag tggttttcgt tttgttttaa ttattgtaca    7680
atgagagata ttgtctatta aatacattat tttgaacaga tgagaaatct gattctgttc    7740
atgagtggga ggcaaaactg gtttgaccgt gatcattttt gtggttttga aaacaaatat    7800
acttgaccca gttccttag ttttttcttc aactgtccat aggaacgata agtatttgaa      7860
agcaacatca aatctatacg tttaaagcag ggcagttagc acaaatttgc aagtagaact    7920
tctattagct tatgccatag acatcaccca accacttgta tgtgtgtgtg tatatataat    7980
atgcatatat agttaccgtg ctaaaatggt taccagcagg ttttgagaga gaatgctgca    8040
tcagaaaagt gtcagttgcc acctcattct ccctgattta ggttcctgac actgattcct    8100
ttctctctcg tttttgaccc ccattgggtg tatcttgtct atgtacagat attttgtaat    8160
atattaaatt tttttctttc agtttataaa aatggaaagt ggagattgga aaattaaata    8220
tttcctgtta ctataccact tttgctccat tgcatt                             8256

<210> SEQ ID NO 3
<211> LENGTH: 4473
<212> TYPE: DNA
<213> ORGANISM: Homo sapiens

<400> SEQUENCE: 3
atgcccaatt cagagagaca tgggggcaag aaggacggga gtggaggagc ttctggaact      60
ttgcagccgt catcgggagg cggcagctct aacagcagag agcgtcaccg cttggtatcg    120
aagcacaagc ggcataagtc caaacactcc aaagacatgg ggttggtgac ccccgaagca    180
gcatccctgg gcacagttat caaacctttg gtggagtatg atgatatcag ctctgattcc    240
gacaccttct ccgatgacat ggccttcaaa ctagaccgaa gggagaacga cgaacgtcgt    300
ggatcagatc ggagcgaccg cctgcacaaa catcgtcacc accagcacag gcgttcccgg    360
gacttactaa aagctaaaca gaccgaaaaa gaaaaaagcc aagaagtctc cagcaagtcg    420
ggatcgatga aggaccggat atcgggaagt tcaaagcgtt cgaatgagga gactgatgac    480
tatgggaagg cgcaggtagc caaaagcagc agcaaggaat ccaggtcatc caagctccac    540
aaggagaaga ccaggaaaga acgggagctg aagtctgggc acaaagaccg gagtaaaagt    600
catcgaaaaa gggaaacacc caaaagttac aaaacagtgg acagcccaaa acggagatcc    660
aggagccccc acaggaagtg gtctgacagc tccaaacaag atgatagccc ctcgggagct    720
tcttatggcc aagattatga ccttagtccc tcacgatctc atacctcgag caattatgac    780
tcctacaaga aaagtcctgg aagtacctcg agaggcagt cggtcagtcc cccttacaag     840
gagccttcgg cctaccagtc cagcacccgg tcaccgagcc cctacagtag cgacagagaa    900
tctgtcagtc cctatagcag gagacggtcg tccagctacg aaagaagtgg ctcttacagc    960
gggcgatcgc ccagtcccta tgtcgaagg cggtccagca gcccttttcct gagcaagcgg    1020 tctctgagtc ggagtccact ccccagtagg aaatccatga agtccagaag tagaagtcct    1080
```

```
gcatattcaa gacattcatc ttctcatagt aaaaagaaga gatccagttc acgcagtcgt    1140
cattccagta tctcacctgt caggcttcca cttaattcca gtctgggagc tgaactcagt    1200
aggaaaaaga aggaaagagc agctgctgct gctgcagcaa agatggatgg aaaggagtcc    1260
aagggttcac ctgtattttt gcctagaaaa gagaacagtt cagtagaggc taaggattca    1320
ggtttggagt ctaaaaagtt acccagaagt gtaaaattgg aaaaatctgc cccagatact    1380
gaactggtga atgtaacaca tctaaacaca gaggtaaaaa attcttcaga tacagggaaa    1440
gtaaagttgg atgagaactc cgagaagcat cttgttaaag atttgaaagc acagggaaca    1500
agagactcta aacccatagc actgaaagag gagattgtta ctccaaagga cacagaaaca    1560
tcagaaaagg agacccctcc acctcttccc acaattgctt ctcccccacc ccctctacca    1620
actactaccc ctccacctca gacacccccct tgccacctt tgcctccaat accagctctt    1680
ccacagcaac cacctctgcc tccttctcag ccagcattta gtcaggttcc tgcttccagt    1740
acttcaactt tgccccttc tactcactca aagacatctg ctgtgtcctc tcaggcaaat    1800
tctcagcccc ctgtacaggt ttctgtgaag actcaagtat ctgtaacagc tgctattcca    1860
cacctgaaaa cttcaacgtt gcctccttg ccctcccac ccttattacc tggagatgat    1920
gacatggata gtccaaaaga aactcttcct tcaaaacctg tgaagaaaga gaaggaacag    1980
aggacacgtc acttactcac agaccttcct ctccctccag agctcccctgg tggagatctg    2040 tctcccccag actctccaga accaaaggca atcacaccac ctcagcaacc atataaaaag    2100
agaccaaaaa tttgttgtcc tcgttatgga gaaagaagac aaacagaaag cgactggggg    2160
aaacgctgtg tggacaagtt tgacattatt gggattattg gagaaggaac ctatggccaa    2220
gtatataaag ccaaggacaa agacacagga gaactagtgg ctctgaagaa ggtgagacta    2280
gacaatgaga aagagggctt cccaatcaca gccattcgtg aaatcaaaat ccttcgtcag    2340
ttaatccacc gaagtgttgt taacatgaag gaaattgtca cagataaaca agatgcactg    2400
gatttcaaga aggacaaagg tgccttttac cttgtatttg agtatatgga ccatgactta    2460
atgggactgc tagaatctgg tttggtgcac ttttctgagg accatatcaa gtcgttcatg    2520
aaacagctaa tggaaggatt ggaatactgt cacaaaaaga atttcctgca tcgggatatt    2580
aagtgttcta acattttgct gaataacagt gggcaaatca aactagcaga ttttggactt    2640
gctcggctct ataactctga agagagtcgc ccttacacaa acaaagtcat tactttgtgg    2700
taccgacctc cagaactact gctaggagag gaacgttaca caccagccat agatgtttgg    2760
agctgtggat gtattcttgg ggaactattc acaaagaagc ctattttca gccaatctg    2820 gaactggctc agctagaact gatcagccga ctttgtggta gcccttgtcc agctgtgtgg    2880
cctgatgtta tcaaactgcc ctacttcaac accatgaaac cgaagaagca atatcgaagg    2940
cgtctacgag aagaattctc tttcattcct tctgcagcac ttgatttatt ggaccacatg    3000
ctgacactag atcctagtaa gcggtgcaca gctgaacaga ccctacagag cgacttcctt    3060
aaagatgtcg aactcagcaa aatggctcct ccagacctcc ccactggca ggattgccat    3120 gagttgtgga gtaagaaacg gcgacgtcag cgacaaagtg gtgttgtagt cgaagagcca    3180
cctccatcca aaacttctcg aaaagaaact acctcaggga caagtactga gcctgtgaag    3240
aacagcagcc cagcaccacc tcagcctgct cctggcaagg tggagtctgg ggctggggat    3300
gcaataggcc ttgctgacat cacacaacag ctgaatcaaa gtgaattggc agtgttatta    3360
aacctgctgc agagccaaac cgacctgagc atccctcaaa tggcacagct gcttaacatc    3420
cactccaacc cagagatgca gcagcagctg gaagccctga accaatccat cagtgccctg    3480
```

| | | | |
|---|---|---|---|
| acggaagcta | cttcccagca | gcaggactca | gagaccatgg ccccagagga gtctttgaag | 3540 |
| gaagcaccct | ctgccccagt | gatcctgcct | tcagcagaac agacgaccct tgaagcttca | 3600 |
| agcacaccag | ctgacatgca | gaatatattg | gcagttctct tgagtcagct gatgaaaacc | 3660 |
| caagagccag | caggcagtct | ggaggaaaac | aacagtgaca agaacagtgg gccacagggg | 3720 |
| ccccgaagaa | ctcccacaat | gccacaggag | gaggcagcag catgtcctcc tcacattctt | 3780 |
| ccaccagaga | gaggcccccc | tgagcccccc | ggacctccac cgccgccacc tccacccccct | 3840 |
| ctggttgaag | gcgatctttc | cagcgccccc | caggagttga acccagccgt gacagccgcc | 3900 |
| ttgctgcaac | ttttatccca | gcctgaagca | gagcctcctg gccacctgcc acatgagcac | 3960 |
| caggccttga | gaccaatgga | gtactccacc | cgaccccgtc caaacaggac ttatggaaac | 4020 |
| actgatgggc | ctgaaacagg | gttcagtgcc | attgacactg atgaacgaaa ctctggtcca | 4080 |
| gccttgacag | aatccttggt | ccagaccctg | gtgaagaaca ggaccttctc aggctctctg | 4140 |
| agccaccttg | gggagtccag | cagttaccag | ggcacagggt cagtgcagtt tccaggggac | 4200 |
| caggacctcc | gttttgccag | ggtccccttta | gcgttacacc cggtggtcgg gcaaccattc | 4260 |
| ctgaaggctg | agggaagcag | caattctgtg | gtacatgcag agaccaaatt gcaaaactat | 4320 |
| ggggagctgg | ggccaggaac | cactggggcc | agcagctcag gagcaggcct tcactggggg | 4380 |
| ggcccaactc | agtcttctgc | ttatggaaaa | ctctatcggg gcctacaag agtcccacca | 4440 |
| agaggggggaa | gagggagagg | agttccttac taa | | 4473 |

<210> SEQ ID NO 4
<211> LENGTH: 4446
<212> TYPE: DNA
<213> ORGANISM: Homo sapiens

<400> SEQUENCE: 4

| | | | |
|---|---|---|---|
| atgcccaatt | cagagagaca | tgggggcaag | aaggacggga gtggaggagc ttctggaact | 60 |
| ttgcagccgt | catcgggagg | cggcagctct | aacagcagag agcgtcaccg cttggtatcg | 120 |
| aagcacaagc | ggcataagtc | caaacactcc | aaagacatgg ggttggtgac ccccgaagca | 180 |
| gcatccctgg | gcacagttat | caaacctttg | gtggagtatg atgatatcag ctctgattcc | 240 |
| gacaccttct | ccgatgacat | ggccttcaaa | ctagaccgaa gggagaacga cgaacgtcgt | 300 |
| ggatcagatc | ggagcgaccg | cctgcacaaa | catcgtcacc accagcacag gcgttcccgg | 360 |
| gacttactaa | aagctaaaca | gaccgaaaaa | gaaaaaagcc aagaagtctc cagcaagtcg | 420 |
| ggatcgatga | aggaccggat | atcgggaagt | tcaaagcgtt cgaatgagga gactgatgac | 480 |
| tatgggaagg | cgcaggtagc | caaaagcagc | agcaaggaat ccaggtcatc caagctccac | 540 |
| aaggagaaga | ccaggaaaga | acgggagctg | aagtctgggc acaaagaccg gagtaaaagt | 600 |
| catcgaaaaa | gggaaacacc | caaaagttac | aaaacagtgg acagcccaaa acggagatcc | 660 |
| aggagccccc | acaggaagtg | gtctgacagc | tccaaacaag atgatagccc ctcgggagct | 720 |
| tcttatggcc | aagattatga | ccttagtccc | tcacgatctc atacctcgag caattatgac | 780 |
| tcctacaaga | aaagtcctgg | aagtacctcg | agaaggcagt cggtcagtcc cccttacaag | 840 |
| gagccttcgg | cctaccagtc | cagcacccgg | tcaccgagcc cctacagtag cgacagagaa | 900 |
| tctgtcagtc | cctatagcag | gagacggtcg | tccagctacg aaagaagtgg ctcttacagc | 960 |
| gggcgatcgc | ccagtcccta | tggtcgaagg | cggtccagca gccctttcct gagcaagcgg | 1020 |
| tctctgagtc | ggagtccact | ccccagtagg | aaatccatga agtccagaag tagaagtcct | 1080 |

```
gcatattcaa gacattcatc ttctcatagt aaaaagaaga gatccagttc acgcagtcgt    1140
cattccagta tctcacctgt caggcttcca cttaattcca gtctgggagc tgaactcagt    1200
aggaaaaaga aggaaagagc agctgctgct gctgcagcaa agatggatgg aaaggagtcc    1260
aagggttcac ctgtattttt gcctagaaaa gagaacagtt cagtagaggc taaggattca    1320
ggtttggagt ctaaaaagtt acccagaagt gtaaaattgg aaaaatctgc cccagatact    1380
gaactggtga atgtaacaca tctaaacaca gaggtaaaaa attcttcaga tacagggaaa    1440
gtaaagttgg atgagaactc cgagaagcat cttgttaaag atttgaaagc acagggaaca    1500
agagactcta aacccatagc actgaaagag gagattgtta ctccaaagga gacagaaaca    1560
tcagaaaagg agacccctcc acctcttccc acaattgctt ctcccccacc ccctctacca    1620
actactaccc ctccacctca gacacccccct ttgccaccctt tgcctccaat accagctctt    1680
ccacagcaac cacctctgcc tccttctcag ccagcattta gtcaggttcc tgcttccagt    1740
acttcaactt tgcccccttc tactcactca aagacatctg ctgtgtcctc tcaggcaaat    1800
tctcagcccc ctgtacaggt ttctgtgaag actcaagtat ctgtaacagc tgctattcca    1860
cacctgaaaa cttcaacgtt gcctcctttg cccctcccac ccttattacc tggagatgat    1920
gacatggata gtccaaaaga aactcttcct tcaaaacctg tgaagaaaga gaaggaacag    1980
aggacacgtc acttactcac agaccttcct ctccctccag agctccctgg tggagatctg    2040
tctcccccag actctccaga accaaaggca atcacaccac tcagcaacc atataaaaag    2100 agaccaaaaa tttgttgtcc tcgttatgga gaaagaagac aaacagaaag cgactggggg    2160
aaacgctgtg tggacaagtt tgacattatt gggattattg gagaaggaac ctatggccaa    2220
gtatataaag ccaaggacaa agacacagga gaactagtgg ctctgaagaa ggtgagacta    2280
gacaatgaga aagagggctt cccaatcaca gccattcgtg aaatcaaaat ccttcgtcag    2340
ttaatccacc gaagtgttgt taacatgaag gaaattgtca cagataaaca agatgcactg    2400
gatttcaaga aggacaaagg tgccttttac cttgtatttg agtatatgga ccatgactta    2460
atgggactgc tagaatctgg tttggtgcac ttttctgagg accatatcaa gtcgttcatg    2520
aaacagctaa tggaaggatt ggaatactgt cacaaaaaga atttcctgca tcgggatatt    2580
aagtgttcta acattttgct gaataacagt gggcaaatca aactagcaga ttttggactt    2640
gctcggctct ataactctga agagagtcgc ccttacacaa acaaagtcat tactttgtgg    2700
taccgacctc cagaactact gctaggagag gaacgttaca caccagccat agatgtttgg    2760
agctgtggat gtattcttgg ggaactattc acaaagaagc ctatttttca gccaatctg     2820 gaactggctc agctagaact gatcagccga ctttgtggta gcccttgtcc agctgtgtgg    2880
cctgatgtta tcaaactgcc ctacttcaac accatgaaac cgaagaagca atatcgaagg    2940
cgtctacgag aagaattctc tttcattcct tctgcagcac ttgatttatt ggaccacatg    3000
ctgacactag atcctagtaa gcggtgcaca gctgaacaga ccctacagag cgacttcctt    3060
aaagatgtcg aactcagcaa aatggctcct ccagacctcc cccactggca ggattgccat    3120
gagttgtgga gtaagaaacg cgacgtcag cgacaaagtg gtgttgtagt cgaagagcca    3180
cctccatcca aaacttctcg aaaagaaact acctcaggga caagtactga gcctgtgaag    3240
aacagcagcc cagcaccacc tcagcctgct cctggcaagg tggagtctgg ggctggggat    3300
gcaataggcc ttgctgacat cacacaacag ctgaatcaaa gtgaattggc agtgttatta    3360
aacctgctgc agagccaaac cgacctgagc atccctcaaa tggcacagct gcttaacatc    3420
cactccaacc cagagatgca gcagcagctg gaagccctga accaatccat cagtgccctg    3480
```

```
acggaagcta cttcccagca gcaggactca gagaccatgg ccccagagga gtctttgaag   3540
gaagcaccct ctgccccagt gatcctgcct tcagcagaac agacgaccct tgaagcttca   3600
agcacaccag ctgacatgca gaatatattg gcagttctct tgagtcagct gatgaaaacc   3660
caagagccag caggcagtct ggaggaaaac aacagtgaca agaacagtgg gccacagggg   3720
ccccgaagaa ctcccacaat gccacaggag gaggcagcag agaagaggcc ccctgagccc   3780 cccgacctc caccgccgcc acctccaccc cctctggttg aaggcgatct ttccagcgcc   3840
ccccaggagt tgaacccagc cgtgacagcc gccttgctgc aacttttatc ccagcctgaa   3900
gcagagcctc ctggccacct gccacatgag caccaggcct tgagaccaat ggagtactcc   3960
acccgacccc gtccaaacag gacttatgga aacactgatg ggcctgaaac agggttcagt   4020
gccattgaca ctgatgaacg aaactctggt ccagccttga cagaatcctt ggtccagacc   4080
ctggtgaaga acaggaccct tcaggctct ctgagccacc ttggggagtc cagcagttac   4140
cagggcacag ggtcagtgca gtttccaggg gaccaggacc tccgttttgc cagggtcccc   4200
ttagcgttac acccggtggt cgggcaacca ttcctgaagg ctgagggaag cagcaattct   4260
gtggtacatg cagagaccaa attgcaaaac tatggggagc tggggccagg aaccactggg   4320
gccagcagct caggagcagg ccttcactgg gggggcccaa ctcagtcttc tgcttatgga   4380
aaactctatc gggggcctac aagagtccca ccaagagggg gaagagggag aggagttcct   4440
tactaa                                                              4446
```

<210> SEQ ID NO 5
<211> LENGTH: 1490
<212> TYPE: PRT
<213> ORGANISM: Homo sapiens

<400> SEQUENCE: 5

```
Met Pro Asn Ser Glu Arg His Gly Gly Lys Lys Asp Gly Ser Gly Gly
1               5                   10                  15

Ala Ser Gly Thr Leu Gln Pro Ser Ser Gly Gly Ser Ser Asn Ser
            20                  25                  30

Arg Glu Arg His Arg Leu Val Ser Lys His Lys Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Lys Glu Ser Arg Ser
                165                 170                 175

Ser Lys Leu His Lys Glu Lys Thr Arg Lys Glu Arg Glu Leu Lys Ser
            180                 185                 190
```

-continued

```
Gly His Lys Asp Arg Ser Lys Ser His Arg Lys Arg Glu Thr Pro Lys
            195                 200                 205
Ser Tyr Lys Thr Val Asp Ser Pro Lys Arg Arg Ser Arg Ser Pro His
    210                 215                 220
Arg Lys Trp Ser Asp Ser Ser Lys Gln Asp Asp Ser Pro Ser Gly Ala
225                 230                 235                 240
Ser Tyr Gly Gln Asp Tyr Asp Leu Ser Pro Ser Arg Ser His Thr Ser
                245                 250                 255
Ser Asn Tyr Asp Ser Tyr Lys Lys Ser Pro Gly Ser Thr Ser Arg Arg
                260                 265                 270
Gln Ser Val Ser Pro Pro Tyr Lys Glu Pro Ser Ala Tyr Gln Ser Ser
            275                 280                 285
Thr Arg Ser Pro Ser Pro Tyr Ser Arg Arg Gln Arg Ser Val Ser Pro
        290                 295                 300
Tyr Ser Arg Arg Arg Ser Ser Tyr Glu Arg Ser Gly Ser Tyr Ser
305                 310                 315                 320
Gly Arg Ser Pro Ser Pro Tyr Gly Arg Arg Ser Ser Ser Pro Phe
                325                 330                 335
Leu Ser Lys Arg Ser Leu Ser Arg Ser Pro Leu Pro Ser Arg Lys Ser
                340                 345                 350
Met Lys Ser Arg Ser Arg Ser Pro Ala Tyr Ser Arg His Ser Ser Ser
            355                 360                 365
His Ser Lys Lys Arg Ser Ser Arg Ser Arg His Ser Ser Ile
        370                 375                 380
Ser Pro Val Arg Leu Pro Leu Asn Ser Ser Leu Gly Ala Glu Leu Ser
385                 390                 395                 400
Arg Lys Lys Lys Glu Arg Ala Ala Ala Ala Ala Ala Lys Met Asp
                405                 410                 415
Gly Lys Glu Ser Lys Gly Ser Pro Val Phe Leu Pro Arg Lys Glu Asn
                420                 425                 430
Ser Ser Val Glu Ala Lys Asp Ser Gly Leu Glu Ser Lys Lys Leu Pro
            435                 440                 445
Arg Ser Val Lys Leu Glu Lys Ser Ala Pro Asp Thr Glu Leu Val Asn
450                 455                 460
Val Thr His Leu Asn Thr Glu Val Lys Asn Ser Ser Asp Thr Gly Lys
465                 470                 475                 480
Val Lys Leu Asp Glu Asn Ser Glu Lys His Leu Val Lys Asp Leu Lys
                485                 490                 495
Ala Gln Gly Thr Arg Asp Ser Lys Pro Ile Ala Leu Lys Glu Glu Ile
            500                 505                 510
Val Thr Pro Lys Glu Thr Glu Thr Ser Glu Lys Glu Thr Pro Pro Pro
        515                 520                 525
Leu Pro Thr Ile Ala Ser Pro Pro Pro Leu Pro Thr Thr Thr Pro
    530                 535                 540
Pro Pro Gln Thr Pro Pro Leu Pro Pro Leu Pro Ile Pro Ala Leu
545                 550                 555                 560
Pro Gln Gln Pro Pro Leu Pro Pro Ser Gln Pro Ala Phe Ser Gln Val
                565                 570                 575
Pro Ala Ser Ser Thr Ser Thr Leu Pro Pro Ser Thr His Ser Lys Thr
            580                 585                 590
Ser Ala Val Ser Ser Gln Ala Asn Ser Gln Pro Pro Val Gln Val Ser
        595                 600                 605
Val Lys Thr Gln Val Ser Val Thr Ala Ala Ile Pro His Leu Lys Thr
```

```
               610                 615                 620
Ser Thr Leu Pro Pro Leu Pro Leu Pro Pro Leu Pro Gly Asp Asp
625                 630                 635                 640

Asp Met Asp Ser Pro Lys Glu Thr Leu Pro Ser Lys Pro Val Lys Lys
                645                 650                 655

Glu Lys Glu Gln Arg Thr Arg His Leu Leu Thr Asp Leu Pro Leu Pro
                660                 665                 670

Pro Glu Leu Pro Gly Gly Asp Leu Ser Pro Pro Asp Ser Pro Glu Pro
                675                 680                 685

Lys Ala Ile Thr Pro Pro Gln Gln Pro Tyr Lys Lys Arg Pro Lys Ile
            690                 695                 700

Cys Cys Pro Arg Tyr Gly Glu Arg Arg Gln Thr Glu Ser Asp Trp Gly
705                 710                 715                 720

Lys Arg Cys Val Asp Lys Phe Asp Ile Ile Gly Ile Ile Gly Glu Gly
                725                 730                 735

Thr Tyr Gly Gln Val Tyr Lys Ala Lys Asp Lys Asp Thr Gly Glu Leu
                740                 745                 750

Val Ala Leu Lys Lys Val Arg Leu Asp Asn Glu Lys Glu Gly Phe Pro
                755                 760                 765

Ile Thr Ala Ile Arg Glu Ile Lys Ile Leu Arg Gln Leu Ile His Arg
770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
                820                 825                 830

Glu Asp His Ile Lys Ser Phe Met Lys Gln Leu Met Glu Gly Leu Glu
                835                 840                 845

Tyr Cys His Lys Lys Asn Phe Leu His Arg Asp Ile Lys Cys Ser Asn
                850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Leu Gly Glu Glu Arg
                900                 905                 910

Tyr Thr Pro Ala Ile Asp Val Trp Ser Cys Gly Cys Ile Leu Gly Glu
                915                 920                 925

Leu Phe Thr Lys Lys Pro Ile Phe Gln Ala Asn Leu Glu Leu Ala Gln
930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
                965                 970                 975

Gln Tyr Arg Arg Arg Leu Arg Glu Glu Phe Ser Phe Ile Pro Ser Ala
                980                 985                 990

Ala Leu Asp Leu Leu Asp His Met Leu Thr Leu Asp Pro Ser Lys Arg
                995                 1000                1005

Cys Thr Ala Glu Gln Thr Leu Gln Ser Asp Phe Leu Lys Asp Val
    1010                1015                1020

Glu Leu Ser Lys Met Ala Pro Pro Asp Leu Pro His Trp Gln Asp
    1025                1030                1035
```

```
Cys His Glu Leu Trp Ser Lys Lys Arg Arg Gln Arg Gln Ser
1040             1045                 1050

Gly Val Val Glu Glu Pro Pro Ser Lys Thr Ser Arg Lys
1055             1060                 1065

Glu Thr Thr Ser Gly Thr Ser Thr Glu Pro Val Lys Asn Ser Ser
1070             1075                 1080

Pro Ala Pro Pro Gln Pro Ala Pro Gly Lys Val Glu Ser Gly Ala
1085             1090                 1095

Gly Asp Ala Ile Gly Leu Ala Asp Ile Thr Gln Gln Leu Asn Gln
1100             1105                 1110

Ser Glu Leu Ala Val Leu Leu Asn Leu Leu Gln Ser Gln Thr Asp
1115             1120                 1125

Leu Ser Ile Pro Gln Met Ala Gln Leu Leu Asn Ile His Ser Asn
1130             1135                 1140

Pro Glu Met Gln Gln Leu Glu Ala Leu Asn Gln Ser Ile Ser
1145             1150                 1155

Ala Leu Thr Glu Ala Thr Ser Gln Gln Gln Asp Ser Glu Thr Met
1160             1165                 1170

Ala Pro Glu Glu Ser Leu Lys Glu Ala Pro Ser Ala Pro Val Ile
1175             1180                 1185

Leu Pro Ser Ala Glu Gln Thr Thr Leu Glu Ala Ser Ser Thr Pro
1190             1195                 1200

Ala Asp Met Gln Asn Ile Leu Ala Val Leu Leu Ser Gln Leu Met
1205             1210                 1215

Lys Thr Gln Glu Pro Ala Gly Ser Leu Glu Glu Asn Asn Ser Asp
1220             1225                 1230

Lys Asn Ser Gly Pro Gln Gly Pro Arg Arg Thr Pro Thr Met Pro
1235             1240                 1245

Gln Glu Glu Ala Ala Ala Cys Pro Pro His Ile Leu Pro Pro Glu
1250             1255                 1260

Lys Arg Pro Pro Glu Pro Pro Gly Pro Pro Pro Pro Pro Pro
1265             1270                 1275

Pro Pro Leu Val Glu Gly Asp Leu Ser Ser Ala Pro Gln Glu Leu
1280             1285                 1290

Asn Pro Ala Val Thr Ala Ala Leu Leu Gln Leu Leu Ser Gln Pro
1295             1300                 1305

Glu Ala Glu Pro Pro Gly His Leu Pro His Glu His Gln Ala Leu
1310             1315                 1320

Arg Pro Met Glu Tyr Ser Thr Arg Pro Arg Pro Asn Arg Thr Tyr
1325             1330                 1335

Gly Asn Thr Asp Gly Pro Glu Thr Gly Phe Ser Ala Ile Asp Thr
1340             1345                 1350

Asp Glu Arg Asn Ser Gly Pro Ala Leu Thr Glu Ser Leu Val Gln
1355             1360                 1365

Thr Leu Val Lys Asn Arg Thr Phe Ser Gly Ser Leu Ser His Leu
1370             1375                 1380

Gly Glu Ser Ser Ser Tyr Gln Gly Thr Gly Ser Val Gln Phe Pro
1385             1390                 1395

Gly Asp Gln Asp Leu Arg Phe Ala Arg Val Pro Leu Ala Leu His
1400             1405                 1410

Pro Val Val Gly Gln Pro Phe Leu Lys Ala Glu Gly Ser Ser Asn
1415             1420                 1425
```

-continued

```
Ser Val Val His Ala Glu Thr Lys Leu Gln Asn Tyr Gly Glu Leu
    1430                1435                1440

Gly Pro Gly Thr Thr Gly Ala Ser Ser Ser Gly Ala Gly Leu His
    1445                1450                1455

Trp Gly Gly Pro Thr Gln Ser Ser Ala Tyr Gly Lys Leu Tyr Arg
    1460                1465                1470

Gly Pro Thr Arg Val Pro Pro Arg Gly Gly Arg Gly Arg Gly Val
    1475                1480                1485

Pro Tyr
    1490

<210> SEQ ID NO 6
<211> LENGTH: 1481
<212> TYPE: PRT
<213> ORGANISM: Homo sapiens

<400> SEQUENCE: 6

Met Pro Asn Ser Glu Arg His Gly Gly Lys Lys Asp Gly Ser Gly Gly
1               5                   10                  15

Ala Ser Gly Thr Leu Gln Pro Ser Gly Gly Gly Ser Ser Asn Ser
            20                  25                  30

Arg Glu Arg His Arg Leu Val Ser Lys His Lys Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Lys Ser Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205

Ser Tyr Lys Thr Val Asp Ser Pro Lys Arg Arg Ser Arg Ser Pro His
    210                 215                 220

Arg Lys Trp Ser Asp Ser Ser Lys Gln Asp Asp Ser Pro Ser Gly Ala
225                 230                 235                 240

Ser Tyr Gly Gln Asp Tyr Asp Leu Ser Pro Ser Arg Ser His Thr Ser
                245                 250                 255

Ser Asn Tyr Asp Ser Tyr Lys Lys Ser Pro Gly Ser Thr Ser Arg Arg
            260                 265                 270

Gln Ser Val Ser Pro Pro Tyr Lys Glu Pro Ser Ala Tyr Gln Ser Ser
        275                 280                 285

Thr Arg Ser Pro Ser Pro Tyr Ser Arg Arg Gln Arg Ser Val Ser Pro
    290                 295                 300
```

```
Tyr Ser Arg Arg Arg Ser Ser Tyr Glu Arg Ser Gly Tyr Ser
305                 310                 315                 320

Gly Arg Ser Pro Ser Pro Tyr Gly Arg Arg Ser Ser Ser Pro Phe
            325                 330                 335

Leu Ser Lys Arg Ser Leu Ser Arg Ser Pro Leu Pro Ser Arg Lys Ser
            340                 345                 350

Met Lys Ser Arg Ser Arg Ser Pro Ala Tyr Ser Arg His Ser Ser Ser
            355                 360                 365

His Ser Lys Lys Lys Arg Ser Ser Arg Ser Arg His Ser Ser Ile
370                 375                 380

Ser Pro Val Arg Leu Pro Leu Asn Ser Ser Leu Gly Ala Glu Leu Ser
385                 390                 395                 400

Arg Lys Lys Lys Glu Arg Ala Ala Ala Ala Ala Ala Lys Met Asp
                405                 410                 415

Gly Lys Glu Ser Lys Gly Ser Pro Val Phe Leu Pro Arg Lys Glu Asn
            420                 425                 430

Ser Ser Val Glu Ala Lys Asp Ser Gly Leu Glu Ser Lys Lys Leu Pro
            435                 440                 445

Arg Ser Val Lys Leu Glu Lys Ser Ala Pro Asp Thr Glu Leu Val Asn
450                 455                 460

Val Thr His Leu Asn Thr Glu Val Lys Asn Ser Ser Asp Thr Gly Lys
465                 470                 475                 480

Val Lys Leu Asp Glu Asn Ser Glu Lys His Leu Val Lys Asp Leu Lys
                485                 490                 495

Ala Gln Gly Thr Arg Asp Ser Lys Pro Ile Ala Leu Lys Glu Glu Ile
            500                 505                 510

Val Thr Pro Lys Glu Thr Glu Thr Ser Glu Lys Glu Thr Pro Pro
            515                 520                 525

Leu Pro Thr Ile Ala Ser Pro Pro Pro Leu Pro Thr Thr Thr Pro
530                 535                 540

Pro Pro Gln Thr Pro Pro Leu Pro Pro Leu Pro Ile Pro Ala Leu
545                 550                 555                 560

Pro Gln Gln Pro Pro Leu Pro Pro Ser Gln Pro Ala Phe Ser Gln Val
            565                 570                 575

Pro Ala Ser Ser Thr Ser Thr Leu Pro Pro Ser Thr His Ser Lys Thr
            580                 585                 590

Ser Ala Val Ser Ser Gln Ala Asn Ser Gln Pro Pro Val Gln Val Ser
            595                 600                 605

Val Lys Thr Gln Val Ser Val Thr Ala Ala Ile Pro His Leu Lys Thr
            610                 615                 620

Ser Thr Leu Pro Pro Leu Pro Leu Pro Pro Leu Leu Pro Gly Asp Asp
625                 630                 635                 640

Asp Met Asp Ser Pro Lys Glu Thr Leu Pro Ser Lys Pro Val Lys Lys
                645                 650                 655

Glu Lys Glu Gln Arg Thr Arg His Leu Leu Thr Asp Leu Pro Leu Pro
            660                 665                 670

Pro Glu Leu Pro Gly Gly Asp Leu Ser Pro Asp Ser Pro Glu Pro
            675                 680                 685

Lys Ala Ile Thr Pro Gln Gln Pro Tyr Lys Lys Arg Pro Lys Ile
690                 695                 700

Cys Cys Pro Arg Tyr Gly Glu Arg Arg Gln Thr Glu Ser Asp Trp Gly
705                 710                 715                 720
```

Lys Arg Cys Val Asp Lys Phe Asp Ile Ile Gly Ile Gly Glu Gly
                725                 730                 735

Thr Tyr Gly Gln Val Tyr Lys Ala Lys Asp Lys Asp Thr Gly Glu Leu
                740                 745                 750

Val Ala Leu Lys Lys Val Arg Leu Asp Asn Glu Lys Glu Gly Phe Pro
                755                 760                 765

Ile Thr Ala Ile Arg Glu Ile Lys Ile Leu Arg Gln Leu Ile His Arg
                770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
                820                 825                 830

Glu Asp His Ile Lys Ser Phe Met Lys Gln Leu Met Glu Gly Leu Glu
                835                 840                 845

Tyr Cys His Lys Lys Asn Phe Leu His Arg Asp Ile Lys Cys Ser Asn
                850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Leu Gly Glu Arg
                900                 905                 910

Tyr Thr Pro Ala Ile Asp Val Trp Ser Cys Gly Cys Ile Leu Gly Glu
                915                 920                 925

Leu Phe Thr Lys Lys Pro Ile Phe Gln Ala Asn Leu Glu Leu Ala Gln
                930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
                965                 970                 975

Gln Tyr Arg Arg Arg Leu Arg Glu Glu Phe Ser Phe Ile Pro Ser Ala
                980                 985                 990

Ala Leu Asp Leu Leu Asp His Met Leu Thr Leu Asp Pro Ser Lys Arg
                995                 1000                1005

Cys Thr Ala Glu Gln Thr Leu Gln Ser Asp Phe Leu Lys Asp Val
        1010                1015                1020

Glu Leu Ser Lys Met Ala Pro Pro Asp Leu Pro His Trp Gln Asp
        1025                1030                1035

Cys His Glu Leu Trp Ser Lys Lys Arg Arg Arg Gln Arg Gln Ser
        1040                1045                1050

Gly Val Val Val Glu Glu Pro Pro Pro Ser Lys Thr Ser Arg Lys
        1055                1060                1065

Glu Thr Thr Ser Gly Thr Ser Thr Glu Pro Val Lys Asn Ser Ser
        1070                1075                1080

Pro Ala Pro Pro Gln Pro Ala Pro Gly Lys Val Glu Ser Gly Ala
        1085                1090                1095

Gly Asp Ala Ile Gly Leu Ala Asp Ile Thr Gln Gln Leu Asn Gln
        1100                1105                1110

Ser Glu Leu Ala Val Leu Leu Asn Leu Leu Gln Ser Gln Thr Asp
        1115                1120                1125

Leu Ser Ile Pro Gln Met Ala Gln Leu Leu Asn Ile His Ser Asn

-continued

| | 1130 | | | 1135 | | | 1140 | | |

Pro Glu Met Gln Gln Gln Leu Glu Ala Leu Asn Gln Ser Ile Ser
1145                1150                1155

Ala Leu Thr Glu Ala Thr Ser Gln Gln Gln Asp Ser Glu Thr Met
1160                1165                1170

Ala Pro Glu Glu Ser Leu Lys Glu Ala Pro Ser Ala Pro Val Ile
1175                1180                1185

Leu Pro Ser Ala Glu Gln Thr Thr Leu Glu Ala Ser Ser Thr Pro
1190                1195                1200

Ala Asp Met Gln Asn Ile Leu Ala Val Leu Leu Ser Gln Leu Met
1205                1210                1215

Lys Thr Gln Glu Pro Ala Gly Ser Leu Glu Glu Asn Asn Ser Asp
1220                1225                1230

Lys Asn Ser Gly Pro Gln Gly Pro Arg Arg Thr Pro Thr Met Pro
1235                1240                1245

Gln Glu Glu Ala Ala Glu Lys Arg Pro Pro Glu Pro Pro Gly Pro
1250                1255                1260

Pro Pro Pro Pro Pro Pro Pro Leu Val Glu Gly Asp Leu Ser
1265                1270                1275

Ser Ala Pro Gln Glu Leu Asn Pro Ala Val Thr Ala Ala Leu Leu
1280                1285                1290

Gln Leu Leu Ser Gln Pro Glu Ala Glu Pro Pro Gly His Leu Pro
1295                1300                1305

His Glu His Gln Ala Leu Arg Pro Met Glu Tyr Ser Thr Arg Pro
1310                1315                1320

Arg Pro Asn Arg Thr Tyr Gly Asn Thr Asp Gly Pro Glu Thr Gly
1325                1330                1335

Phe Ser Ala Ile Asp Thr Asp Glu Arg Asn Ser Gly Pro Ala Leu
1340                1345                1350

Thr Glu Ser Leu Val Gln Thr Leu Val Lys Asn Arg Thr Phe Ser
1355                1360                1365

Gly Ser Leu Ser His Leu Gly Glu Ser Ser Ser Tyr Gln Gly Thr
1370                1375                1380

Gly Ser Val Gln Phe Pro Gly Asp Gln Asp Leu Arg Phe Ala Arg
1385                1390                1395

Val Pro Leu Ala Leu His Pro Val Val Gly Gln Pro Phe Leu Lys
1400                1405                1410

Ala Glu Gly Ser Ser Asn Ser Val Val His Ala Glu Thr Lys Leu
1415                1420                1425

Gln Asn Tyr Gly Glu Leu Gly Pro Gly Thr Thr Gly Ala Ser Ser
1430                1435                1440

Ser Gly Ala Gly Leu His Trp Gly Gly Pro Thr Gln Ser Ser Ala
1445                1450                1455

Tyr Gly Lys Leu Tyr Arg Gly Pro Thr Arg Val Pro Pro Arg Gly
1460                1465                1470

Gly Arg Gly Arg Gly Val Pro Tyr
1475                1480

<210> SEQ ID NO 7
<211> LENGTH: 19
<212> TYPE: DNA
<213> ORGANISM: Artificial
<220> FEATURE:
<223> OTHER INFORMATION: shRNA for CDK12

```
<400> SEQUENCE: 7
tctcctgtgt ctttgtcct                                              19

<210> SEQ ID NO 8
<211> LENGTH: 19
<212> TYPE: DNA
<213> ORGANISM: Artificial
<220> FEATURE:
<223> OTHER INFORMATION: shRNA for CDK12

<400> SEQUENCE: 8
tcaggacact gaagtctct                                              19

<210> SEQ ID NO 9
<211> LENGTH: 23
<212> TYPE: DNA
<213> ORGANISM: Artificial
<220> FEATURE:
<223> OTHER INFORMATION: CDK12 primer

<400> SEQUENCE: 9
cctggagatg atgacatgga tag                                         23

<210> SEQ ID NO 10
<211> LENGTH: 20
<212> TYPE: DNA
<213> ORGANISM: Artificial
<220> FEATURE:
<223> OTHER INFORMATION: WNT1 primer

<400> SEQUENCE: 10
ccgatggtgg ggtattgtga                                             20

<210> SEQ ID NO 11
<211> LENGTH: 20
<212> TYPE: DNA
<213> ORGANISM: Artificial
<220> FEATURE:
<223> OTHER INFORMATION: WNT1 primer

<400> SEQUENCE: 11
cccggatttt ggcgtatcag                                             20

<210> SEQ ID NO 12
<211> LENGTH: 20
<212> TYPE: DNA
<213> ORGANISM: Artificial
<220> FEATURE:
<223> OTHER INFORMATION: WNT3 primer

<400> SEQUENCE: 12
cgtgttagtg tccagggagt                                             20

<210> SEQ ID NO 13
<211> LENGTH: 20
<212> TYPE: DNA
<213> ORGANISM: Artificial
<220> FEATURE:
<223> OTHER INFORMATION: WNT3 primer

<400> SEQUENCE: 13
gcatttgagg tgcatgtggt                                             20

<210> SEQ ID NO 14
<211> LENGTH: 20
```

```
<212> TYPE: DNA
<213> ORGANISM: Artificial
<220> FEATURE:
<223> OTHER INFORMATION: IRS1 primer

<400> SEQUENCE: 14
ggtggatgac tctgtggtgg                                              20

<210> SEQ ID NO 15
<211> LENGTH: 20
<212> TYPE: DNA
<213> ORGANISM: Artificial
<220> FEATURE:
<223> OTHER INFORMATION: IRS1 primer

<400> SEQUENCE: 15
ggacgctgat ggggttagag                                              20

<210> SEQ ID NO 16
<211> LENGTH: 20
<212> TYPE: DNA
<213> ORGANISM: Artificial
<220> FEATURE:
<223> OTHER INFORMATION: AQP3 primer

<400> SEQUENCE: 16
tgctacctac ccctctggac                                              20

<210> SEQ ID NO 17
<211> LENGTH: 20
<212> TYPE: DNA
<213> ORGANISM: Artificial
<220> FEATURE:
<223> OTHER INFORMATION: AQP3 primer

<400> SEQUENCE: 17
gtcaacaatg gccagcacac                                              20

<210> SEQ ID NO 18
<211> LENGTH: 20
<212> TYPE: DNA
<213> ORGANISM: Artificial
<220> FEATURE:
<223> OTHER INFORMATION: CD74 primer

<400> SEQUENCE: 18
acggcaacta tctgccactc                                              20

<210> SEQ ID NO 19
<211> LENGTH: 20
<212> TYPE: DNA
<213> ORGANISM: Artificial
<220> FEATURE:
<223> OTHER INFORMATION: CD74 primer

<400> SEQUENCE: 19
ctctcacatg gggactgggc                                              20

<210> SEQ ID NO 20
<211> LENGTH: 20
<212> TYPE: DNA
<213> ORGANISM: Artificial
<220> FEATURE:
<223> OTHER INFORMATION: TSPAN8 Primer

<400> SEQUENCE: 20
```

-continued cccaggagct atgacaagca                                     20

<210> SEQ ID NO 21
<211> LENGTH: 20
<212> TYPE: DNA
<213> ORGANISM: Artificial
<220> FEATURE:
<223> OTHER INFORMATION: TSPAN8 Primer

<400> SEQUENCE: 21
gcactcacac ctgccatttc                                     20

<210> SEQ ID NO 22
<211> LENGTH: 21
<212> TYPE: DNA
<213> ORGANISM: Artificial
<220> FEATURE:
<223> OTHER INFORMATION: FGF8 Primer

<400> SEQUENCE: 22
gggtgtctcc caacaggtaa c                                   21

<210> SEQ ID NO 23
<211> LENGTH: 20
<212> TYPE: DNA
<213> ORGANISM: Artificial
<220> FEATURE:
<223> OTHER INFORMATION: FGF8 Primer

<400> SEQUENCE: 23
tctgcttcca aggtgtccg                                      20

<210> SEQ ID NO 24
<211> LENGTH: 20
<212> TYPE: DNA
<213> ORGANISM: Artificial
<220> FEATURE:
<223> OTHER INFORMATION: FGF19 Primer

<400> SEQUENCE: 24
gctttcgagg aggagatccg                                     20

<210> SEQ ID NO 25
<211> LENGTH: 20
<212> TYPE: DNA
<213> ORGANISM: Artificial
<220> FEATURE:
<223> OTHER INFORMATION: FGF19 Primer

<400> SEQUENCE: 25
ggggcgaaga gaacatgtca                                     20

<210> SEQ ID NO 26
<211> LENGTH: 20
<212> TYPE: DNA
<213> ORGANISM: Artificial
<220> FEATURE:
<223> OTHER INFORMATION: WNT5B primer

<400> SEQUENCE: 26
caggagcaca tggcctacat                                     20

<210> SEQ ID NO 27
<211> LENGTH: 20
<212> TYPE: DNA
<213> ORGANISM: Artificial

```
<220> FEATURE:
<223> OTHER INFORMATION: WNT5B primer

<400> SEQUENCE: 27
ggctgcctat ctgcatgact                                              20

<210> SEQ ID NO 28
<211> LENGTH: 20
<212> TYPE: DNA
<213> ORGANISM: Artificial
<220> FEATURE:
<223> OTHER INFORMATION: TCF7 Primer

<400> SEQUENCE: 28
acatgcagct atacccaggc                                              20

<210> SEQ ID NO 29
<211> LENGTH: 20
<212> TYPE: DNA
<213> ORGANISM: Artificial
<220> FEATURE:
<223> OTHER INFORMATION: TCF7 Primer

<400> SEQUENCE: 29
actgtcatcg gaaggaacgg                                              20

<210> SEQ ID NO 30
<211> LENGTH: 20
<212> TYPE: DNA
<213> ORGANISM: Artificial
<220> FEATURE:
<223> OTHER INFORMATION: DKK1 Primer

<400> SEQUENCE: 30
gtgcaaatct gtctcgcctg                                              20

<210> SEQ ID NO 31
<211> LENGTH: 20
<212> TYPE: DNA
<213> ORGANISM: Artificial
<220> FEATURE:
<223> OTHER INFORMATION: DKK1 Primer

<400> SEQUENCE: 31
gcacaacaca atcctgaggc                                              20

<210> SEQ ID NO 32
<211> LENGTH: 20
<212> TYPE: DNA
<213> ORGANISM: Artificial
<220> FEATURE:
<223> OTHER INFORMATION: TLE1 primer

<400> SEQUENCE: 32
ccgctgtgac tactctggac                                              20

<210> SEQ ID NO 33
<211> LENGTH: 20
<212> TYPE: DNA
<213> ORGANISM: Artificial
<220> FEATURE:
<223> OTHER INFORMATION: TLE1 primer

<400> SEQUENCE: 33
agggacgaca tccacgagat                                              20
```

```
<210> SEQ ID NO 34
<211> LENGTH: 20
<212> TYPE: DNA
<213> ORGANISM: Artificial
<220> FEATURE:
<223> OTHER INFORMATION: MMP9 Primer

<400> SEQUENCE: 34
cagtccaccc ttgtgctctt                                              20

<210> SEQ ID NO 35
<211> LENGTH: 20
<212> TYPE: DNA
<213> ORGANISM: Artificial
<220> FEATURE:
<223> OTHER INFORMATION: MMP9 Primer

<400> SEQUENCE: 35
cgactctcca cgcatctctg                                              20

<210> SEQ ID NO 36
<211> LENGTH: 20
<212> TYPE: DNA
<213> ORGANISM: Artificial
<220> FEATURE:
<223> OTHER INFORMATION: MYCBP Primer

<400> SEQUENCE: 36
agagctgctt cgcctagaac                                              20

<210> SEQ ID NO 37
<211> LENGTH: 21
<212> TYPE: DNA
<213> ORGANISM: Artificial
<220> FEATURE:
<223> OTHER INFORMATION: MYCBP Primer

<400> SEQUENCE: 37
ttctcctcct gaggtggttc a                                            21

<210> SEQ ID NO 38
<211> LENGTH: 20
<212> TYPE: DNA
<213> ORGANISM: Artificial
<220> FEATURE:
<223> OTHER INFORMATION: TWIST Primer

<400> SEQUENCE: 38
cggacaagct gagcaagatt                                              20

<210> SEQ ID NO 39
<211> LENGTH: 20
<212> TYPE: DNA
<213> ORGANISM: Artificial
<220> FEATURE:
<223> OTHER INFORMATION: TWIST Primer

<400> SEQUENCE: 39
ccttctctgg aaacaatgac                                              20

<210> SEQ ID NO 40
<211> LENGTH: 21
<212> TYPE: DNA
<213> ORGANISM: Artificial
<220> FEATURE:
<223> OTHER INFORMATION: SNAI1 Primer
```

```
<400> SEQUENCE: 40
agcctgggtg ccctcaagat g                                        21

<210> SEQ ID NO 41
<211> LENGTH: 23
<212> TYPE: DNA
<213> ORGANISM: Artificial
<220> FEATURE:
<223> OTHER INFORMATION: SNAI1 primer

<400> SEQUENCE: 41
cttggtgctt gtggagcagg gac                                      23

<210> SEQ ID NO 42
<211> LENGTH: 19
<212> TYPE: DNA
<213> ORGANISM: Artificial
<220> FEATURE:
<223> OTHER INFORMATION: GAPDH Primer

<400> SEQUENCE: 42
gaaggtgaag gtcggagtc                                           19

<210> SEQ ID NO 43
<211> LENGTH: 20
<212> TYPE: DNA
<213> ORGANISM: Artificial
<220> FEATURE:
<223> OTHER INFORMATION: GAPDH Primer

<400> SEQUENCE: 43
gaagatggtg atgggatttc                                          20

<210> SEQ ID NO 44
<211> LENGTH: 20
<212> TYPE: DNA
<213> ORGANISM: Artificial Sequence
<220> FEATURE:
<223> OTHER INFORMATION: IRS1 TSS primer

<400> SEQUENCE: 44
cgtggatttc agagtcgggg                                          20

<210> SEQ ID NO 45
<211> LENGTH: 20
<212> TYPE: DNA
<213> ORGANISM: Artificial Sequence
<220> FEATURE:
<223> OTHER INFORMATION: IRS1 TSS primer

<400> SEQUENCE: 45
gaggctccga aaacaaccg                                           20

<210> SEQ ID NO 46
<211> LENGTH: 19
<212> TYPE: DNA
<213> ORGANISM: Artificial Sequence
<220> FEATURE:
<223> OTHER INFORMATION: WNT1 TSS primer

<400> SEQUENCE: 46
ccattgtctg cgcccctaa                                           19

<210> SEQ ID NO 47
```

```
<211> LENGTH: 19
<212> TYPE: DNA
<213> ORGANISM: Artificial Sequence
<220> FEATURE:
<223> OTHER INFORMATION: WNT1 TSS primer

<400> SEQUENCE: 47
cggcaccgcc tcttatagt                                               19

<210> SEQ ID NO 48
<211> LENGTH: 20
<212> TYPE: DNA
<213> ORGANISM: Artificial Sequence
<220> FEATURE:
<223> OTHER INFORMATION: WNT3 TSS primer

<400> SEQUENCE: 48
tcgctgacat cctcaaaccc                                              20

<210> SEQ ID NO 49
<211> LENGTH: 20
<212> TYPE: DNA
<213> ORGANISM: Artificial Sequence
<220> FEATURE:
<223> OTHER INFORMATION: WNT3 TSS primer

<400> SEQUENCE: 49
gacgccccca atagttggaa                                              20
```